(12) United States Patent
Kim et al.

(10) Patent No.: US 8,389,986 B2
(45) Date of Patent: Mar. 5, 2013

(54) CONDENSED-CYCLIC COMPOUND AND ORGANIC LIGHT-EMITTING DEVICE INCLUDING THE SAME

(75) Inventors: Hee-Yeon Kim, Yongin (KR);
Seung-Gak Yang, Yongin (KR);
Jeoung-In Yi, Yongin (KR); Jae-Yong Lee, Yongin (KR); Yoon-Hyun Kwak, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 132 days.

(21) Appl. No.: 13/078,491

(22) Filed: Apr. 1, 2011

(65) Prior Publication Data

US 2011/0240979 A1    Oct. 6, 2011

(30) Foreign Application Priority Data

Apr. 1, 2010  (KR) .................. 10-2010-0029992
Mar. 29, 2011  (KR) .................. 10-2011-0028212

(51) Int. Cl.
*H01L 51/00*    (2006.01)
(52) U.S. Cl. .................. 257/40; 257/103; 257/E51.018; 257/E51.026; 257/E51.028; 548/418
(58) Field of Classification Search .................. 257/40, 257/103, E51.018, E51.026, E51.028; 548/418
See application file for complete search history.

(56) References Cited

U.S. PATENT DOCUMENTS

| | | | |
|---|---|---|---|
| 5,843,607 A | 12/1998 | Hu et al. | |
| 5,952,115 A * | 9/1999 | Hu et al. | 428/690 |
| 7,456,424 B2 | 11/2008 | Wu et al. | |
| 2008/0014464 A1 | 1/2008 | Kawamura et al. | |
| 2008/0124572 A1 | 5/2008 | Mizuki et al. | |
| 2009/0066225 A1 | 3/2009 | Kimura et al. | |
| 2009/0295276 A1 | 12/2009 | Asari et al. | |
| 2009/0302742 A1 | 12/2009 | Komori et al. | |

FOREIGN PATENT DOCUMENTS

| | | |
|---|---|---|
| DE | 198 31 427 A1 | 1/2000 |
| EP | 0 906 948 A1 | 4/1999 |
| EP | 0 908 787 A2 | 4/1999 |
| EP | 0906947 A1 | 4/1999 |
| EP | 2080762 A1 | 7/2009 |
| JP | 2008-251394 A | 10/2008 |
| KR | 10 2007-0110371 A | 11/2007 |
| KR | 10 2008-0085000 A | 9/2008 |
| KR | 10 2008-0085001 A | 9/2008 |
| KR | 10 2009-0021174 A | 2/2009 |
| KR | 10 2009-0035729 A | 4/2009 |
| KR | 10 2009-0086057 A | 8/2009 |
| KR | 10-2010-0131629 A | 12/2010 |
| KR | 10-2010-0131745 A | 12/2010 |
| KR | 10-2010-0131939 A | 12/2010 |
| KR | 10-2011-0011578 A | 2/2011 |
| WO | WO 2006/098229 A1 | 9/2006 |
| WO | WO 2010/083872 A2 | 7/2010 |
| WO | WO 2010/110553 A2 | 9/2010 |

OTHER PUBLICATIONS

Bocchi, Vittorio, et al., "Synthesis and Characterization of New Indole Trimers and Tetramers," *Tetrahedron*, vol. 42, No. 18, 1986, pp. 5019-5024.

Domiano, Paolo, et al., "Synthesis and structure of 1-(2-amino)phenyl-2-phenyl-12H-indolo[3,2-c]carbazole ethylacetate solvate, a new indolocarbazole compound," *Journal of Crystallographic and Spectroscopic Research*, vol. 19, No. 2, 1989, pp. 277-287.

Frost, Jonathan R., et al., "Intermolecular Trapping by Indole of a Spiroindolenine Intermediate Formed During the Bischler-Napieralski Cyclisation of N-acetyltryptamine," *Heterocycles*, vol. 28, No. 1, 1989, pp. 175-182.

Ishii, Hisashi, et al., "Polymerisation of Indole. Part 3. Two Indolylquinolines, an Indole Tetramer, and the Dihydro Derivative of the Indole Dimer," *Journal of the Chemical Society, Perkin Transactions 1*, 1988, pp. 2387-2395.

Laronze-Cochard, Marie, et al., "Synthesis and biological evaluation of new penta- and heptacyclic indolo- and quinolinocarbazole ring systems obtained via Pd$^0$ catalysed reductive N-heteroannulation," *Organic & Biomolecular Chemistry*, vol. 8, 2010, pp. 4625-4636.

Lengvinaite, S., et al., "Indolo[3,2-b]carbazole-based functional derivatives as materials for light emitting diodes," *Dyes and Pigments*, vol. 85, 2010, pp. 183-188.

Liu, Zhiqiang, et al. "TPA-active D-π-D fluorophores with rigid, planar cores from phenylene to indenofluorene and indolocarbazole," *Dyes and Pigments*, vol. 86, 2010, pp. 63-67.

Niebel, Claude, et al., "Dibenzo[2,3:5,6]pyrrolizino[1,7-bc]indolo[1,2,3-lm]carbazole: a new electron donor," *New Journal of Chemistry*, vol. 34, 2010, pp. 1243-1246.

Yudina, Larisa N., et al., "Synthesis and alkylation of indolo[3,2-b]carbazoles," *Tetrahedron*, vol. 59, 2003, pp. 1265-1275.

(Continued)

*Primary Examiner* — Tu-Tu Ho

(74) *Attorney, Agent, or Firm* — Lee & Morse, P.C.

(57) ABSTRACT

A condensed-cyclic compound and an OLED including the same, the condensed-cyclic compound represented by Formula 1 below:

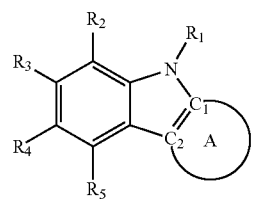

27 Claims, 1 Drawing Sheet

OTHER PUBLICATIONS

Zhao, Hua-Ping, et al., "Effect of substituents on the properties of indolo[3,2-*b*]carbazole-based hole-transporting materials," *Organic Electronics*, vol. 8, 2007, pp. 673-682.

Zhao, Hua-Ping, et al., "Indolo[3,2-*b*]carbazole: Promising building block for highly efficient electroluminescent materials," *Organic Electronics*, vol. 10, 2009, pp. 925-931.

Zhao, Hua-Ping, et al., "Structure and electronic properties of triphenylamine-substituted indolo[3,2-*b*]carbazole derivatives as hole-transporting materials for organic light-emitting diodes," *Chemical Physics Letters*, vol. 439, 2007, pp. 132-137.

European Search Report issued in corresponding application, EP 11 16 0544, dated Jul. 5, 2011.

* cited by examiner

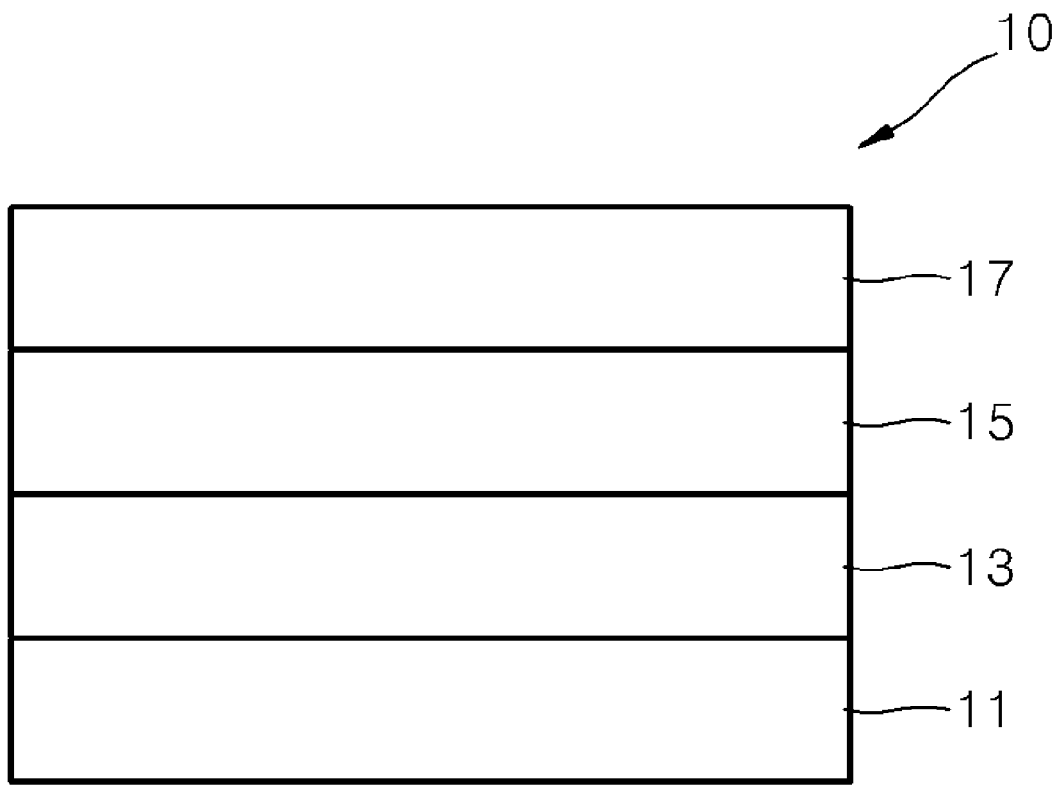

CONDENSED-CYCLIC COMPOUND AND ORGANIC LIGHT-EMITTING DEVICE INCLUDING THE SAME

BACKGROUND

1. Field

Embodiments relate to a condensed-cyclic compound and organic light-emitting devices including the same.

2. Description of the Related Art

Organic light-emitting devices (OLEDs), which are self-emitting devices, have advantages, e.g., a wide viewing angle, excellent contrast, quick response, high brightness, excellent driving voltage characteristics, and can provide multicolored images.

A typical OLED may have a structure including, e.g., a substrate, and an anode, a hole transport layer (HTL), an emission layer (EML), an electron transport layer (ETL), and a cathode, which are sequentially stacked on the substrate. In this regard, the HTL, the EML, and the ETL may be organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

It is a feature of an embodiment to provide a condensed-cyclic compound and an organic light-emitting device including the same.

At least one of the above and other features and advantages may be realized by providing a condensed-cyclic compound represented by Formula 1 below:

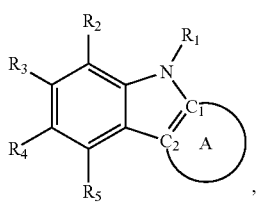

Formula 1 wherein, in Formula 1:

ring A is represented by Formula 2 below or Formula 3 below:

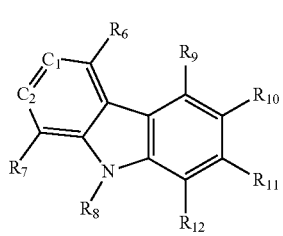

Formula 2

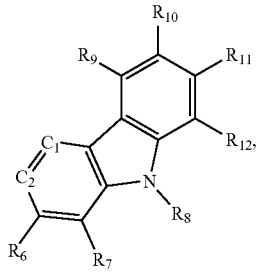

Formula 3

$R_1$ through $R_{12}$ are each independently a hydrogen atom, a heavy hydrogen atom (deuterium), a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a first substituent represented by —$(Ar_1)_a$—$Ar_{11}$, a second substituent represented by —N[—$(Ar_2)_b$—$Ar_{12}$][—$(Ar_3)_c$—$Ar_{13}$], or a third substituent represented by —$(Ar_4)_d$—N[$(Ar_5)_e$—$Ar_{15}$][—$(Ar_6)_f$—$Ar_{16}$], at least one of $R_1$ through $R_{12}$ is the third substituent;

$Ar_1$ through $Ar_6$, among the first through third substituents, are each independently a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, or a substituted or unsubstituted $C_3$-$C_{30}$ heteroarylene group;

$Ar_{11}$, $Ar_{12}$, $Ar_{13}$, $Ar_{15}$, and $Ar_{16}$, among the first to third substituents, are each independently a hydrogen atom, a halogen atom, a heavy hydrogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group or a substituted or unsubstituted $C_3$-$C_{30}$ heteroaryl group;

a, b, c, e, and f are each independently an integer of 0 to 10;
d is an integer of 1 to 10; and "a" groups of $Ar_1$ in the group of —$(Ar_1)_a$—$Ar_{11}$ of the first substituent are identical to or different from each other; "b" groups of $Ar_2$ in the group of —$(Ar_2)_b$—$Ar_{12}$ of the second substituent are identical to or different from each other; "c" groups of $Ar_3$ in the group of —$(Ar_3)_c$—$Ar_{13}$ of the second substituent are identical to or different from each other; "e" groups of $Ar_5$ in the group of —$(Ar_5)_e$—$Ar_{15}$ of the third substituent are identical to or different from each other; and "f" groups of $Ar_6$ in the group of —$(Ar_6)_f$—$Ar_{16}$ of the third substituent are identical to or different from each other.

$Ar_1$ through $Ar_6$ may each independently be a substituted or unsubstituted $C_5$-$C_{14}$ arylene group or a substituted or unsubstituted $C_3$-$C_{14}$ heteroarylene group.

$Ar_1$ through $Ar_6$ may each independently be a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$ alkyl)fluorenylene group, a ($C_6$-$C_{14}$ aryl)fluorenylene group, a di($C_6$-$C_{14}$ aryl)fluorenylene group, a naphthylene group, a $C_1$-$C_{10}$ alkylnaphthylene group, a di($C_1$-$C_{10}$ alkyl)naphthylene group, a ($C_6$-$C_{14}$ aryl)naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$ aryl)anthrylene group, a di($C_6$-$C_{14}$ aryl)anthrylene group, a pyridinylene group, a $C_1$-$C_{10}$ alkylpyridinylene group, a di($C_1$-$C_{10}$ alkyl)pyridinylene group, a ($C_6$-$C_{14}$ aryl)pyridinylene group, a di($C_6$-$C_{14}$ aryl)pyridinylene group, a quinolinylene group, a $C_1$-$C_{10}$ alkylquinolinylene group, a di($C_1$-$C_{10}$ alkyl)quinolinylene group, a ($C_6$-$C_{14}$ aryl)quinolinylene group, a di($C_6$-$C_{14}$ aryl)quinolinylene group, a benzoimidazolylene group, a $C_1$-$C_{10}$ alkylbenzoimidazolylene group, a di($C_1$-$C_{10}$ alkyl)benzoimidazolylene group, a ($C_6$-$C_{14}$ aryl)benzoimidazolylene group, a di($C_6$-$C_{14}$ aryl)benzoimidazolylene group, an imidazopyridinylene group, a $C_1$-$C_{10}$ alkylimidazopyridinylene group, a di($C_1$-$C_{10}$ alkyl)imidazopyridinylene group, a ($C_6$-$C_{14}$ aryl)imidazopyridinylene group, a di($C_6$-$C_{14}$aryl)imidazopyridinylene group, an imidazopyrimidinylene group, a $C_1$-$C_{10}$ alkylimidazopyrimidinylene group, a di($C_1$-$C_{10}$alkyl)imidazopyrimidinylene group, a ($C_6$-$C_{14}$ aryl)imidazopyrimidinylene group, or a di($C_6$-$C_{14}$ aryl)imidazopyrimidinylene group.

$Ar_{11}$, $Ar_{12}$, $Ar_{13}$, $Ar_{15}$, and $Ar_{16}$ may each independently be a hydrogen atom, a heavy hydrogen atom, a halogen atom, a hydroxyl group, a cyano group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_5$-$C_{14}$ aryl group, or a substituted or unsubstituted $C_3$-$C_{14}$ heteroaryl group.

$Ar_{11}$, $Ar_{12}$, $Ar_{13}$, $Ar_{15}$, and $Ar_{16}$ may each independently be a hydrogen atom, a heavy hydrogen atom, a halogen atom, a hydroxyl group, a cyano group, a methyl group, an ethyl group, a propyl group, a buthyl group, penthyl group, an ethenyl group, a prophenyl group, a butenyl group, a pentenyl group, an acethly group, a methoxy group, an ethoxy group, a propoxy group, a butoxy group, a pentoxy group, a phenyl group, a $C_1$-$C_{10}$alkyl phenyl group, a di($C_1$-$C_{10}$alkyl)phenyl group, a ($C_6$-$C_{14}$aryl)phenyl group, a di($C_6$-$C_{14}$aryl)phenyl group, a carbazolyl group, a $C_1$-$C_{10}$alkyl carbazolyl group, a di($C_1$-$C_{10}$alkyl) carbazolyl group, a $C_6$-$C_{14}$aryl carbazolyl group, a di($C_6$-$C_{14}$aryl) carbazolyl group, a fluorenyl group, a $C_1$-$C_{10}$alkylfluorenyl group, a di($C_1$-$C_{10}$alkyl)fluorenyl group, a ($C_6$-$C_{14}$aryl)fluorenyl group, a di($C_6$-$C_{14}$aryl)fluorenyl group, a naphthyl group, a $C_1$-$C_{10}$alkylnaphthyl group, a di($C_1$-$C_{10}$alkyl)naphthyl group, a ($C_6$-$C_{14}$aryl)naphthyl group, a di($C_6$-$C_{14}$aryl)naphthyl group, an anthryl group, a $C_1$-$C_{10}$alkylanthryl group, a di($C_1$-$C_{10}$alkyl)anthryl group, a ($C_6$-$C_{14}$aryl)anthryl group, a di($C_6$-$C_{14}$aryl)anthryl group, a pyridinyl group, a pyridinylene group, a $C_1$-$C_{10}$alkylpyridinyl group, a di($C_1$-$C_{10}$alkyl)pyridinyl group, a ($C_6$-$C_{14}$aryl)pyridinyl group, a di($C_6$-$C_{14}$aryl)pyridinyl group, a quinolinyl group, a $C_1$-$C_{10}$alkylquinolinyl group, a di($C_1$-$C_{10}$alkyl)quinolinyl group, a ($C_6$-$C_{14}$aryl)quinolinyl group, a di($C_6$-$C_{14}$aryl)quinolinyl group, a benzoimidazolyl group, a $C_1$-$C_{10}$alkylbenzoimidazolyl group, a di($C_1$-$C_{10}$alkyl)benzoimidazolyl group, a ($C_6$-$C_{14}$aryl)benzoimidazolyl group, a di($C_6$-$C_{14}$aryl)benzoimidazolyl group, an imidazopyridinyl group, a $C_1$-$C_{10}$alkylimidazopyridinyl group, a di($C_1$-$C_{10}$alkyl)imidazopyridinyl group, a ($C_6$-$C_{14}$aryl)imidazopyridinyl group, a di($C_6$-$C_{14}$aryl) imidazopyridinyl group, an imidazopyrimidinyl group, a $C_1$-$C_{10}$alkylimidazopyrimidinyl group, a di($C_1$-$C_{10}$alkyl) imidazopyrimidinyl group, a ($C_6$-$C_{14}$aryl)imidazopyrimidinyl group, or a di($C_6$-$C_{14}$ aryl) imidazopyrimidinyl group.

$Ar_{11}$, $Ar_{12}$, $Ar_{13}$, $Ar_{15}$, and $Ar_{16}$ may each independently be represented by any one of Formulae 4A through 4G below:

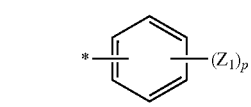

Formula 4A

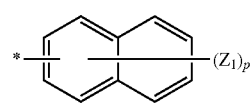

Formula 4B

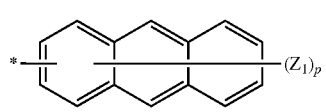

Formula 4C

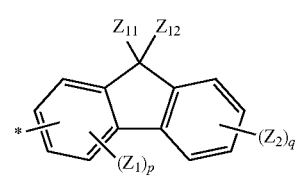

Formula 4D

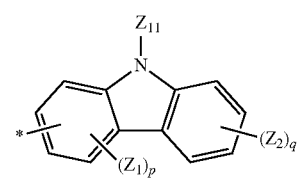

Formula 4E

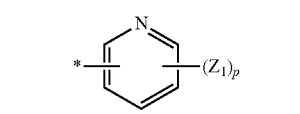

Formula 4F

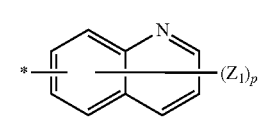

Formula 4G and wherein, in Formulae 4A to 4G $Z_1$, $Z_2$, $Z_{11}$, and $Z_{12}$ are each independently a hydrogen atom, a heavy hydrogen atom, a $C_1$-$C_{10}$alkyl group, a $C_1$-$C_{10}$ alkoxy group, or a $C_6$-$C_{14}$ aryl group, p and q are each independently an integer of 1 to 8, and * is a bonding site with $Ar_1$, $Ar_2$, $Ar_3$, $Ar_5$, or $Ar_6$.

$Ar_{11}$, $Ar_{12}$, $Ar_{13}$, $Ar_{15}$, and $Ar_{16}$ may each independently be represented by any one of Formula 5A through 5E below:

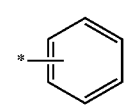

Formula 5A

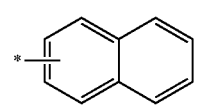

Formula 5B

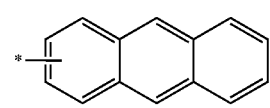

Formula 5C

Formula 5D
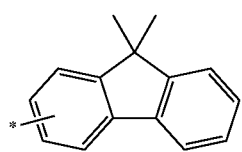
Formula 5E
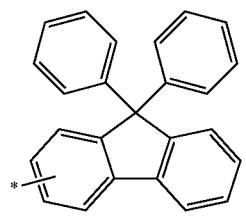
and wherein, in Formulae 5A to 5E, * is a bonding site with $Ar_1$, $Ar_2$, $Ar_3$, $Ar_5$, or $Ar_6$.
a, b, c, e, and f may each independently be 0, 1, 2, or 3, and d is 1, 2, or 3.
The second substituent and $-N[-(Ar_5)_e-Ar_{15}][-(Ar_6)_f-Ar_{16}]$ of the third substituent may each independently be represented by any one of Formulae 6A through 6K below:
Formula 6A
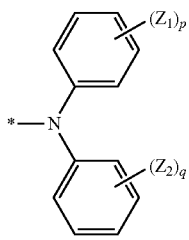
Formula 6B
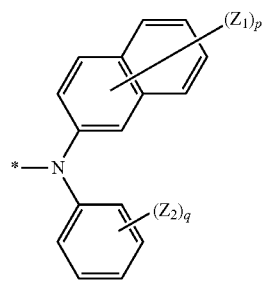
Formula 6C
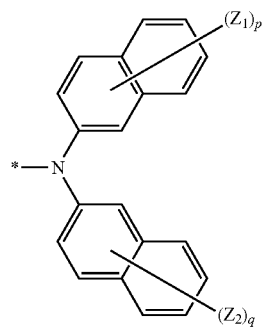
Formula 6D
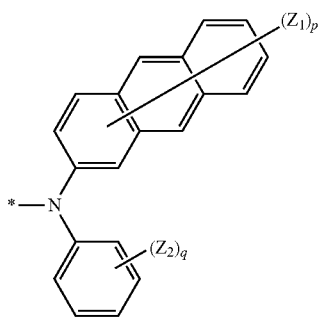
Formula 6E
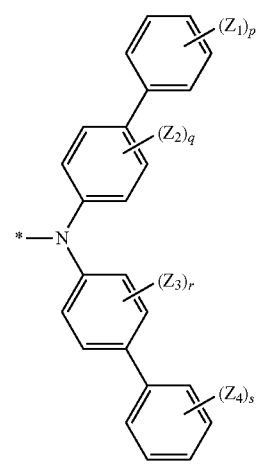
Formula 6F
Formula 6G
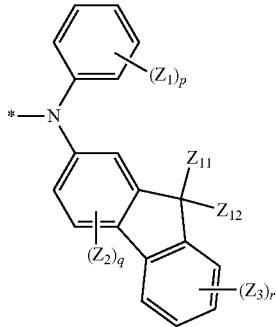

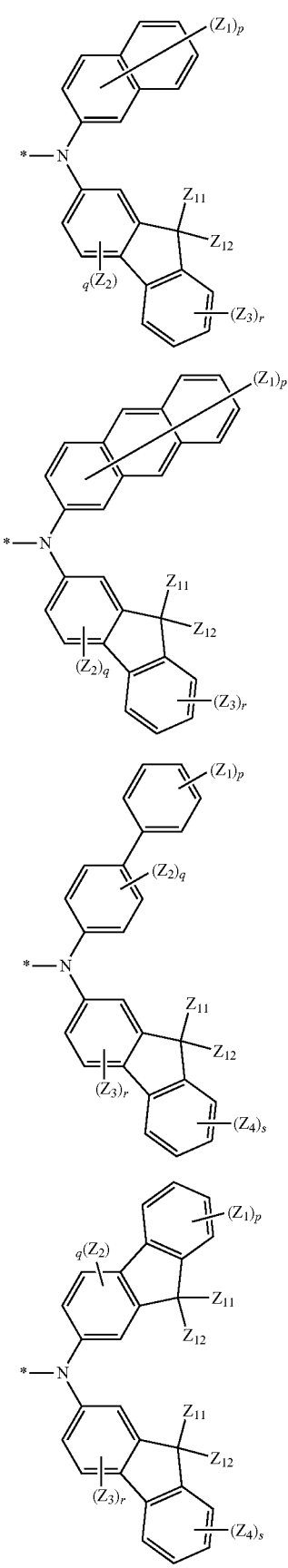

and wherein, in Formulae 6A to 6K $Z_1$ through $Z_4$ and $Z_{11}$ through $Z_{14}$ are each independently a hydrogen atom, a heavy hydrogen atom, a $C_1$-$C_{10}$ alkyl group, a $C_1$-$C_{10}$ alkoxy group, or a $C_6$-$C_{14}$ aryl group, p, q, r, and s are each independently an integer of 1 to 8, and * is a bonding site with $Ar_4$ or with a ring atom constituting a backbone of Formula 1.

$R_1$ through $R_{12}$ may each independently be a hydrogen atom, a heavy hydrogen atom, a halogen atom, a hydroxyl group, a cyano group, the first substituent, the second substituent, or the third substituent; "a" in the first substituent is 0; "b" and "c" in the second substituent are each 0 or 1; d in the third substituent is 1 or 2, and e and f in the third substituent are each independently 0 or 1; $Ar_2$ through $Ar_6$, among the first substituent through the third substituent, are each independently a substituted or unsubstituted $C_5$-$C_{14}$ arylene group or a substituted or unsubstituted $C_3$-$C_{14}$ heteroarylene group; and $Ar_{11}$, $Ar_{12}$, $Ar_{13}$, $Ar_{15}$, and $Ar_{16}$, among the first substituent through the third substituent, are each independently a hydrogen atom, a heavy hydrogen atom, a halogen atom, a hydroxyl group, a cyano group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_5$-$C_{14}$ aryl group, or a substituted or unsubstituted $C_3$-$C_{14}$ heteroaryl group.

$R_1$ through $R_{12}$ may each independently be a hydrogen atom, a heavy hydrogen atom, a halogen atom, a hydroxyl group, a cyano group, the first substituent, the second substituent, or the third substituent; "a" in the first substituent is 0; "b" and "c" in the second substituent are each independently 0 or 1; "d" of the third substituent is 1 or 2, and "e" and "f" in the third substituent are each independently 0 or 1; $Ar_2$ through $Ar_6$, among the first substituent through the third substituent, are each independently a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$ alkyl)fluorenylene group, a ($C_6$-$C_{14}$ aryl)fluorenylene group, a di($C_6$-$C_{14}$ aryl)fluorenylene group, a naphthylene group, a $C_1$-$C_{10}$ alkylnaphthylene group, a di($C_1$-$C_{10}$ alkyl)naphthylene group, a ($C_6$-$C_{14}$ aryl)naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$ aryl)anthrylene group, a di($C_6$-$C_{14}$ aryl)anthrylene group, a pyridinylene group, a $C_1$-$C_{10}$ alkylpyridinylene group, a di($C_1$-$C_{10}$ alkyl)pyridinylene group, a ($C_6$-$C_{14}$ aryl)pyridinylene group, a di($C_6$-$C_{14}$ aryl)pyridinylene group, a quinolinylene group, a $C_1$-$C_{10}$ alkyl quinolinylene group, a di($C_1$-$C_{10}$ alkyl)quinolinylene group, a ($C_6$-$C_{14}$ aryl)quinolinylene group, a di($C_6$-$C_{14}$ aryl) quinolinylene group, a benzoimidazolylene group, a $C_1$-$C_{10}$ alkylbenzoimidazolylene group, a di($C_1$-$C_{10}$ alkyl)benzoimidazolylene group, a ($C_6$-$C_{14}$ aryl)benzoimidazolylene group, a di($C_6$-$C_{14}$ aryl)benzoimidazolylene group, an imidazopyridinylene group, a $C_1$-$C_{10}$ alkylimidazopyridinylene group, a di($C_1$-$C_{10}$ alkyl)imidazopyridinylene group, a ($C_6$-$C_{14}$ aryl) imidazopyridinylene group, a di($C_6$-$C_{14}$ aryl)imidazopyridinylene group, an imidazopyrimidinylene group, a $C_1$-$C_{10}$ alkylimidazopyrimidinylene group, a di($C_1$-$C_{10}$ alkyl) imidazopyrimidinylene group, a ($C_6$-$C_{14}$ aryl)imidazopyrimidinylene group, or a di($C_6$-$C_{14}$ aryl)imidazopyrimidinylene group; $Ar_{11}$, $Ar_{12}$, $Ar_{13}$, $Ar_{15}$, and $Ar_{16}$, among the first substituent through the third substituent, are each independently a hydrogen atom, a heavy hydrogen atom, a halogen atom, a hydroxyl group, a cyano group, a methyl group, an ethyl group, a propyl group, a butyl group, pentyl group, an ethenyl group, a propenyl group, a butenyl group, a pentenyl group, an acetyl group, a methoxy group, an ethoxy group, a propoxy group, a butoxy group, a pentoxy group, a phenyl group, a $C_1$-$C_{10}$ alkylphenyl group, a di($C_1$-$C_{10}$ alkyl)phenyl group, a ($C_6$-$C_{14}$ aryl)phenyl group, a di($C_6$-$C_{14}$ aryl)phenyl group, a carbazolyl group, a $C_1$-$C_{10}$ alkyl carbazolyl group, a di($C_1$-$C_{10}$ alkyl)carbazolyl group, a $C_6$-$C_{14}$ arylcarbazolyl group, a di($C_6$-$C_{14}$ aryl)carbazolyl group, a fluorenyl group, a $C_1$-$C_{10}$ alkylfluorenyl group, a di($C_1$-$C_{10}$ alkyl)fluorenyl group, a ($C_6$-$C_{14}$ aryl)fluorenyl group, a di($C_6$-$C_{14}$ aryl)fluorenyl group, a naphthyl group, a $C_1$-$C_{10}$ alkylnaphthyl group, a di($C_1$-$C_{10}$ alkyl)naphthyl group, a ($C_6$-$C_{14}$ aryl)naphthyl group, a di($C_6$-$C_{14}$ aryl)naphthyl group, an anthryl group, a $C_1$-$C_{10}$ alkylanthryl group, a di($C_1$-$C_{10}$ alkyl)anthryl group, a ($C_6$-$C_{14}$ aryl)anthryl group, a di($C_6$-$C_{14}$ aryl)anthryl group, a pyridinyl group, a $C_1$-$C_{10}$ alkylpyridinyl group, a di($C_1$-$C_{10}$ alkyl)pyridinyl group, a ($C_6$-$C_{14}$ aryl)pyridinyl group, a di($C_6$-$C_{14}$ aryl)pyridinyl group, a quinolinyl group, a $C_1$-$C_{10}$ alkylquinolinyl group, a di($C_1$-$C_{10}$ alkyl)quinolinyl group, a ($C_6$-$C_{14}$ aryl)quinolinyl group, a di($C_6$-$C_{14}$ aryl)quinolinyl group, a benzoimidazolyl group, a $C_1$-$C_{10}$ alkylbenzoimidazolyl group, a di($C_1$-$C_{10}$ alkyl)benzoimidazolyl group, a ($C_6$-$C_{14}$ aryl)benzoimidazolyl group, a di($C_6$-$C_{14}$ aryl)benzoimidazolyl group, an imidazopyridinyl group, a $C_1$-$C_{10}$ alkylimidazopyridinyl group, a di($C_1$-$C_{10}$ alkyl)imidazopyridinyl group, a ($C_6$-$C_{14}$ aryl)imidazopyridinyl group, a di($C_6$-$C_{14}$ aryl)imidazopyridinyl group, an imidazopyrimidinyl group, a $C_1$-$C_{10}$ alkylimidazopyrimidinyl group, a di($C_1$-$C_{10}$ alkyl)imidazopyrimidinyl group, a ($C_6$-$C_{14}$ aryl)imidazopyrimidinyl group, or a di($C_6$-$C_{14}$ aryl)imidazopyrimidinyl group.

The condensed-cyclic compound represented by Formula 1 may be represented by any one of Formulae 2a through 2d below:

Formula 2a
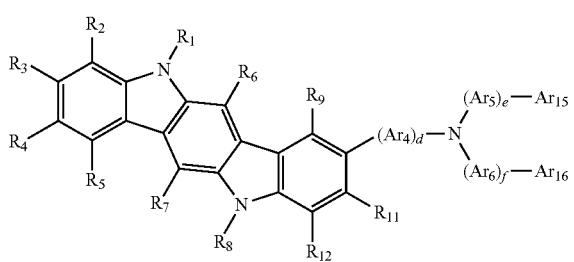

Formula 2b
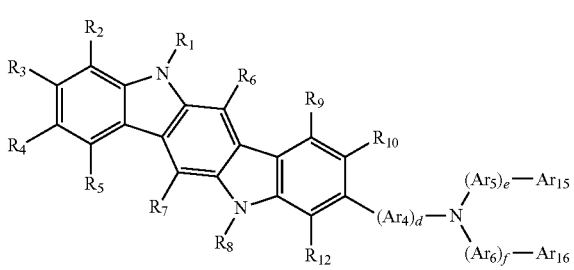

Formula 2c
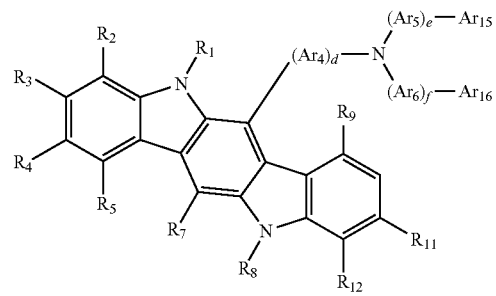

Formula 2d
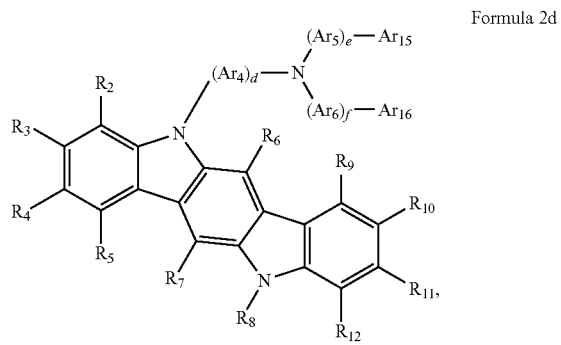

wherein, in Formulae 2a to 2d $R_1$ through $R_{12}$ are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, the first substituent, the second substituent, or the third substituent; $Ar_1$ through $Ar_6$, among the first to third substituents, are each independently a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, or a substituted or unsubstituted $C_3$-$C_{30}$ heteroarylene group; $Ar_{11}$, $Ar_{12}$, $Ar_{13}$, $Ar_{15}$, and $Ar_{16}$, among the first to third substituents, are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, or a substituted or unsubstituted $C_3$-$C_{30}$ heteroaryl group; a, b, c, e, and f are each independently an integer of 0 to 10; d is an integer of 1 to 10; and "a" groups of $Ar_1$ in the group of —$(Ar_1)_a$—$Ar_{11}$ of the first substituent are identical to or different from each other; "b" groups of $Ar_2$ in the group of —$(Ar_2)_b$—$Ar_{12}$ of the second substituent are identical to or different from each other; "c" groups of $Ar_3$ in the group of —$(Ar_3)_c$—$Ar_{13}$ of the second substituent are identical to or different from each other; "e" groups of $Ar_5$ in the group of —$(Ar_5)_e$—$Ar_{15}$ of the third substituent are identical to or different from each other; and "f" groups of $Ar_6$ in the group of —$(Ar_6)_f$—$Ar_{16}$ of the third substituent are identical to or different from each other.

$Ar_4$ may include at least one of a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$ alkyl)fluorenylene group, a ($C_6$-$C_{14}$ aryl)fluorenylene group, a di($C_6$-$C_{14}$ aryl)fluorenylene group, a naphthylene group, a $C_1$-$C_{10}$ alkylnaphthylene group, a di($C_1$-$C_{10}$ alkyl)naphthylene group, a ($C_6$-$C_{14}$ aryl)naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$ aryl)anthrylene group, and a di($C_6$-$C_{14}$ aryl)anthrylene group; and d may be 1, 2, or 3.

The second substituent and $-N[-(Ar_5)_e-Ar_{15}][-(Ar_6)_f-Ar_{16}]$ of the third substituent may each independently be represented by any one of Formulae 6A through 6K below:

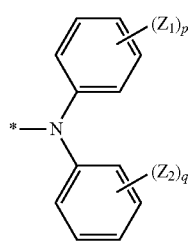

Formula 6A

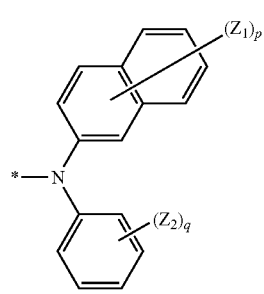

Formula 6B

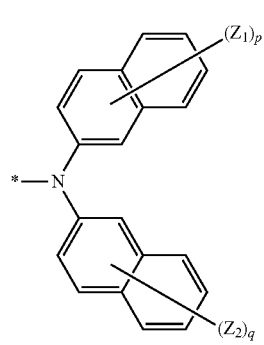

Formula 6C

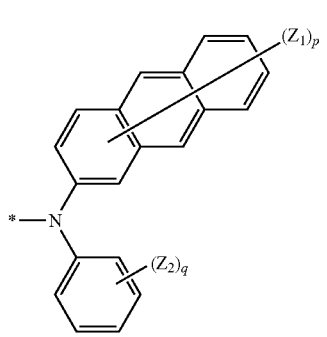

Formula 6D

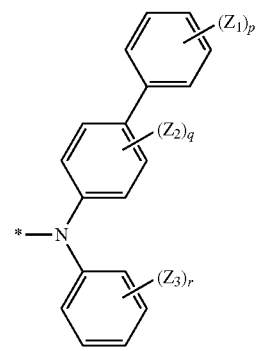

Formula 6E

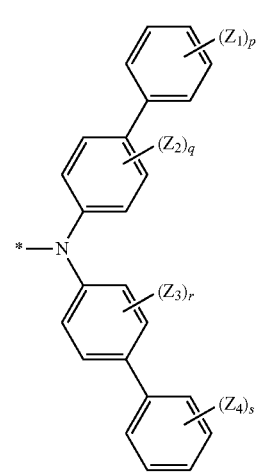

Formula 6F

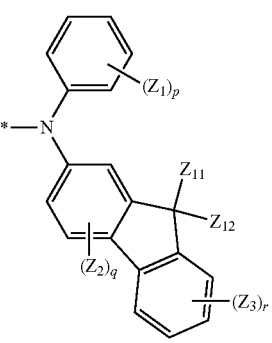

Formula 6G

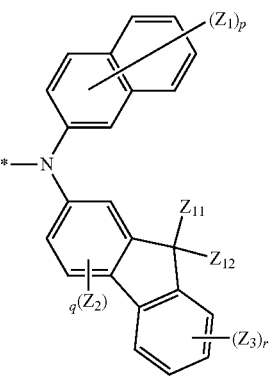

Formula 6H

-continued

Formula 6I
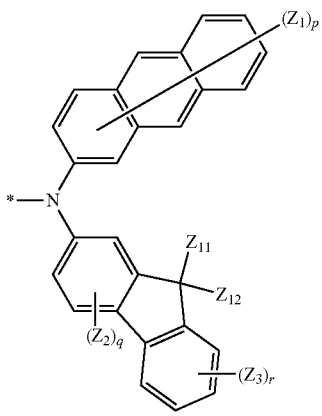

Formula 6J
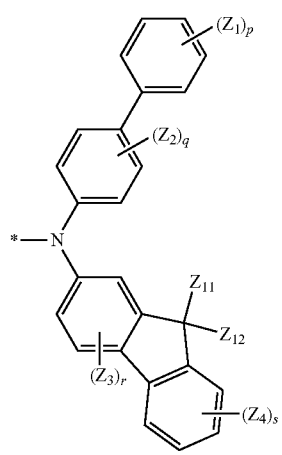

Formula 6K
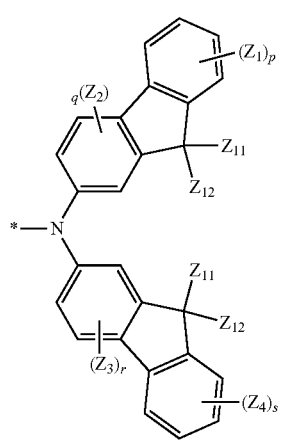

and in Formulae 6A to 6K $Z_1$ through $Z_4$ and $Z_{11}$ through $Z_{14}$ are each independently a hydrogen atom, a heavy hydrogen atom, a $C_1$-$C_{10}$ alkyl group, a $C_1$-$C_{10}$ alkoxy group, or a $C_6$-$C_{14}$ aryl group, p, q, r, and s are each independently an integer of 1 to 8, and * is a bonding site with $Ar_4$ or with a ring atom constituting a backbone of Formula 1.

The condensed-cyclic compound represented by Formula 1 may be represented by any one of Formulae 3a through 3e below:

Formula 3a
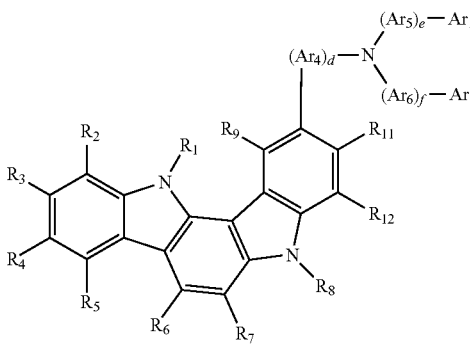

Formula 3b
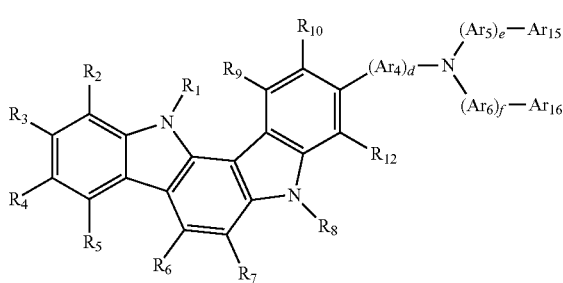

Formula 3c
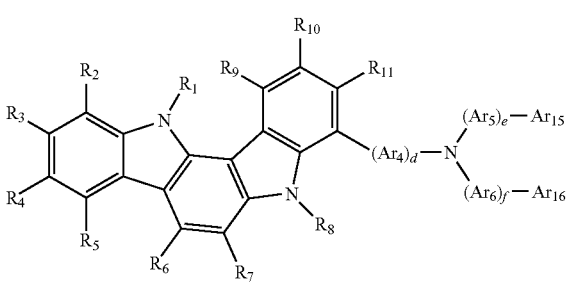

Formula 3d
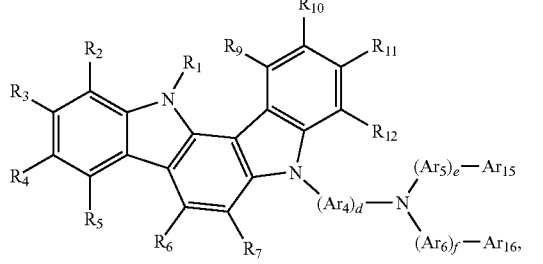

Formula 3e
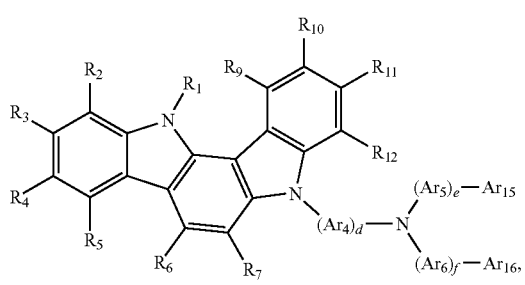

wherein, in Formulae 3a to 3e $R_1$ through $R_{12}$ are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, the first substituent, the second substituent, or the third substituent; $Ar_1$ through $Ar_6$, among the first to third substituents, are each independently a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, or a substituted or unsubstituted $C_3$-$C_{30}$ heteroarylene group; $Ar_{11}$, $Ar_{12}$, $Ar_{13}$, $Ar_{15}$, and $Ar_{16}$ are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, or a substituted or unsubstituted $C_3$-$C_{30}$ heteroaryl group; a, b, c, e, and f are each independently an integer of 0 to 10; d is an integer of 1 to 10; "a" groups of $Ar_1$ in the group of —$(Ar_1)_a$—$Ar_{11}$ of the first substituent are identical to or different from each other; "b" groups of $Ar_2$ in the group of —$(Ar_2)_b$—$Ar_{12}$ of the second substituent are identical to or different from each other; "c" groups of $Ar_3$ in the group of —$(Ar_3)_c$—$Ar_{13}$ of the second substituent are identical to or different from each other; "e" groups of $Ar_5$ in the group of —$(Ar_5)_e$—$Ar_{15}$ of the third substituent are identical to or different from each other; and "f" groups of $Ar_6$ in the group of —$(Ar_6)_f$—$Ar_{16}$ of the third substituent are identical to or different from each other.

$Ar_4$ may include at least one of a phenylene group, a $C_1$-$C_{10}$ alkylphenylene group, a di($C_1$-$C_{10}$alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$alkyl)fluorenylene group, a ($C_6$-$C_{14}$ aryl)fluorenylene group, a di($C_6$-$C_{14}$ aryl)fluorenylene group, a naphthylene group, a $C_1$-$C_{10}$ alkylnaphthylene group, a di($C_1$-$C_{10}$alkyl)naphthylene group, a ($C_6$-$C_{14}$ aryl)naphthylene group, a di($C_6$-$C_{14}$ aryl)naphthylene group, an anthrylene group, a $C_1$-$C_{10}$alkylanthrylene group, a di($C_1$-$C_{10}$alkyl)anthrylene group, a ($C_6$-$C_{14}$ aryl)anthrylene group, and a di($C_6$-$C_{14}$ aryl)anthrylene group; and d may be 1, 2, or 3.

The second substituent and —N[—$(Ar_5)_e$—$Ar_{15}$][—$(Ar_6)_f$—$Ar_{16}$] of the third substituent and may each independently be represented by any one of Formulae 6A through 6K below:

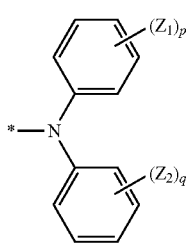

Formula 6A

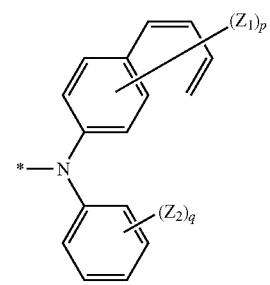

Formula 6B

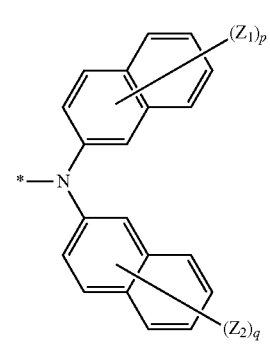

Formula 6C

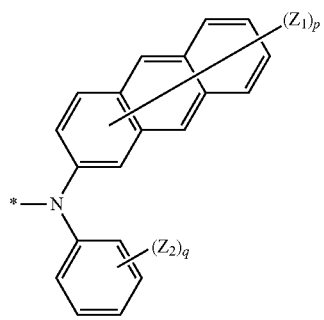

Formula 6D

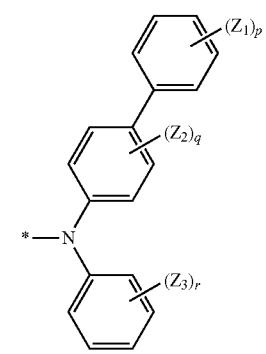

Formula 6E

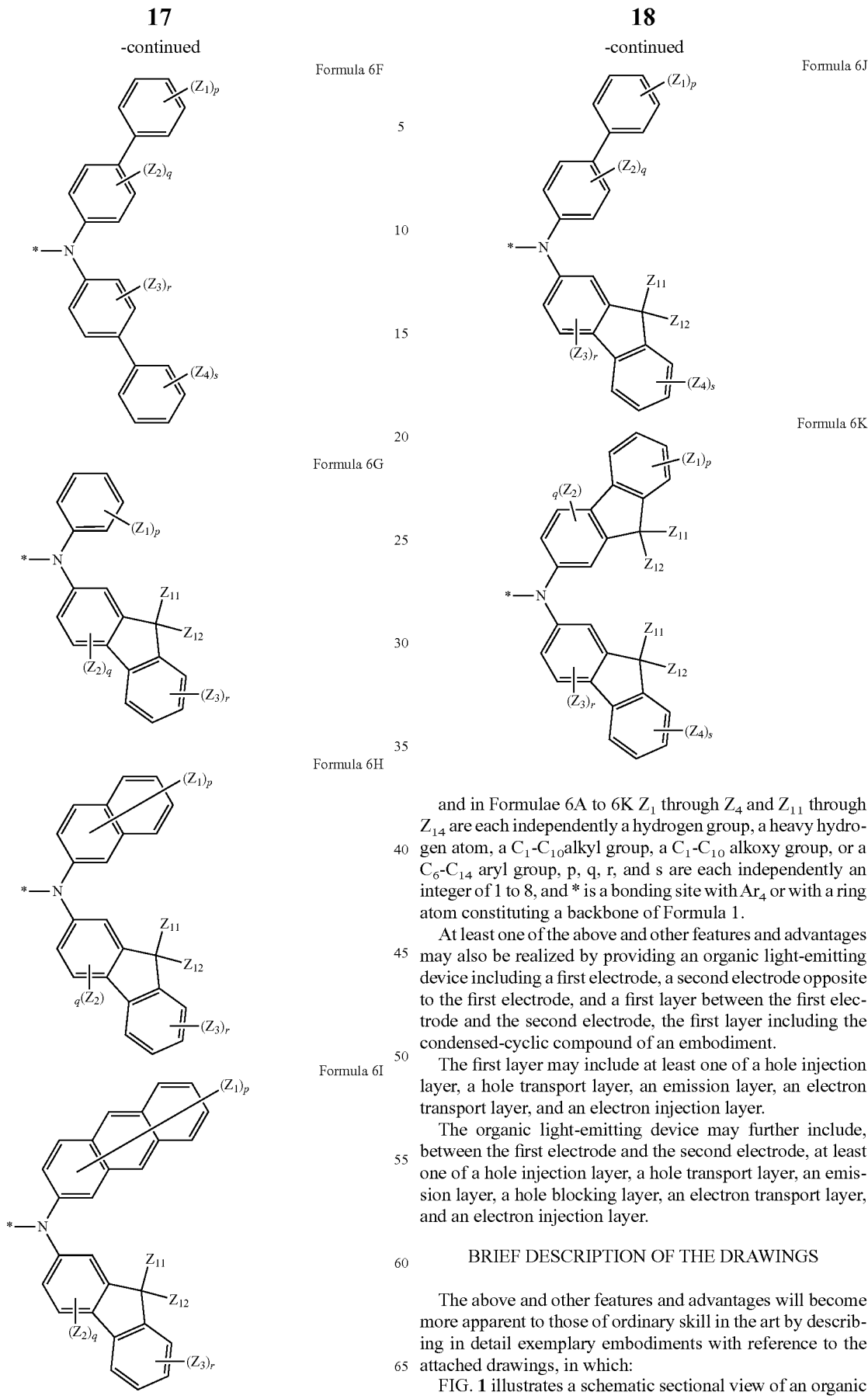

and in Formulae 6A to 6K $Z_1$ through $Z_4$ and $Z_{11}$ through $Z_{14}$ are each independently a hydrogen group, a heavy hydrogen atom, a $C_1$-$C_{10}$ alkyl group, a $C_1$-$C_{10}$ alkoxy group, or a $C_6$-$C_{14}$ aryl group, p, q, r, and s are each independently an integer of 1 to 8, and * is a bonding site with $Ar_4$ or with a ring atom constituting a backbone of Formula 1.

At least one of the above and other features and advantages may also be realized by providing an organic light-emitting device including a first electrode, a second electrode opposite to the first electrode, and a first layer between the first electrode and the second electrode, the first layer including the condensed-cyclic compound of an embodiment.

The first layer may include at least one of a hole injection layer, a hole transport layer, an emission layer, an electron transport layer, and an electron injection layer.

The organic light-emitting device may further include, between the first electrode and the second electrode, at least one of a hole injection layer, a hole transport layer, an emission layer, a hole blocking layer, an electron transport layer, and an electron injection layer.

BRIEF DESCRIPTION OF THE DRAWINGS

The above and other features and advantages will become more apparent to those of ordinary skill in the art by describing in detail exemplary embodiments with reference to the attached drawings, in which:

FIG. 1 illustrates a schematic sectional view of an organic light-emitting diode (OLED) according to an embodiment.

DETAILED DESCRIPTION

Korean Patent Application No. 10-2010-0029992, filed on Apr. 1, 2010, in the Korean Intellectual Property Office, and entitled: "Condensed-Cyclic Compound and Organic Light-Emitting Device Including the Same," and Korean Patent Application No. 10-2011-0028212, filed on Mar. 29, 2011, in the Korean Intellectual Property Office, and entitled: "Condensed-Cyclic Compound and Organic Light-Emitting Device Including the Same," are incorporated by reference herein in their entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

A condensed-cyclic compound according to an embodiment is represented by Formula 1 below:

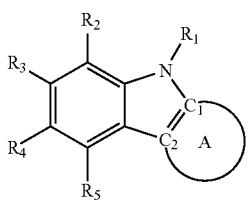

Formula 1

In Formula 1, a ring A is represented by Formula 2 below or Formula 3 below:

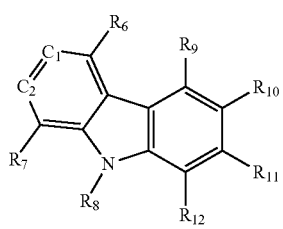

Formula 2

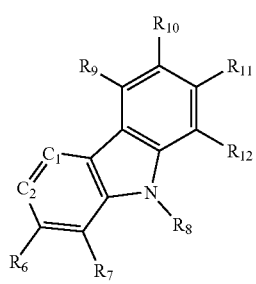

Formula 3

In Formula 1, $C_1$ is the same carbon as $C_1$ in Formula 2 and $C_1$ in Formula 3. In addition, in Formula 1, $C_2$ is the same carbon as $C_2$ in Formula 2 and $C_2$ in Formula 3. In Formulae 1, 2, and 3, $R_1$ through $R_{12}$ may each independently be, e.g., a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a first substituent represented by —$(Ar_1)_a$—$Ar_{11}$, a second substituent represented by —N[—$(Ar_2)_b$—$Ar_{12}$][—$(Ar_3)_c$—$Ar_{13}$], and/or a third substituent represented by —$(Ar_4)_d$—N[$Ar_5)_e$—$Ar_{15}$][—$(Ar_6)_f$—$Ar_{16}$], wherein at least one of $R_1$ through $R_{12}$ is —$(Ar_4)_d$—N[—$(Ar_5)_e$—$Ar_{15}$][—$(Ar_6)_f$—$Ar_{16}$], that is, the third substituent;

$Ar_1$ through $Ar_6$, among the first to third substituents, may each independently be, e.g., a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and/or a substituted or unsubstituted $C_3$-$C_{30}$ heteroarylene group. For example, $Ar_1$ to $Ar_6$ may each independently be a substituted or unsubstituted $C_5$-$C_{14}$ arylene group and/or a substituted or unsubstituted $C_3$-$C_{14}$ heteroarylene group, but are not limited thereto. In an implementation, $Ar_1$ to $Ar_6$ may each independently be a substituted or unsubstituted $C_6$-$C_{14}$ arylene group.

For example, $Ar_1$ through $Ar_6$, among the first to third substituents, may each independently be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, and/or a substituted or unsubstituted isoxazolylene group, but are not limited thereto.

For example, $Ar_1$ to $Ar_6$ may each independently be a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$ alkyl)fluorenylene group, a ($C_6$-$C_{14}$ aryl)fluorenylene group, a di($C_6$-$C_{14}$ aryl) fluorenylene group, a naphthylene group, a $C_1$-$C_{10}$ alkylnaphthylene group, a di($C_1$-$C_{10}$ alkyl)naphthylene group, a ($C_6$-$C_{14}$ aryl)naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$ aryl) anthrylene group, a di($C_6$-$C_{14}$ aryl)anthrylene group, a pyridinylene group, a $C_1$-$C_{10}$ alkylpyridinylene group, a di($C_1$-$C_{10}$ alkyl)pyridinylene group, a ($C_6$-$C_{14}$ aryl)pyridinylene group, a di($C_6$-$C_{14}$ aryl)pyridinylene group, a quinolinylene group, a $C_1$-$C_{10}$ alkylquinolinylene group, a di($C_1$-$C_{10}$ alkyl)quinolinylene group, a ($C_6$-$C_{14}$ aryl)quinolinylene group, a di($C_6$-$C_{14}$ aryl)quinolinylene group, a benzoimidazolylene group, a $C_1$-$C_{10}$ alkylbenzoimidazolylene group, a di($C_1$-$C_{10}$ alkyl)benzoimidazolylene group, a ($C_6$-$C_{14}$ aryl) benzoimidazolylene group, a di($C_6$-$C_{14}$ aryl)benzoimidazolylene group, an imidazopyridinylene group, a $C_1$-$C_{10}$ alkylimidazopyridinylene group, a di($C_1$-$C_{10}$ alkyl)imidazopyridinylene group, a ($C_6$-$C_{14}$ aryl)imidazopyridinylene group, a di($C_6$-$C_{14}$aryl)imidazopyridinylene group, an imidazopyrimidinylene group, a $C_1$-$C_{10}$ alkylimidazopyrimidinylene group, a di($C_1$-$C_{10}$ alkyl)imidazopyrimidinylene group, a ($C_6$-$C_{14}$ aryl)imidazopyrimidinylene group, and/or a di($C_6$-$C_{14}$ aryl)imidazopyrimidinylene group, but are not limited thereto.

For example, $Ar_{11}$, $Ar_{12}$, $Ar_{13}$, $Ar_{15}$, and $Ar_{16}$, among the first to third substituents, may each independently be a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group and a substituted or unsubstituted $C_3$-$C_{30}$ heteroaryl group. For example, $Ar_{11}$, $Ar_{12}$, $Ar_{13}$, $Ar_{15}$, and $Ar_{16}$ may each independently be a hydrogen atom, a heavy hydrogen atom, a halogen atom, a hydroxyl group, a cyano group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_5$-$C_{14}$ aryl group, and/or a substituted or unsubstituted $C_3$-$C_{14}$ heteroaryl group, but are not limited thereto. In an implementation, $Ar_{11}$, $Ar_{12}$, $Ar_{13}$, $Ar_{15}$, and $Ar_{16}$, among the first to third substituents may each independently be a substituted or unsubstituted $C_6$-$C_{30}$ aryl group.

For example, $Ar_{11}$, $Ar_{12}$, $Ar_{13}$, $Ar_{15}$, and $Ar_{16}$ may each independently be a hydrogen atom, a heavy hydrogen atom, a halogen atom, a hydroxyl group, a cyano group, a methyl group, an ethyl group, a propyl group, a buthyl group, a penthyl group, an ethenyl group, a prophenyl group, a butenyl group, a pentenyl group, an acethly group, a methoxy group, an ethoxy group, a propoxy group, a butoxy group, a pentoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthracenyl group, a substituted or unsubstituted fluoranthenyl group, a substituted or unsubstituted triphenylenyl group, a substituted or unsubstituted pyrenylenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, and/or a substituted or unsubstituted isoxazolyl group, but are not limited thereto.

For example, $Ar_{11}$, $Ar_{12}$, $Ar_{13}$, $Ar_{15}$, and $Ar_{16}$ may each independently be a hydrogen atom, a heavy hydrogen atom, a halogen atom, a hydroxyl group, a cyano group, a methyl group, an ethyl group, a propyl group, a buthyl group, penthyl group, an ethenyl group, a prophenyl group, a butenyl group, a pentenyl group, an acethly group, a methoxy group, an ethoxy group, a propoxy group, a butoxy group, a pentoxy group, a phenyl group, a $C_1$-$C_{10}$ alkyl phenyl group, a di($C_1$-$C_{10}$ alkyl)phenyl group, a ($C_6$-$C_{14}$ aryl)phenyl group, a di($C_6$-$C_{14}$ aryl)phenyl group, a carbazolyl group, a $C_1$-$C_{10}$ alkyl carbazolyl group, a di($C_1$-$C_{10}$ alkyl)carbazolyl group, a $C_6$-$C_{14}$aryl carbazolyl group, a di($C_6$-$C_{14}$ aryl)carbazolyl group, a fluorenyl group, a $C_1$-$C_{10}$ alkyl fluorenyl group, a di($C_1$-$C_{10}$ alkyl)fluorenyl group, a ($C_6$-$C_{14}$ aryl)fluorenyl group, a di($C_6$-$C_{14}$ aryl)fluorenyl group, a naphthyl group, a $C_1$-$C_{10}$ alkyl naphthyl group, a di($C_1$-$C_{10}$ alkyl)naphthyl group, a ($C_6$-$C_{14}$ aryl)naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a ($C_6$-$C_{14}$ aryl)anthryl group, a di($C_6$-$C_{14}$ aryl)anthryl group, a pyridinyl group, a quinolinylene group, a $C_1$-$C_{10}$ alkyl pyridinyl group, a di($C_1$-$C_{10}$ alkyl)pyridinyl group, a ($C_6$-$C_{14}$ aryl)pyridinyl group, a di($C_6$-$C_{14}$ aryl)pyridinyl group, a quinolinyl group, a $C_1$-$C_{10}$ alkyl quinolinyl group, a di($C_1$-$C_{10}$ alkyl)quinolinyl group, a ($C_6$-$C_{14}$ aryl)quinolinyl group, a di($C_6$-$C_{14}$ aryl)quinolinyl group, a benzoimidazolyl group, a $C_1$-$C_{10}$ alkyl benzoimidazolyl group, a di($C_1$-$C_{10}$ alkyl)benzoimidazolyl group, a ($C_6$-$C_{14}$ aryl)benzoimidazolyl group, a di($C_6$-$C_{14}$ aryl)benzoimidazolyl group, an imidazopyridinyl group, a $C_1$-$C_{10}$ alkyl imidazopyridinyl group, a di($C_1$-$C_{10}$ alkyl)imidazopyridinyl group, a ($C_6$-$C_{14}$ aryl)imidazopyridinyl group, a di($C_6$-$C_{14}$ aryl)imidazopyridinyl group, an imidazopyrimidinyl group, a $C_1$-$C_{10}$ alkyl imidazopyrimidinyl group, a di($C_1$-$C_{10}$ alkyl) imidazopyrimidinyl group, a ($C_6$-$C_{14}$ aryl) imidazopyrimidinyl group, and/or a di($C_6$-$C_{14}$ aryl) imidazopyrimidinyl group. Examples of the $C_1$-$C_{10}$ alkyl group may include a methyl group, an ethyl group, a propyl group, a butyl group, and a pentyl group, and examples of the $C_5$-$C_{14}$ aryl group may include a phenyl group, a naphthyl group, and an anthryl group, but are not limited thereto.

For example, $Ar_{11}$, $Ar_{12}$, $Ar_{13}$, $Ar_{15}$, and $Ar_{16}$ may each independently be represented by any one of Formulae 4A through 4G below, but are not limited thereto:

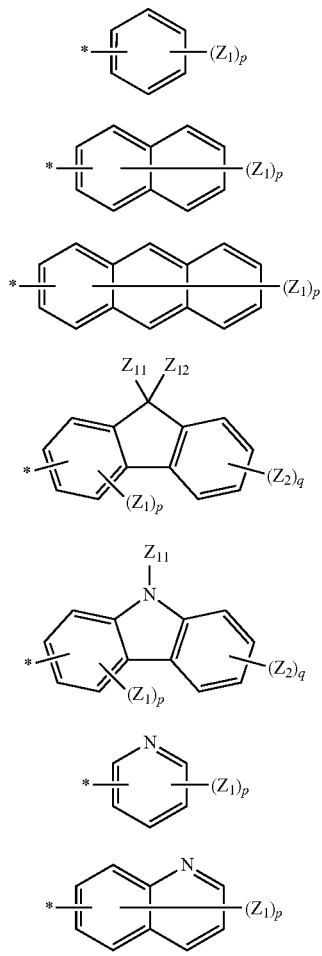

In Formulae 4A through 4G, $Z_1$, $Z_2$, $Z_{11}$ and $Z_{12}$ may each independently be, e.g., a hydrogen atom, a heavy hydrogen atom, a $C_1$-$C_{10}$ alkyl group, a $C_1$-$C_{10}$ alkoxy group, and/or a $C_6$-$C_{14}$ aryl group, p and q may each independently be an integer of 1 to 8, and * is a binding site with $Ar_1$, $Ar_2$, $Ar_3$, $Ar_5$, or $Ar_6$. When a in the first substituent is 0, $Ar_{11}$ may be represented by any one of Formulae 4A through 4G, * in Formulae 4A through 4G is a binding site with one of the ring atoms constituting a backbone of Formula 1, which is easily understood by one of ordinary skill in the art.

For example, $Z_1$, $Z_2$, $Z_{11}$ and $Z_{12}$ may each independently be a hydrogen atom, a heavy hydrogen atom, a methyl group, an ethyl group, a propyl group, a butyl group, a methoxy group, an ethoxy group, a propoxy group, a phenyl group, a naphthyl group, and/or an anthryl group.

For example, $Ar_{11}$, $Ar_{12}$, $Ar_{13}$, $Ar_{15}$, and $Ar_{16}$ may each independently be represented by one of Formulae 5A through 5E below, but are not limited thereto:

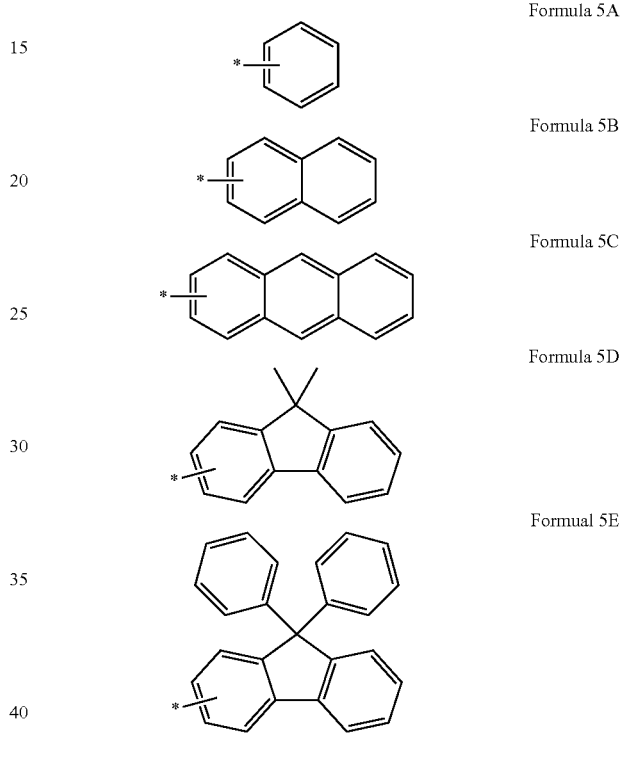

In Formulae 5A to 5E, * is a binding site with $Ar_1$, $Ar_2$, $Ar_3$, $Ar_5$, or $Ar_6$.

For example, when a in the first substituent is 0, and $Ar_{11}$ is represented by any one of Formulae 5A through 5E, * in Formulae 5A through 5E is a binding site with one of the ring atoms constituting a backbone of Formula 1, which is easily understood by one of ordinary skill in the art.

a, b, c, e, and f may each independently be an integer of 0 to 10. For example, a, b, c, e, and f may each independently be 0, 1, 2, or 3, but are not limited thereto.

For example, when a=0, the first substituent may be $Ar_{11}$, and $Ar_{11}$ may be connected directly to a ring atom constituting a backbone of Formula 1. When a=0, the first substituent may be, e.g., a substituted or unsubstituted $C_5$-$C_{30}$ aryl group or a substituted or unsubstituted $C_3$-$C_{30}$ hetero aryl group.

For example, when b=0, $Ar_{12}$ in the second substituent may be connected directly to N, like in a case when c, e, and f=0.

d may be an integer of 1 to 10. For example, d may be 1, 2, or 3, but is not limited thereto.

The second substituent and —N[—$(Ar_5)_e$—$Ar_{15}$][—$(Ar_6)_f$—$Ar_{16}$] of the third substituent may each independently be represented by one of Formulae 6A through 6K below:

Formula 6A
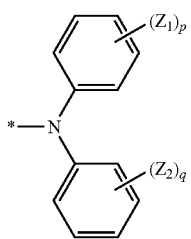
Formula 6B
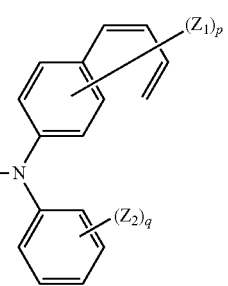
Formula 6C
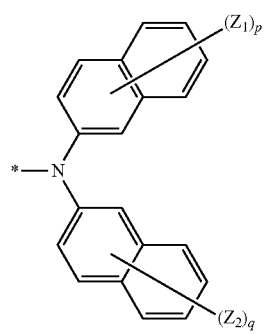
Formula 6D
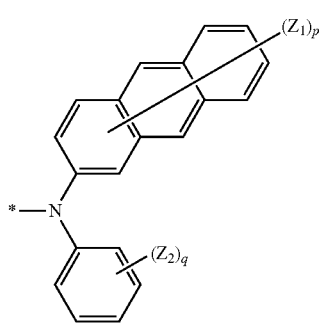
Formula 6E
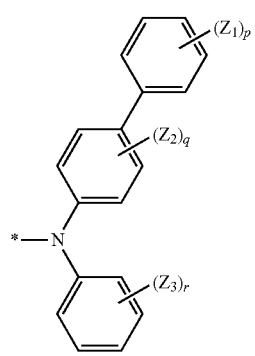
Formula 6F
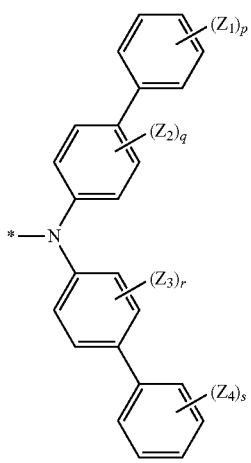
Formula 6G
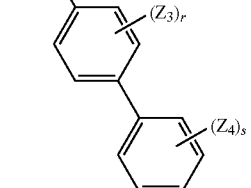
Formula 6H
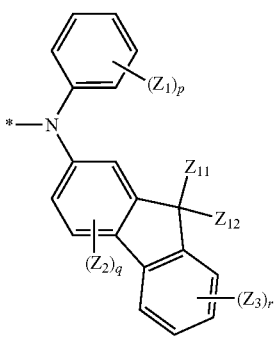
Formula 6I
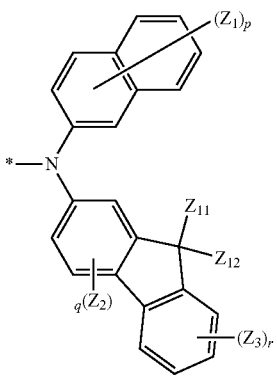
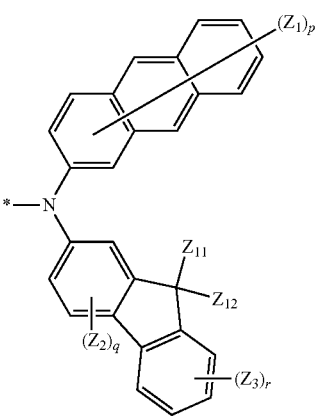

Formula 6J

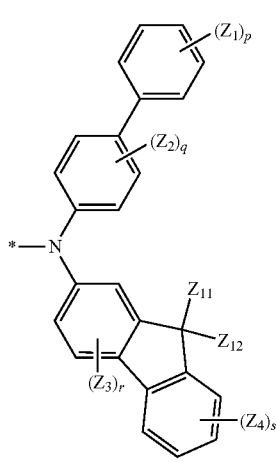

Formula 6K

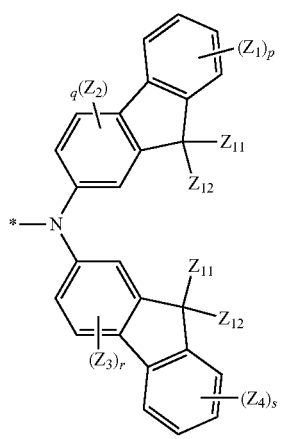

In Formulae 6A through 6K, $Z_1$ through $Z_4$ and $Z_{11}$ through $Z_{14}$ may each independently be, e.g., a hydrogen atom, a heavy hydrogen atom, a $C_1$-$C_{10}$ alkyl group (e.g., a methyl group, an ethyl group, a propyl group, a butyl group, and a pentyl group), a $C_1$-$C_{10}$ alkoxy group (e.g., a methoxy group, an ethoxy group, a propoxy group, a butoxy group, and a pentoxy group), and/or a $C_6$-$C_{14}$ aryl group (e.g., a phenyl group, a naphthyl group, and an anthryl group), p, q, r, and s may each independently be an integer of 1 to 8, and * is a binding site with $Ar_4$ or with ring atoms constituting a backbone of Formula 1. In an implementation, q may be an integer from 1 to 7, and r and s may be an integer from 1 to 4.

In Formula 1, "a" groups of $Ar_1$ in the group of —$(Ar_1)_a$—$Ar_{11}$ of the first substituent may be identical to or different from each other; "b" groups of $Ar_2$ in the group of —$(Ar_2)_b$—$Ar_{12}$ of the second substituent may be identical to or different from each other; "c" groups of $Ar_3$ in the group of —$(Ar_3)_c$—$Ar_{13}$ of the second substituent may be identical to or different from each other; "e" groups of $Ar_5$ in the group of —$(Ar_5)_e$—$Ar_{15}$ of the third substituent may be identical to or different from each other; and "f" groups of $Ar_6$ in the group of —$(Ar_6)_f$—$Ar_{16}$ of the third substituent may be identical to or different from each other.

Preferably, at least one of $R_1$ through $R_{12}$ in the condensed-cyclic compound represented by Formula 1 is —$(Ar_4)_d$—N[—$(Ar_5)_e$—$Ar_{15}$][—$(Ar_6)_f$—$Ar_{16}$] (the third substituent), wherein d is an integer of 1 through 10. Thus, preferably, $Ar_4$ is present in the condensed-cyclic compound of an embodiment. That is, a backbone including a combination of Formula 1 and Formula 2, or a backbone including a combination of Formula 1 and Formula 3 is preferably connected to a group represented by —N[—$(Ar_5)_e$—$Ar_{15}$][—$(Ar_6)_f$—$Ar_{16}$] via $Ar_4$. A lack or an insufficiency of electrons may be prevented at carbon sites constituting three benzene rings that are fused in the backbone of Formula 1 by $Ar_4$, which may prevent oxidation at the carbon sites. Thus, although the condensed-cyclic compound represented by Formula 1 may be attacked by nucleophilic particles, deterioration of the condensed-cyclic compound may be substantially prevented. Thus, an organic light-emitting device (OLED) including the condensed-cyclic compound represented by Formula 1 may have improved performance, e.g., a current density, efficiencies, brightness, and lifetime.

In Formula 1, $R_1$ through $R_{12}$ may each independently be, e.g., a hydrogen atom, a heavy hydrogen atom, a halogen atom, a hydroxyl group, a cyano group, the first substituent, the second substituent, and/or the third substituent; a in the first substituent may be 0 (that is, when any one of $R_1$ through $R_{12}$ may be the first substituent, $Ar_{11}$ may be connected directly to a ring atom constituting the backbone of Formula 1); b and c in the second substituent may each independently be 0 or 1; d in the third substituent may be 1 or 2, and e and f in the third substituent may each independently be 0 or 1; and $Ar_2$ through $Ar_6$ in the first substituent through the third substituent may each independently be, e.g., a substituted or unsubstituted $C_5$-$C_{14}$ arylene group and/or a substituted or unsubstituted $C_3$-$C_{14}$ heteroarylene group; and $Ar_{11}$, $Ar_{12}$, $Ar_{13}$, $Ar_{15}$, and $Ar_{16}$, among the first substituent through the third substituent, may each independently be, e.g., a hydrogen atom, a heavy hydrogen atom, a halogen atom, a hydroxyl group, a cyano group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_5$-$C_{14}$ aryl group, and/or a substituted or unsubstituted $C_3$-$C_{14}$ heteroaryl group. In an implementation, $Ar_2$ to $Ar_6$ may each independently be a substituted or unsubstituted $C_6$-$C_{14}$ arylene group.

For example, $R_1$ through $R_{12}$ may each independently be a hydrogen atom, a heavy hydrogen atom, a halogen atom, a hydroxyl group, a cyano group, the first substituent, the second substituent, and the third substituent; a in the first substituent may be 0; b and c in the second substituent may each independently be 0 or 1; d in the third substituent may be 1 or 2, e and f in the third substituent may each independently be 0 or 1; $Ar_2$ through $Ar_6$ in the first substituent through third substituent may each independently be a phenylene group, a $C_1$-$C_{10}$ alkyl phenylene group, a di($C_1$-$C_{10}$ alkyl)phenylene group, a ($C_6$-$C_{14}$aryl)phenylene group, a di($C_6$-$C_{14}$aryl)phenylene group, a carbazolylene group, a $C_1$-$C_{10}$ alkylcarbazolylene group, a di($C_1$-$C_{10}$alkyl)carbazolylene group, a $C_6$-$C_{14}$arylcarbazolylene group, a di($C_6$-$C_{14}$aryl)carbazolylene group, a fluorenylene group, a $C_1$-$C_{10}$ alkylfluorenylene group, a di($C_1$-$C_{10}$alkyl)fluorenylene group, a ($C_6$-$C_{14}$aryl)fluorenylene group, a di($C_6$-$C_{14}$ aryl)fluorenylene group, a naphthylene group, a $C_1$-$C_{10}$ alkyl naphthylene group, a di($C_1$-$C_{10}$alkyl)naphthylene group, a ($C_6$-$C_{14}$ aryl) naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$aryl)anthrylene group, a di($C_6$-$C_{14}$ aryl)anthrylene group, a pyridinylene group, a $C_1$-$C_{10}$alkylpyridinylene group, a di($C_1$-$C_{10}$ alkyl)pyridinylene group, a ($C_6$-$C_{14}$ aryl)pyridinylene group, a di($C_6$-$C_{14}$ aryl)pyridinylene group, a quinolinylene group, a $C_1$-$C_{10}$ alkylquinolinylene group, a di($C_1$-$C_{10}$ alkyl)quinolinylene group, a ($C_6$-$C_{14}$ aryl)quinolinylene group, a di($C_6$-$C_{14}$ aryl) quinolinylene group, a benzoimidazolylene group, a $C_1$-$C_{10}$alkylbenzoimidazolylene group, a di($C_1$-$C_{10}$ alkyl)benzoimidazolylene group, a ($C_6$-$C_{14}$aryl)benzoimidazolylene group, a di($C_6$-$C_{14}$aryl)benzoimidazolylene group, an imidazopyridinylene group, a $C_1$-$C_{10}$alkylimidazopyridinylene group, a di($C_1$-$C_{10}$alkyl) imidazopyridinylene group, a ($C_6$-$C_{14}$aryl)imidazopyridinylene group, a di($C_6$-$C_{14}$aryl)imidazopyridinylene group, an imidazopyrimidinylene group, a $C_1$-$C_{10}$alkylimidazopyrimidinylene group, a di($C_1$-$C_{10}$alkyl) imidazopyrimidinylene group, a ($C_6$-$C_{14}$aryl)imidazopyrimidinylene group, and/or a di($C_6$-$C_{14}$ aryl)imidazopyrimidinylene group; $Ar_{11}$, $Ar_{12}$, $Ar_{13}$, $Ar_{15}$, and $Ar_{16}$, among the first substituent through third, substituent may each independently be a hydrogen atom, a heavy hydrogen atom, a halogen atom, a hydroxyl group, a cyano group, a methyl group, an ethyl group, a propyl group, a buthyl group, penthyl group, an ethenyl group, a prophenyl group, a butenyl group, a pentenyl group, an acethyl group, a methoxy group, an ethoxy group, a propoxy group, a butoxy group, a pentoxy group, a phenyl group, a $C_1$-$C_{10}$ alkylphenyl group, a di($C_1$-$C_{10}$ alkyl)phenyl group, a ($C_6$-$C_{14}$ aryl)phenyl group, a di($C_6$-$C_{14}$aryl)phenyl group, a carbazolyl group, a $C_1$-$C_{10}$alkyl carbazolyl group, a di($C_1$-$C_{10}$alkyl)carbazolyl group, a $C_6$-$C_{14}$aryl carbazolyl group, a di($C_6$-$C_{14}$aryl)carbazolyl group, a fluorenyl group, a $C_1$-$C_{10}$alkylfluorenyl group, a di($C_1$-$C_{10}$alkyl)fluorenyl group, a ($C_6$-$C_{14}$aryl)fluorenyl group, a di($C_6$-$C_{14}$aryl)fluorenyl group, a naphthyl group, a $C_1$-$C_{10}$alkylnaphthyl group, a di($C_1$-$C_{10}$alkyl)naphthyl group, a ($C_6$-$C_{14}$aryl)naphthyl group, a di($C_6$-$C_{14}$ aryl)naphthyl group, an anthryl group, a $C_1$-$C_{10}$alkylanthryl group, a di($C_1$-$C_{10}$alkyl)anthryl group, a ($C_6$-$C_{14}$aryl)anthryl group, a di($C_6$-$C_{14}$aryl)anthryl group, a pyridinyl group, a $C_1$-$C_{10}$alkylpyridinyl group, a di($C_1$-$C_{10}$alkyl)pyridinyl group, a ($C_6$-$C_{14}$aryl)pyridinyl group, a di($C_6$-$C_{14}$aryl)pyridinyl group, a quinolinyl group, a $C_1$-$C_{10}$alkylquinolinyl group, a di($C_1$-$C_{10}$alkyl)quinolinyl group, a ($C_6$-$C_{14}$aryl)quinolinyl group, a di($C_6$-$C_{14}$aryl) quinolinyl group, a benzoimidazolyl group, a $C_1$-$C_{10}$alkylbenzoimidazolyl group, a di($C_1$-$C_{10}$alkyl)benzoimidazolyl group, a ($C_6$-$C_{14}$aryl)benzoimidazolyl group, a di($C_6$-$C_{14}$aryl)benzoimidazolyl group, an imidazopyridinyl group, a $C_1$-$C_{10}$alkylimidazopyridinyl group, a di($C_1$-$C_{10}$alkyl)imidazopyridinyl group, a ($C_6$-$C_{14}$aryl) imidazopyridinyl group, a di($C_6$-$C_{14}$aryl)imidazopyridinyl group, an imidazopyrimidinyl group, a $C_1$-$C_{10}$alkylimidazopyrimidinyl group, a di($C_1$-$C_{10}$alkyl) imidazopyrimidinyl group, a ($C_6$-$C_{14}$aryl)imidazopyrimidinyl group, and/or a di($C_6$-$C_{14}$ aryl) imidazopyrimidinyl group, but are not limited thereto.

In an implementation, the condensed-cyclic compound represented by Formula 1 may be represented by any one of Formulae 2a through 2d below (a ring 'A' in Formula 1 is represented by Formula 2):

Formula 2a

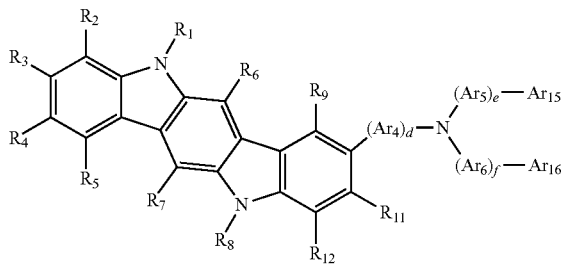

Formula 2b

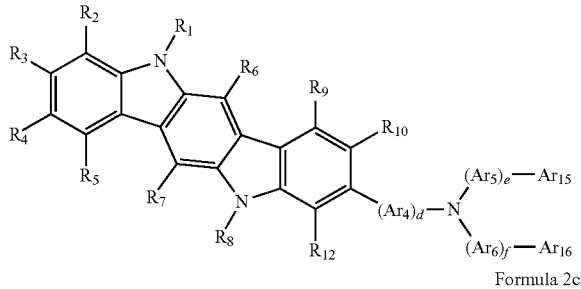

Formula 2c

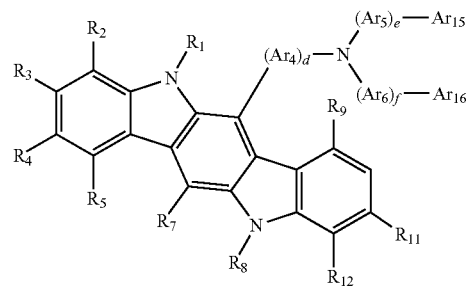

Formula 2d

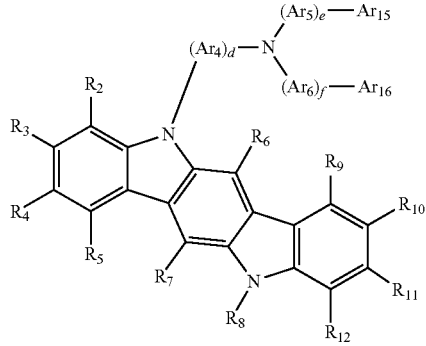

In Formulae 2a through 2d, $R_1$ through $R_{12}$, $Ar_1$ through $Ar_6$, $Ar_{11}$, $Ar_{12}$, $Ar_{13}$, $Ar_{15}$, $Ar_{16}$, a, b, c, d, and f may be defined as described above.

In Formulae 2a through 2d, $Ar_4$ may be, e.g., a phenylene group, a $C_1$-$C_{10}$ phenylene group, a di($C_1$-$C_{10}$alkyl)phenylene group, a ($C_6$-$C_{14}$ aryl)phenylene group, a di($C_6$-$C_{14}$ aryl)phenylene group, a carbazolylene group, a $C_1$-$C_{10}$alkylcarbazolylene group, a di($C_1$-$C_{10}$alkyl)carbazolylene group, a $C_6$-$C_{14}$arylcarbazolylene group, a di($C_6$-$C_{14}$aryl)carbazolylene group, a fluorenylene group, a $C_1$-$C_{10}$alkylfluorenylene group, a di($C_1$-$C_{10}$alkyl)fluorenylene group, a ($C_6$-$C_{14}$aryl)fluorenylene group, a di($C_6$-$C_{14}$aryl)fluorenylene group, a naphthylene group, a $C_1$-$C_{10}$alkylnaphthylene group, a di($C_1$-$C_{10}$alkyl)naphthylene group, a ($C_6$-$C_{14}$aryl)naphthylene group, a di($C_6$-$C_{14}$aryl)naphthylene group, an anthrylene group, a $C_1$-$C_{10}$alkylanthrylene group, a di($C_1$-$C_{10}$alkyl)anthrylene group, a ($C_6$-$C_{14}$aryl)anthrylene group, a di($C_6$-$C_{14}$aryl)anthrylene group, a pyridinylene group, a $C_1$-$C_{10}$alkylpyridinylene group, a di($C_1$-$C_{10}$alkyl)pyridinylene group, a ($C_6$-$C_{14}$aryl)pyridinylene group, a di($C_6$-$C_{14}$aryl)pyridinylene group, a quinolinylene group, a $C_1$-$C_{10}$alkylquinolinylene group, a di($C_1$-$C_{10}$alkyl)quinolinylene group, a di($C_6$-$C_{14}$aryl)quinolinylene group, a benzoimidazolylene group, a $C_1$-$C_{10}$alkylbenzoimidazolylene group, a di($C_1$-$C_{10}$alkyl) benzoimidazolylene group, a ($C_6$-$C_{14}$aryl)benzoimidazolylene group, a di($C_6$-$C_{14}$aryl)benzoimidazolylene group, an imidazopyridinylene group, a $C_1$-$C_{10}$alkylimidazopyridinylene group, a di($C_1$-$C_{10}$alkyl)imidazopyridinylene group, a ($C_6$-$C_{14}$aryl)imidazopyridinylene group, a di($C_6$-$C_{14}$aryl)imidazopyridinylene group, an limidazopyrimidinylene group, a $C_1$-$C_{10}$alkylimidazopyrimidinylene group, a di($C_1$-$C_{10}$alkyl)imidazopyrimidinylene group, a ($C_6$-$C_{14}$aryl) imidazopyrimidinylene group, or a di($C_6$-$C_{14}$aryl)imidazopyrimidinylene group. In Formulae 2a through 2d, d may be 1, 2, or 3. For example, in Formulae 2a through 2d, $Ar_4$ may be a phenylene group and d may be 1 or 2, but the present embodiment is not limited thereto.

—N[—$(Ar_5)_e$—$Ar_{15}$][—$(Ar_6)_f$—$Ar_{16}$] of the third substituent represented by —$(Ar_4)_d$—N[—$(Ar_5)_e$—$Ar_{15}$][—$(Ar_6)_f$—$Ar_{16}$] in Formulae 2a through 2d may be represented by any one of Formulae 6A through 6K.

In Formulae 2a through 2c, $R_1$ and $R_8$ may each be, e.g., the first substituent, and "a" in the first substituent may be 0. For example, in Formulae 2a through 2c, $R_1$ and $R_8$ may be the first substituent, "a" in the first substituent may be 0, and $Ar_{11}$ may be a substituted or unsubstituted $C_5$-$C_{14}$ aryl group or a substituted or unsubstituted $C_3$-$C_{14}$ heteroaryl group. In detail, in Formulae 2a through 2c, $R_1$ and $R_8$ may each independently be, e.g., a phenyl group.

In Formula 2d, $R_8$ may be the first substituent and "a" in the first substituent may be 0. For example, in Formula 2d, $R_8$ may be the first substituent, "a" in the first substituent may be 0, and $Ar_{11}$ may be a substituted or unsubstituted $C_5$-$C_{14}$ aryl group and/or a substituted or unsubstituted $C_3$-$C_{14}$ heteroaryl group. In detail, in Formula 2d, $R_1$ and $R_8$ may each be a phenyl group.

In an implementation, the condensed-cyclic compound represented by Formula 1 may be represented by any one of Formulae 3a through 3e below (a ring 'A' in Formula 1 is represented by Formula 3):

Formula 3a

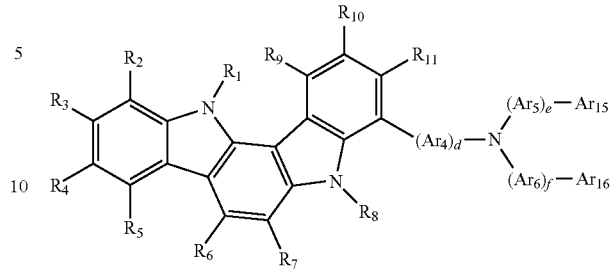

Formula 3b

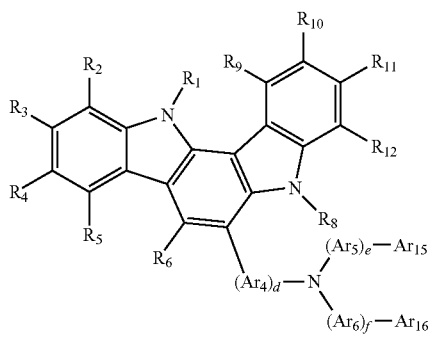

Formula 3c

Formula 3d

Formula 3e

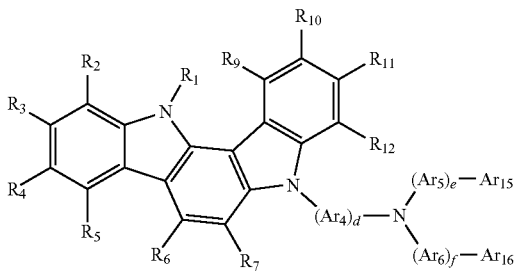

In Formulae 3a through 3e, $R_1$ through $R_{12}$, $Ar_1$ through $Ar_6$, $Ar_{11}$, $Ar_{12}$, $Ar_{13}$, $Ar_{15}$, $Ar_{16}$, a, b, c, d, and f may be defined as described above.

In Formulae 3a through 3e, $Ar_4$ may be, e.g., a phenylene group, a $C_1$-$C_{10}$ phenylene group, a di($C_1$-$C_{10}$alkyl)phenylene group, a ($C_6$-$C_{14}$aryl)phenylene group, a di($C_6$-$C_{14}$aryl)phenylene group, a carbazolylene group, a $C_1$-$C_{10}$alkylcarbazolylene group, a di($C_1$-$C_{10}$alkyl)carbazolylene group, a $C_6$-$C_{14}$arylcarbazolylene group, a di($C_6$-$C_{14}$aryl)carbazolylene group, a fluorenylene group, a $C_1$-$C_{10}$alkylfluorenylene group, a di($C_1$-$C_{10}$alkyl)fluorenylene group, a ($C_6$-$C_{14}$aryl)fluorenylene group, a di($C_6$-$C_{14}$aryl)fluorenylene group, a naphthylene group, a $C_1$-$C_{10}$alkylnaphthylene group, a di($C_1$-$C_{10}$alkyl)naphthylene group, a ($C_6$-$C_{14}$aryl)naphthylene group, a di($C_6$-$C_{14}$aryl)naphthylene group, an anthrylene group, a $C_1$-$C_{10}$alkylanthrylene group, a di($C_1$-$C_{10}$alkyl)anthrylene group, a ($C_6$-$C_{14}$aryl)anthrylene group, a di($C_6$-$C_{14}$aryl)anthrylene group, a pyridinylene group, a $C_1$-$C_{10}$alkylpyridinylene group, a di($C_1$-$C_{10}$alkyl)pyridinylene group, a ($C_6$-$C_{14}$aryl)pyridinylene group, a di($C_6$-

$C_{14}$aryl)pyridinylene group, a quinolinylene group, a $C_1$-$C_{10}$alkylquinolinylene group, a di($C_1$-$C_{10}$alkyl)quinolinylene group, a ($C_6$-$C_{14}$aryl)quinolinylene group, a di($C_6$-$C_{14}$aryl)quinolinylene group, a benzoimidazolylene group, a $C_1$-$C_{10}$alkylbenzoimidazolylene group, a di($C_1$-$C_{10}$alkyl)benzoimidazolylene group, a ($C_6$-$C_{14}$aryl)benzoimidazolylene group, a di($C_6$-$C_{14}$aryl)benzoimidazolylene group, an imidazopyridinylene group, a $C_1$-$C_{10}$alkylimidazopyridinylene group, a di($C_1$-$C_{10}$alkyl)imidazopyridinylene group, a ($C_6$-$C_{14}$aryl)imidazopyridinylene group, a di($C_6$-$C_{14}$aryl)imidazopyridinylene group, an imidazopyrimidinylene group, a $C_1$-$C_{10}$alkylimidazopyrimidinylene group, a di($C_1$-$C_{10}$alkyl)imidazopyrimidinylene group, a ($C_6$-$C_{14}$aryl) imidazopyrimidinylene group, and/or a di($C_6$-$C_{14}$ aryl)imidazopyrimidinylene group. In Formulae 3a through 3e, d may be 1, 2, or 3. For example, in Formulae 3a through 3e, $Ar_4$ may be a phenylene group and d may be 1 or 2, but the present embodiment is not limited thereto.

In Formulae 3a through 3e, —N[—($Ar_5$)$_e$—$Ar_{15}$][—($Ar_6$)$_f$—$Ar_{16}$] of the third substituent represented by —($Ar_4$)$_d$—N[—($Ar_5$)$_e$—$Ar_{15}$][—($Ar_6$)$_f$—$Ar_{16}$] may be represented by any one of Formulae 6A through 6K.

In Formulae 3a through 3d, $R_1$ and $R_8$ may each be, e.g., a first substituent and "a" in the first substituent may be 0. For example, in Formulae 3a through 3d, $R_1$ and $R_8$ may each be the first substituent, "a" in the first substituent may be 0, and $Ar_{11}$ may be a substituted or unsubstituted $C_5$-$C_{14}$ aryl group and/or a substituted or unsubstituted $C_3$-$C_{14}$ heteroaryl group. In detail, in Formulae 3a through 3d, $R_1$ and $R_8$ may each be a phenyl group.

In Formula 3e, $R_8$ may be, e.g., the first substituent and "a" in the first substituent may be 0. For example, in Formula 3e, $R_8$ may be the first substituent, "a" in the first substituent may be 0, and $Ar_{11}$ may be a substituted or unsubstituted $C_5$-$C_{14}$ aryl group and/or a substituted or unsubstituted $C_3$-$C_{14}$ heteroaryl group. In detail, in Formula 3e, $R_1$ and $R_8$ may each be a phenyl group.

In an implementation, the condensed-cyclic compound represented by Formula 1 may be Compounds 1 through 27 below, but is not limited thereto:

Compound 1

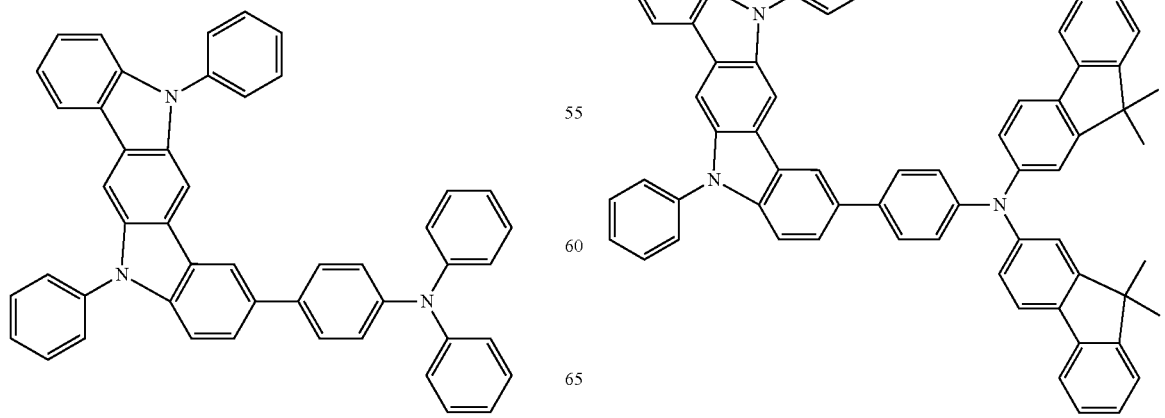

Compound 2

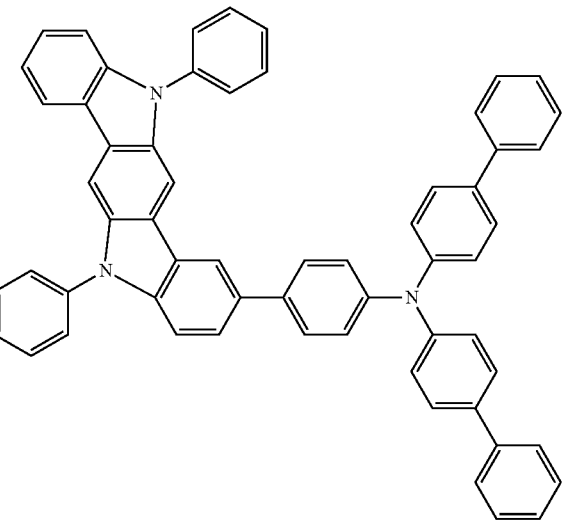

Compound 3

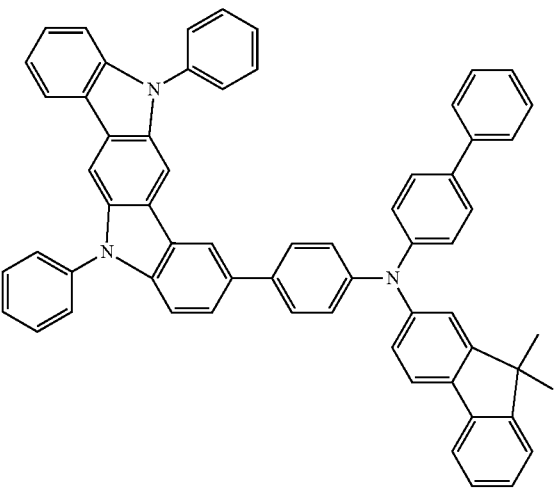

Compound 4

Compound 5
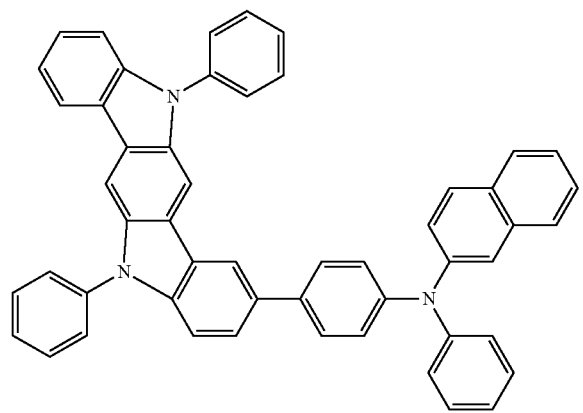
Compound 6
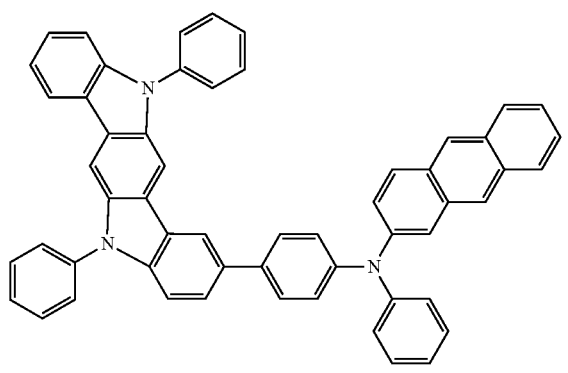
Compound 7
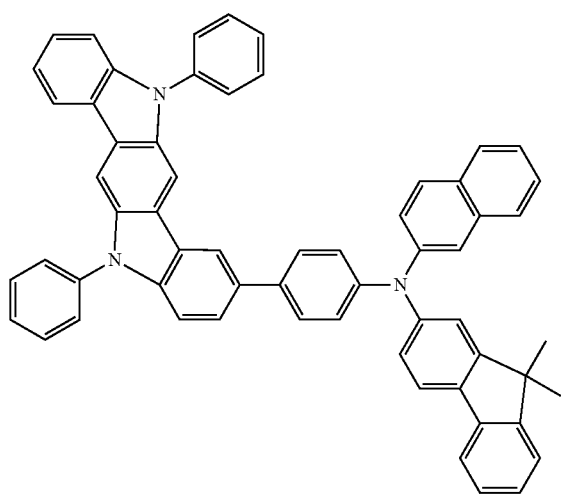
Compound 8
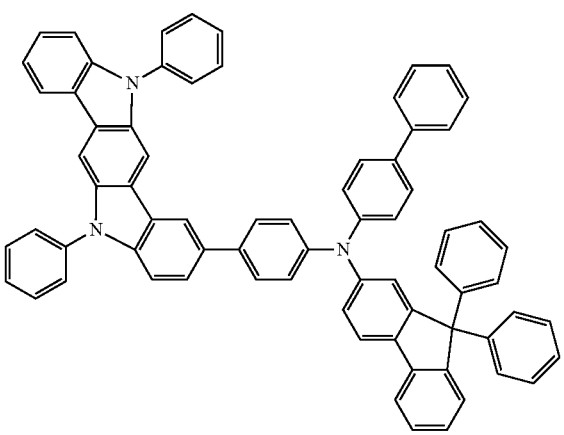
Compound 9
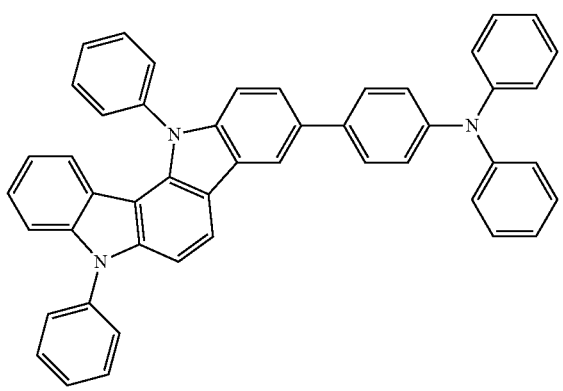
Compound 10
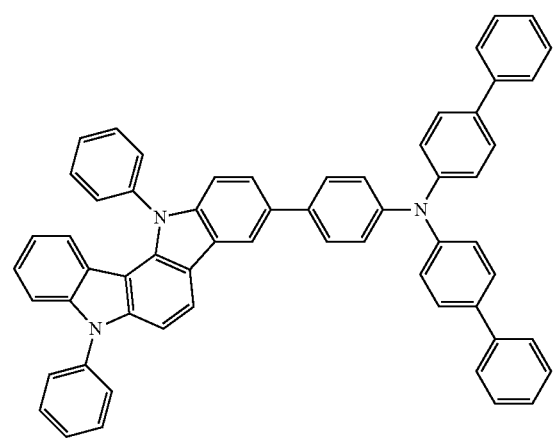

-continued
Compound 11
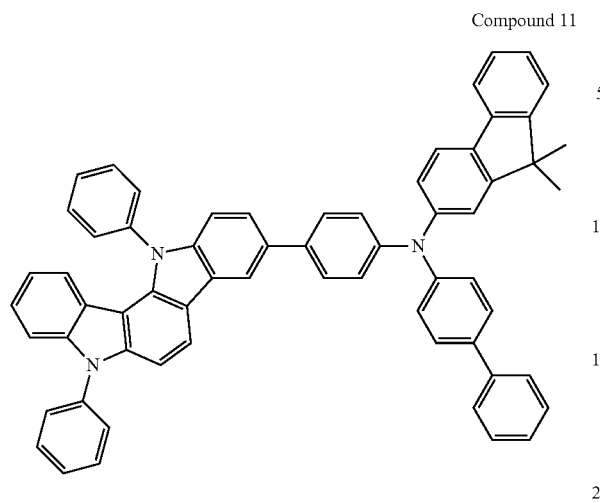
Compound 12
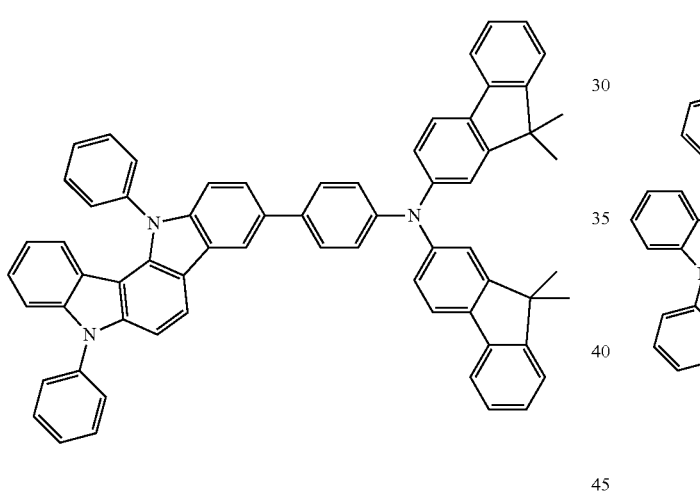
Compound 13
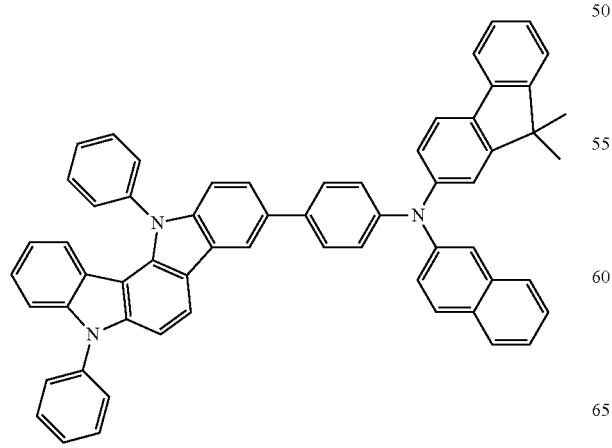
-continued
Compound 14
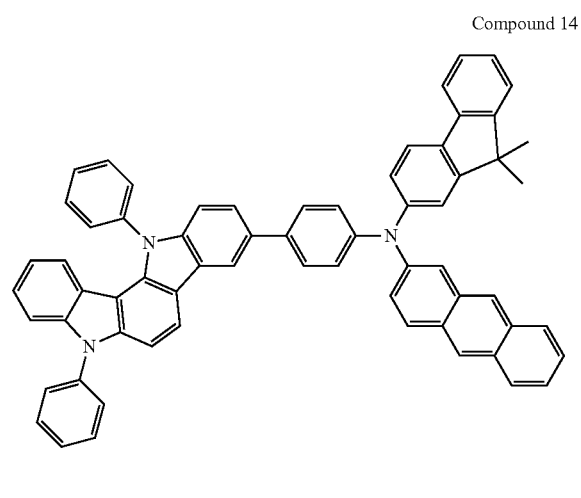
Compound 15
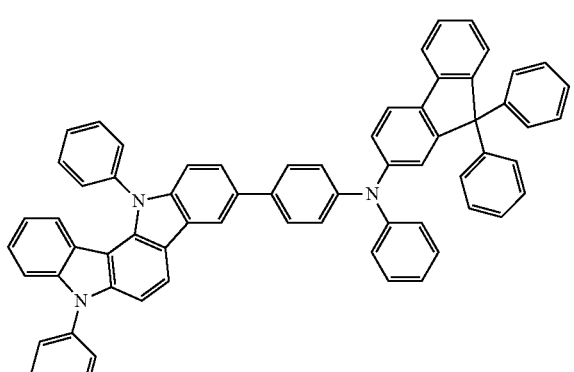
Compound 16
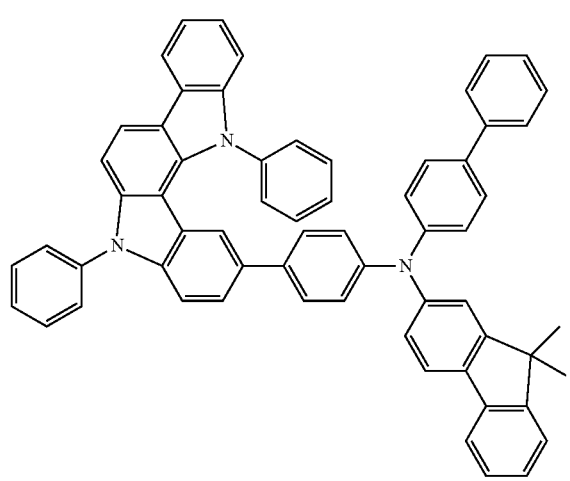

Compound 17
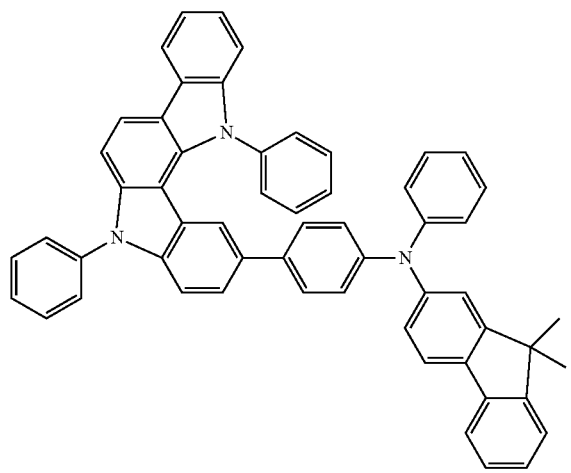
Compound 18
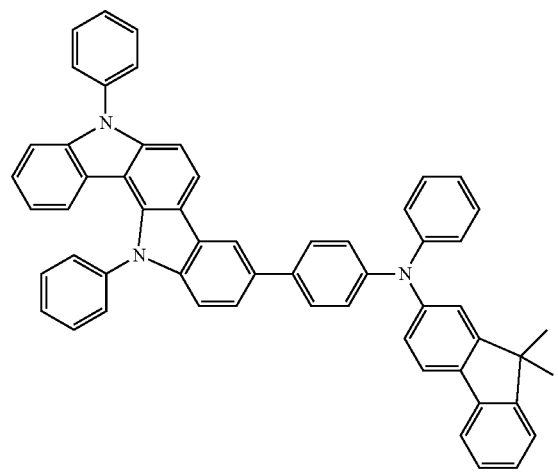
Compound 19
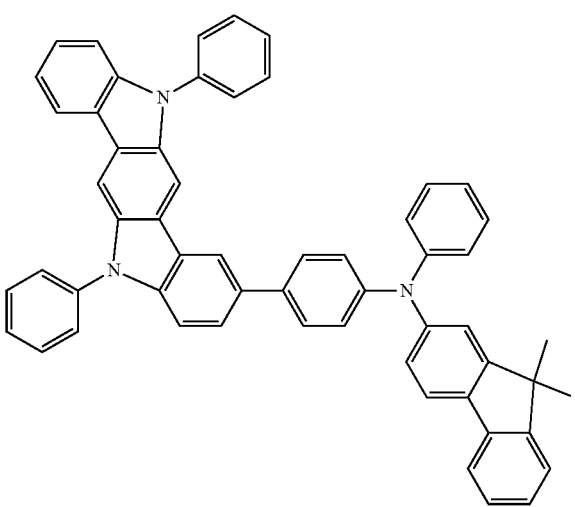
Compound 20
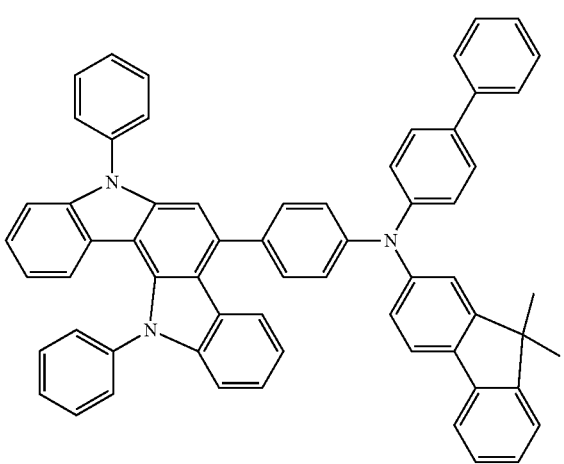
Compound 21
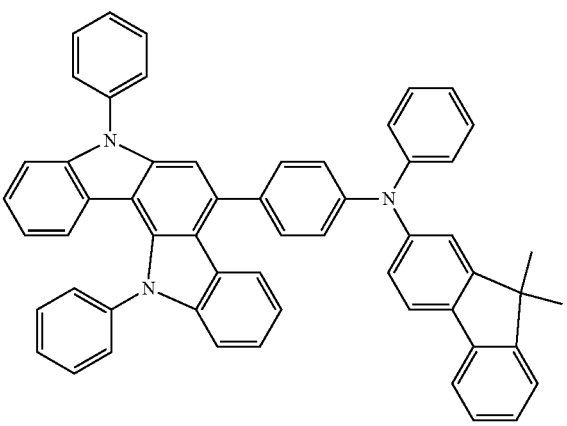
Compound 22
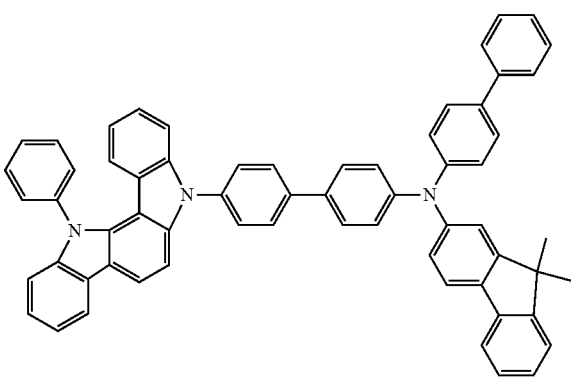

Compound 23
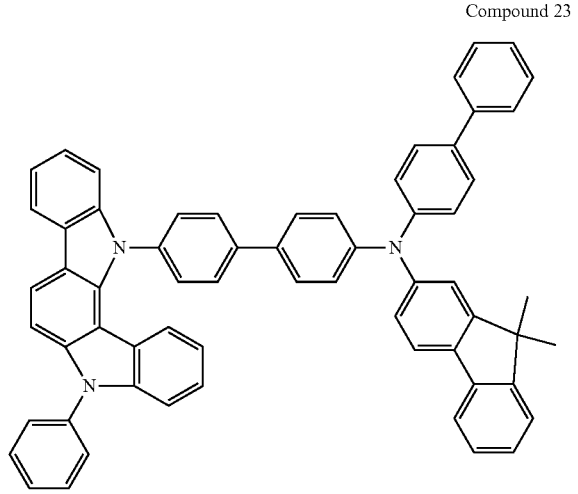

Compound 27
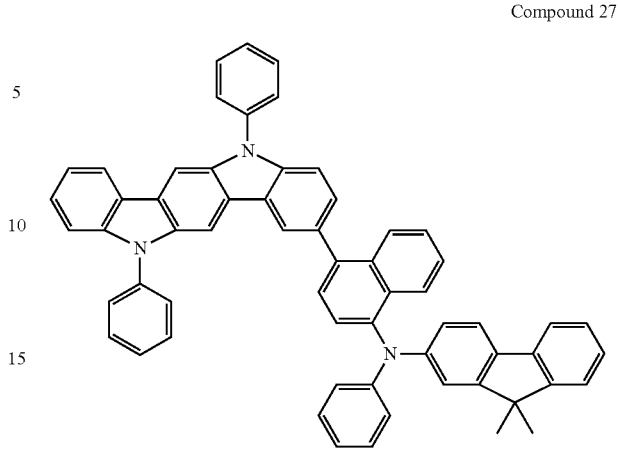

Compound 24
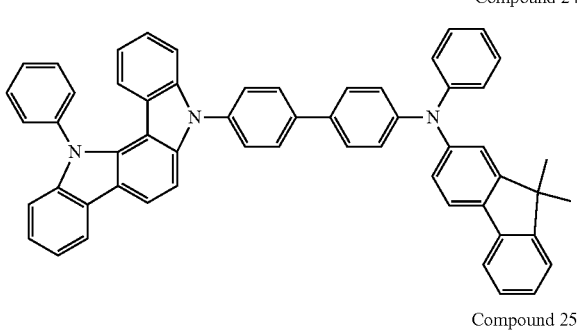

Compound 25
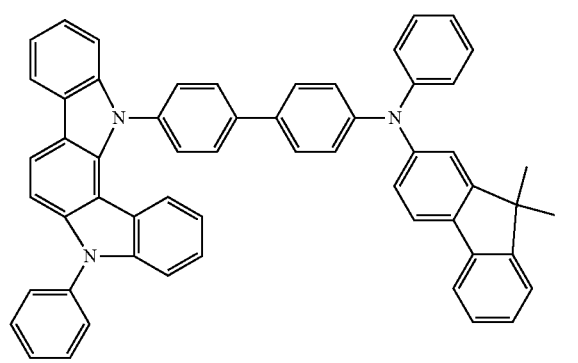

Compound 26
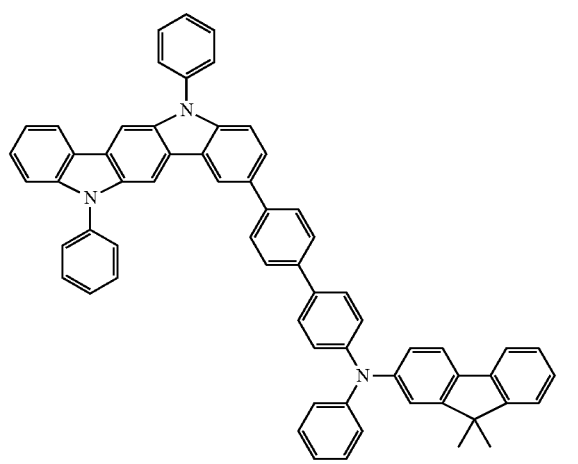

Examples of the unsubstituted $C_1$-$C_{30}$ alkyl group used herein may include methyl, ethyl, propyl, isobutyl, sec-butyl, pentyl, iso-amyl, hexyl, and the like. In the substituted $C_1$-$C_{30}$ alkyl group, at least one hydrogen atom of the unsubstituted $C_1$-$C_{30}$ alkyl group described above may be substituted with, e.g., a heavy hydrogen atom, a halogen atom, a hydroxyl group, a nitro group, a cyano group, an amino group, an amidino group, hydrazine, hydrazone, a carboxyl group or salts thereof, a sulfonic acid group or salts thereof, a phosphoric acid or salts thereof, a $C_1$-$C_{30}$ alkyl group, a $C_2$-$C_{30}$ alkenyl group, a $C_2$-$C_{30}$ alkynyl group, a $C_6$-$C_{30}$ aryl group, a $C_2$-$C_{20}$ heteroaryl group, —N($Q_1$)($Q_2$), or —Si($Q_3$)($Q_4$)($Q_5$), wherein $Q_1$ through $Q_5$ may each independently be a hydrogen atom, a heavy hydrogen atom, a $C_1$-$C_{30}$ alkyl group, a $C_2$-$C_{30}$ alkenyl group, a $C_2$-$C_{30}$ alkynyl group, a $C_6$-$C_{30}$ aryl group, and a $C_2$-$C_{20}$ heteroaryl group. The substituted or unsubstituted $C_1$-$C_{30}$ alkylene group may be, e.g., a divalent linking group having the same structure as the substituted or unsubstituted $C_1$-$C_{30}$ alkyl group described above.

The unsubstituted $C_1$-$C_{30}$ alkoxy group may be a group represented by —OA, wherein A is an unsubstituted $C_1$-$C_{30}$ alkyl group described above. Examples of the unsubstituted $C_1$-$C_{30}$ alkoxy group may include a methoxy group, an ethoxy group, and an isopropyloxy group. At least one of the hydrogen atoms in the alkoxy group may be substituted with the substituents described above in conjunction with the substituted $C_1$-$C_{30}$ alkyl group.

The unsubstituted $C_2$-$C_{30}$ alkenyl group may be a hydrocarbon chain having a carbon-carbon double bond in a center or at a terminus of the unsubstituted $C_2$-$C_{30}$ alkyl group. Examples of the alkenyl group may include an ethenyl group, a propenyl group, a butenyl group, and the like. At least one hydrogen atom in the unsubstituted $C_2$-$C_{30}$ alkenyl group may be substituted with the substituents described in conjunction with the substituted $C_1$-$C_{30}$ alkyl group. The substituted or unsubstituted $C_2$-$C_{30}$ alkenylene group may be a divalent linking group having the same structure as the substituted or unsubstituted $C_2$-$C_{30}$ alkenyl group described above.

The unsubstituted $C_2$-$C_{30}$ alkynyl group may be a hydrocarbon chain having at least one carbon-carbon triple bond in a center or at a terminus of the $C_2$-$C_{30}$ alkyl group. Examples of the unsubstituted $C_2$-$C_{20}$ alkynyl group may include ethynyl, propynyl, and the like. At least one hydrogen atom in the alkynyl group may be substituted with the substituents described above in conjunction with the $C_1$-$C_{30}$ alkyl group.

The unsubstituted $C_5$-$C_{30}$ aryl group may be a monovalent group having a carbocyclic aromatic system having 5 to 30 carbon atoms including at least one aromatic ring. The unsubstituted $C_5$-$C_{30}$ arylene group may be a divalent group having a carbocyclic aromatic system having 5 to 30 carbon atoms including at least one aromatic ring. When the aryl group and the arylene group have at least two rings, they may be fused to each other. At least one hydrogen atom in the aryl group and the arylene group may be substituted with the substituents described above in conjunction with the $C_1$-$C_{30}$ alkyl group.

Examples of the substituted or unsubstituted $C_5$-$C_{30}$ aryl group may include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and/or an ovalenyl group. Examples of the substituted $C_5$-$C_{30}$ aryl group may be inferred based on those of the unsubstituted $C_5$-$C_{30}$ aryl group and the substituted $C_1$-$C_{30}$ alkyl group described above. Examples of the substituted or unsubstituted $C_5$-$C_{30}$ arylene group may be inferred based on examples of the substituted or unsubstituted $C_5$-$C_{30}$ aryl group.

The unsubstituted $C_3$-$C_{30}$ heteroaryl group may be a monovalent group having at least one aromatic ring having at least one heteroatom including at least one of N, O, P, and S. The unsubstituted $C_3$-$C_{30}$ heteroarylene group may be a divalent group having at least one aromatic ring having at least one of the heteroatoms including, e.g., N, O, P, and S. In this regard, when the heteroaryl group and the heteroarylene group have at least two rings, they may be fused to each other. At least one hydrogen atom in the heteroaryl group and the heteroarylene group may be substituted with the substituents described above in conjunction with the $C_1$-$C_{30}$ alkyl group.

Examples of the unsubstituted $C_3$-$C_{30}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyll group, an imidazopyridinyl group, and/or an imidazopyrimidinyl group. Examples of the unsubstituted $C_3$-$C_{30}$ heteroarylene group may be inferred based on examples of the substituted or unsubstituted $C_6$-$C_{30}$ arylene group.

The condensed-cyclic compound of Formula 1 may be synthesized by using organic synthesis. A method of synthesizing the condensed-cyclic compound may be inferred based on Examples that will be described later.

The condensed-cyclic compound of Formula 1 may be used in an organic light-emitting device. According to another embodiment, an organic light-emitting device may include a first electrode, a second electrode disposed opposite to the first electrode, and a first layer disposed between the first electrode and the second electrode, wherein the first layer include the condensed-cyclic compound of Formula 1 described above.

The first layer may be at least one of a HTL, a HIL, a functional layer having both a hole injection function and a hole transport function, an EML, an ETL and an EIL, but is not limited thereto. For example, the first layer may be at least one of a HTL, a HIL, a functional layer having both a hole injection function and a hole transport function, and an EML, but is not limited thereto. In addition, various known layers may be used as the first layer, according to a structure of an OLED to be embodied.

FIG. 1 illustrates a schematic sectional view of an organic light-emitting device (OLED) 10 according to an embodiment. Hereinafter, a method of manufacturing an organic light-emitting device according to an embodiment and an organic light-emitting device according to an embodiment will now be described with reference to FIG. 1.

Referring to FIG. 1, the OLED 10 according to the present embodiment may include a substrate 11, a first electrode 13, an organic layer 15, and a second electrode 17, which are sequentially stacked in this order.

The substrate 11, which may be any suitable substrate that is used in conventional organic light-emitting devices, may be, e.g., a glass substrate or a transparent plastic substrate with excellent mechanical strength, thermal stability, transparency, surface smoothness, ease of handling, and water resistance.

The first electrode 13 may be formed by, e.g., depositing or sputtering a material that is used to form the first electrode 13 on the substrate. When the first electrode 13 constitutes an anode, the material used to form the first electrode 13 may be a high work-function material so as to facilitate hole injection. The first electrode 13 may be a reflective electrode or a transmission electrode. Transparent and conductive materials, e.g., ITO, IZO, $SnO_2$, and ZnO, may be used to form the first electrode 13. The first electrode 13 may be formed as a reflective electrode using, e.g., magnesium (Mg), aluminum (Al), aluminum-lithium (Al—Li), calcium (Ca), magnesium-indium (Mg—In), magnesium-silver (Mg—Ag), or the like.

The organic layer 15 may be disposed on the first electrode 13. The term "organic layer" used herein indicates any layer interposed between the first electrode 13 and the second electrode 17. The organic layer 15 may not be formed of pure organic materials, and may also include, e.g., a metal complex.

The organic layer 15 may include the first layer including the condensed-cyclic compound of Formula 1. The organic layer may further include at least one of a hole injection layer (HIL), a hole transport layer (HTL), a functional layer having both a hole injection function and a hole transport function, an emissive layer (EML), a hole blocking layer (HBL), an electron transport layer (ETL), and an electron injection layer (EIL). For example, the first layer is a HTL, the organic layer 15 may further include a HIL, an EML, an ETL, and an EIL, in addition to the first layer, but is not limited thereto.

The HIL may be formed on the first electrode 13 by, e.g., vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the structure and thermal properties of the HIL to be formed. For example, the coating rate may be in the range of about 2000 to about 5000 rpm, and a temperature at which heat treatment is performed to remove a solvent after coating may be in the range of about 80° C. to about 200° C. However, the coating conditions are not limited thereto.

The HIL may be formed of at least one of the condensed-cyclic compound represented by Formula 1 and any suitable material that is commonly used to form a HIL. Examples of the known material that can be used to form the HIL may include, but are not limited to, N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4''-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/P SS), polyaniline/camphor sulfonicacid (Pani/CSA), and polyaniline/poly(4-styrenesulfonate) (PANI/PSS).

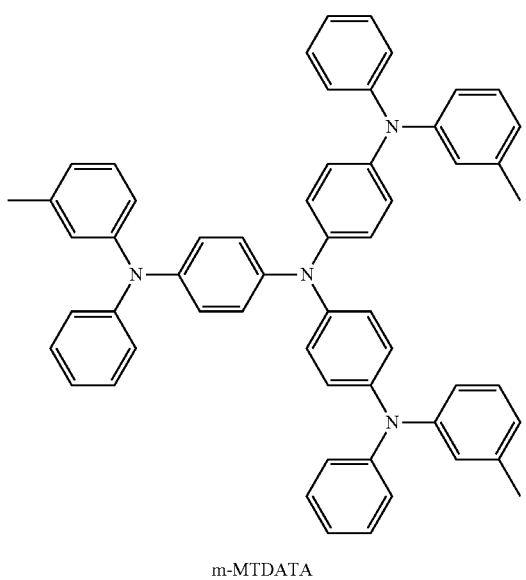

m-MTDATA

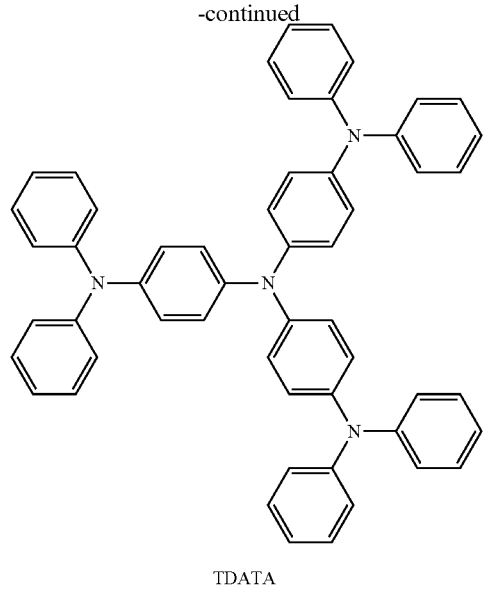

TDATA

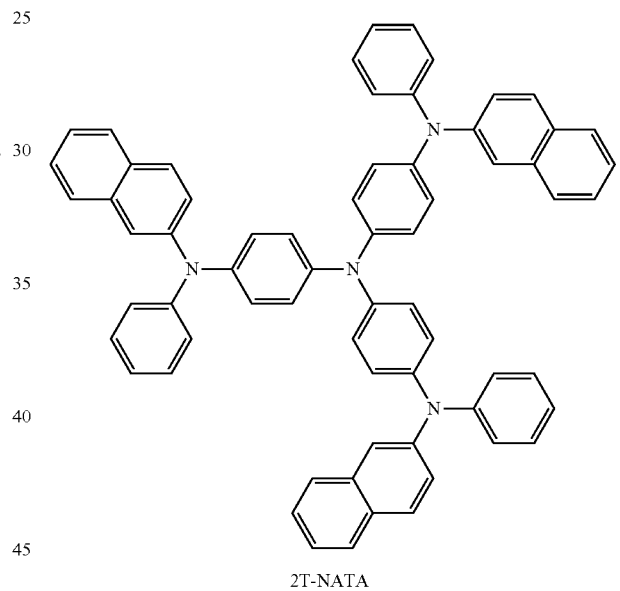

2T-NATA

The thickness of the HIL may be, e.g., about 100 Å to about 10,000 Å. Maintaining the thickness of the HIL at about 100 Å to about 10,000 Å may help ensure that the HIL has excellent hole injecting ability without a substantial increase in driving voltage. In an implementation, the thickness of the HIL may be, e.g., about 100 Å to about 1,000 Å.

Then, the HTL may be formed on the HIL by using, e.g., vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may include, or may be formed of the condensed-cyclic compound represented by Formula 1 as described above. The first layer including the condensed-cyclic compound represented by Formula 1 may be the HTL. If the first layer is not a HTL, the HTL may be formed using any suitable hole transporting material. Examples of the known hole transporting material may include: a carbazole derivative such as N-phenylcarbazole or polyvinylcarbazole; an amine derivative having an aromatic condensation ring, such as N,N'-bis(3-methylphenyl)-N,N'-diphenyl-[1,1-biphenyl]-4,4'-diamine (TPD) illustrated below; and a triphenylamine-based material, such as 4,4',4"-tris(N-carbazolyl)triphenylamine (TCTA). Among these materials, TCTA may not only transport holes but may also inhibit excitons from being diffused into the EML.

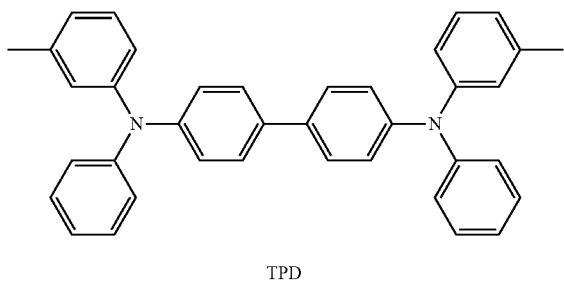

TPD

The thickness of the HTL may be about 50 Å to about 1,000 Å. Maintaining the thickness of the HTL at about 50 Å to about 1,000 Å may help ensure that the HTL has excellent hole transporting ability without a substantial increase in driving voltage. In an implementation, the thickness of the HTL may be, e.g., about 100 Å to about 800 Å.

Alternatively, the functional layer having both a hole injection function and a hole transport function may be formed instead of the HIL and the HTL. The functional layer may be formed of a known material for forming the functional layer.

At least one of the HIL, the HTL, and the functional layer may further include a charge-generating material so as to improve conductivity of a layer, in addition to the condensed-cyclic compound of Formula 1, the known material for the HIL, and the known material for the HTL.

The charge-generating material may be a p-dopant. Examples of the p-dopant unlimitedly include quinone derivatives, such as tetracyanoquinodimethane (TCNQ) and 2,3,5,6-tetrafluoro-tetracyano-1,4-benzoquinondimethane (F4TCNQ); metal oxides, such as a tungsten oxide and a molybdenum oxide; and a cyano group-containing compound represented by Compound 100 below, but are not limited thereto.

Compound 100

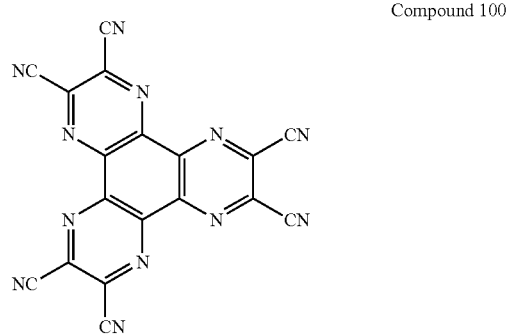 [SMILES: N#Cc1nc2c3nc(C#N)c(C#N)nc3c3nc(C#N)c(C#N)nc3c2nc1C#N]

When the HIL, the HTL, or the functional layer further includes the charge-generating material, the charge-generating material may be homogeneously or ununiformly dispersed in the HIL, the HTL, or the functional layer.

Then, the EML may be formed on the HTL or the functional layer by using, e.g., vacuum deposition, spin coating, casting, LB deposition, or the like. When the EML is formed using vacuum deposition or spin coating, the deposition and coating conditions may be similar to whose for the formation of the HIL, though the conditions for deposition and coating may vary according to the material that is used to form the EML.

The EML may be formed of at least one of the condensed-cyclic compound of Formula 1 and any suitable light-emitting material (including both a host and a dopant). Example of the host may include $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), bur are not limited thereto.

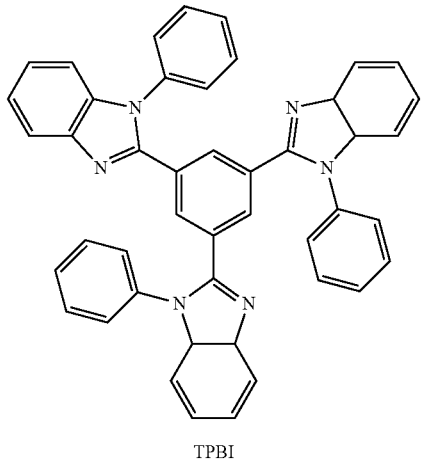

TPBI

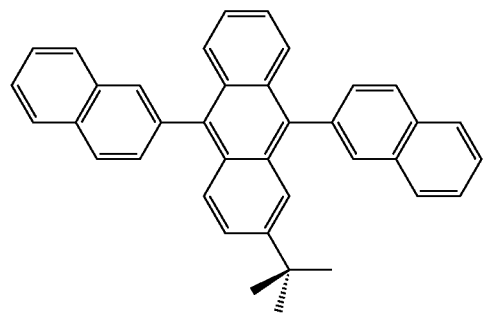

TBADN

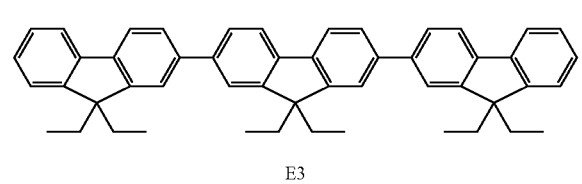

E3

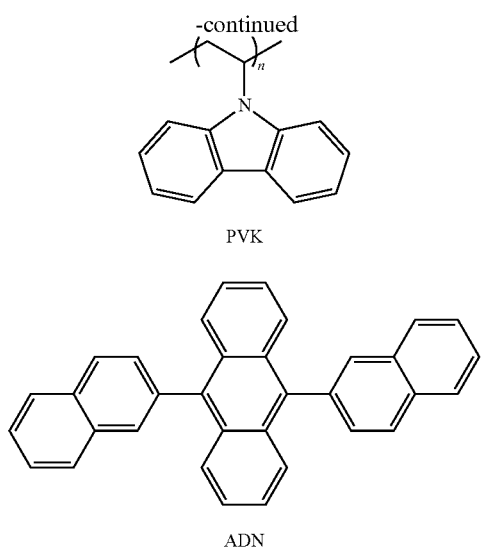

PVK

ADN

The dopant may be at least one of a fluorescent dopant or a phosphorescent dopant. The phosphorescent dopant may be an organic metal complex including Ir, Pt, Os, Re, Ti, Zr, Hf, or a combination of at least two thereof, but is not limited thereto.

Examples of suitable red dopants may include, but are not limited to, PtOEP, Ir(piq)$_3$, and Btp$_2$Ir(acac).

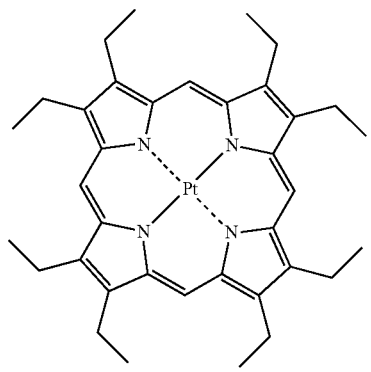

PtOEP

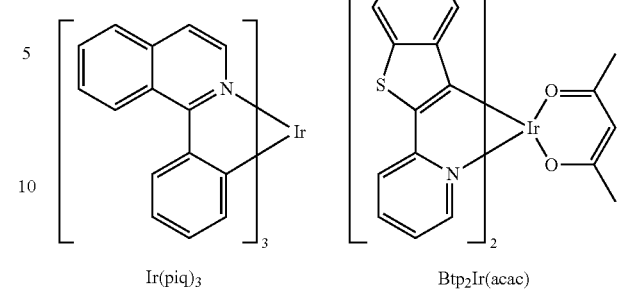

Ir(piq)$_3$      Btp$_2$Ir(acac)

Examples of suitable green dopants may include Ir(ppy)$_3$ (ppy=phenylpyridine), Ir(ppy)$_2$(acac), and Ir(mpyp)$_3$, but are not limited thereto.

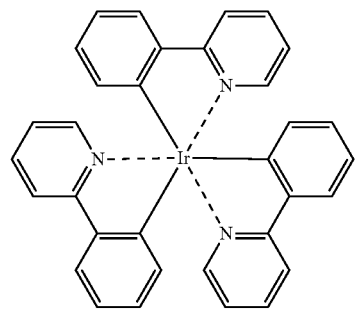

Ir(ppy)$_3$

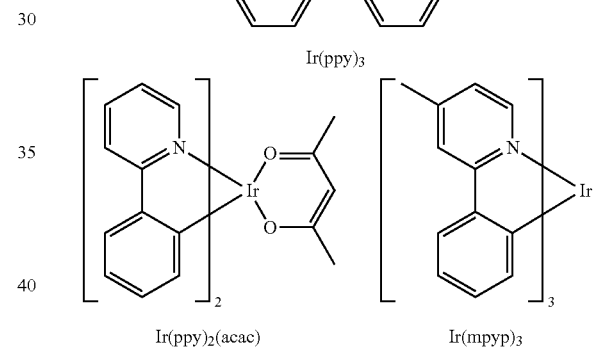

Ir(ppy)$_2$(acac)      Ir(mpyp)$_3$

Examples of suitable blue dopants may include F$_2$Irpic, (F$_2$ppy)$_2$Ir(tmd), Ir(dfppz)$_3$, ter-fluorene, 4,4'-bis(4-diphenylaminostyryl)biphenyl (DPAVBi), and 2,5,8,11-tetra-tert-butyl pherylene (TBPe), but are not limited thereto.

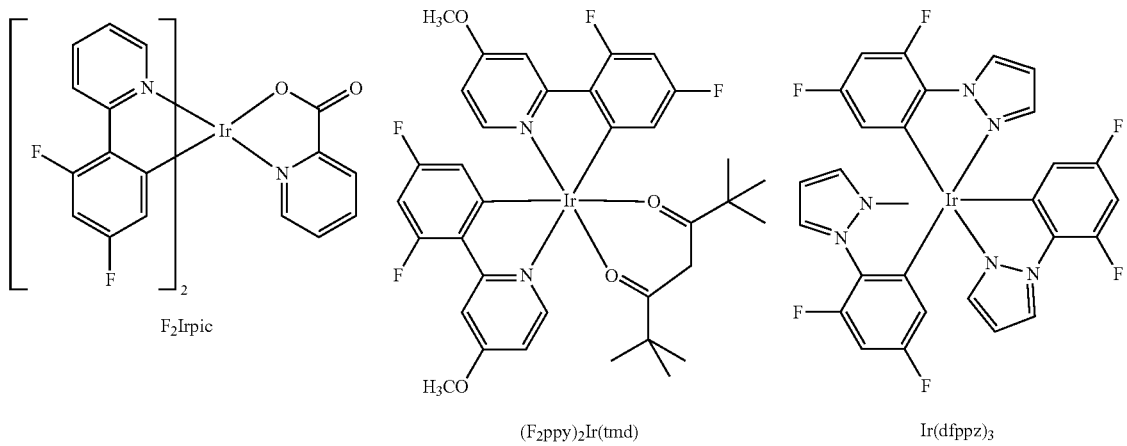

F$_2$Irpic      (F$_2$ppy)$_2$Ir(tmd)      Ir(dfppz)$_3$

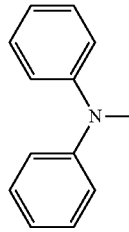
DPAVBi

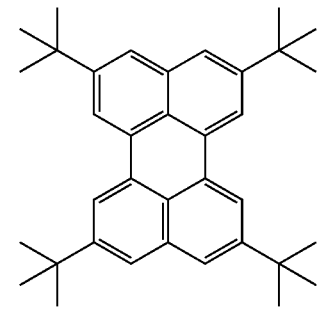
TBPe

When the EML includes both a host and a dopant, an amount of the dopant may be about 0.01 to about 15 parts by weight, based on 100 parts by weight of the host, but is not limited thereto.

The thickness of the EML may be about 100 Å to about 1,000 Å. Maintaining the thickness of the EML at about 100 Å to about 1,000 Å may help ensure that the EML has excellent light emitting ability without a substantial increase in driving voltage. In an implementation, the thickness of the EML may be, e.g., about 200 Å to about 600 Å.

When a phosphorescent dopant is also used to form the EML, a HBL may be formed between the HTL and the EML by using, e.g., vacuum deposition, spin coating, casting, Langmuir-Blodgett (LB) deposition, or the like, in order to prevent diffusion of triplet excitons or holes into an ETL. When the HBL is formed using vacuum deposition or spin coating, the conditions for deposition and coating may be similar to those for the formation of the HIL, although the conditions for deposition and coating may vary according to the material that is used to form the HBL. Any suitable material that is commonly used to form a HBL may be used. Examples of materials for forming the HBL may include an oxadiazole derivative, a triazole derivative, and a phenanthroline derivative, but are not limited thereto.

The thickness of the HBL may about 50 Å to about 1,000 Å. In an implementation, the thickness of the HBL may be, e.g., about 100 Å to about 300 Å. Maintaining the thickness of the HBL at about 50 Å to about 1,000 Å may help ensure that the HBL has an excellent hole blocking ability without a substantial increase in driving voltage.

Then, an ETL may be formed on the HBL or EML by, e.g., vacuum deposition, spin coating, casting, or the like. When the ETL is formed using vacuum deposition or spin coating, the deposition and coating conditions may be similar to those for the formation of the HIL, though the deposition and coating conditions may vary according to the material that is used to form the ETL. A material that is used to form the ETL may be a material that can stably transport electrons injected from the electron injecting electrode (cathode) and any suitable material may be used. Examples of materials for forming the ETL may include a quinoline derivative, such as tris(8-quinolinorate)aluminum (Alq$_3$), TAZ, BAlq, and beryllium bis (benzoquinolin-10-olate (Bebq$_2$), but are not limited thereto.

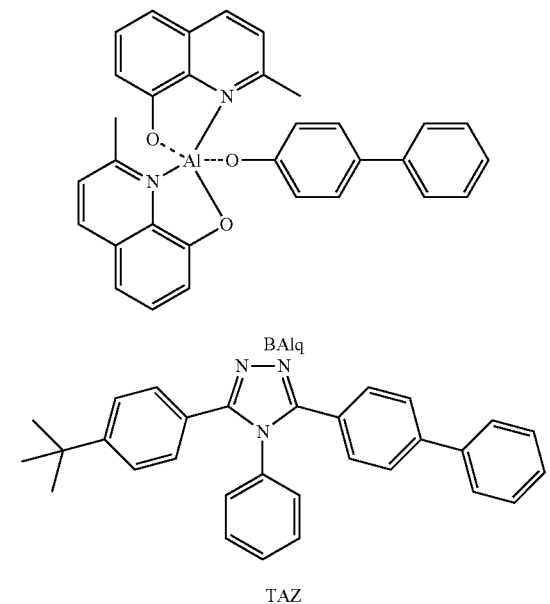
BAlq

TAZ

The thickness of the ETL may be, e.g., about 100 Å to about 1,000 Å. In an implementation, the thickness of the ETL may be, e.g., about 150 Å to about 500 Å. Maintaining the thickness of the ETL at about 100 Å to about 1,000 Å may help ensure that the ETL has satisfactory electron transporting ability without a substantial increase in driving voltage.

Alternatively, the ETL may include an electron transporting organic compound and a metal-containing material. Examples of the electron transporting organic compound unlimitedly include AND(9,10-di(naphthalene-2-il)anthracene); and anthracene-based compounds represented by Compounds 101 or 102 below, but are not limited thereto.

Compound 101

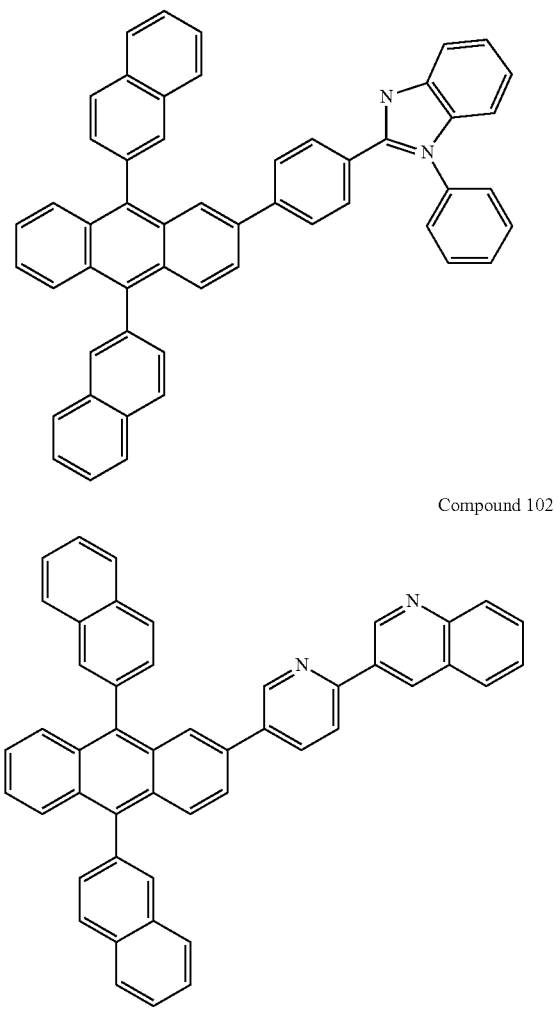

Compound 102

The metal-containing material may include an Li complex. Examples of the Li complex unlimitedly include lithium quinolate (LiQ) or Compound 103 below.

Compound 103

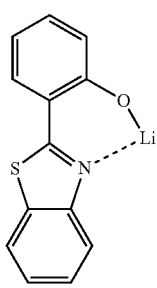

Then, an EIL may be formed on the ETL. The EIL may be formed of any suitable material facilitating injection of electrons from the cathode.

Examples of materials for forming the EIL may include LiF, NaCl, CsF, Li$_2$O, and BaO. The deposition and coating conditions for the EIL may be similar to those for the formation of the HIL, though the deposition and coating conditions may vary according to the material that is used to form the EIL.

The thickness of the EIL may be about 1 Å to about 100 Å. Maintaining the thickness of the EIL at about 1 Å to about 100 Å may help ensure that the EIL has satisfactory electron injection ability without a substantial increase in driving voltage. In an implementation, the thickness of the EIL may be, e.g., about 3 Å to about 90 Å.

Finally, the second electrode 17 may be disposed on the organic layer 15. The second electrode 17 may be a cathode that is an electron injection electrode. A second electrode forming metal may be a metal having a low work function, an alloy having a low work function, an electro-conductive compound, or mixtures thereof. In this regard, the second electrode 17 may be formed of, e.g., lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In an implementation, the transmission electrode may be formed of, e.g., indium tin oxide (ITO) or indium zinc oxide (IZO) to manufacture a top-emission type light-emitting device.

When the first layer from among the OLED is the HIL, the HTL, or the functional layer, the first layer may further include the charge-generating material described above, in addition to the condensed-cyclic compound of Formula 1 above. Alternatively, when the first layer is the EML, the first layer may further include the phosphorescent dopant described above, in addition to the condensed-cyclic compound of Formula 1. As such, the first layer is not limited to the above description Hereinafter, one or more embodiments will be described in detail with reference to the following examples. These examples are not intended to limit the purpose and scope of the one or more embodiments.

EXAMPLE

Synthesis Example 1

Synthesis of Compound 1

Compound F was synthesized through Reaction Scheme 1a below:

Reaction Scheme 1a

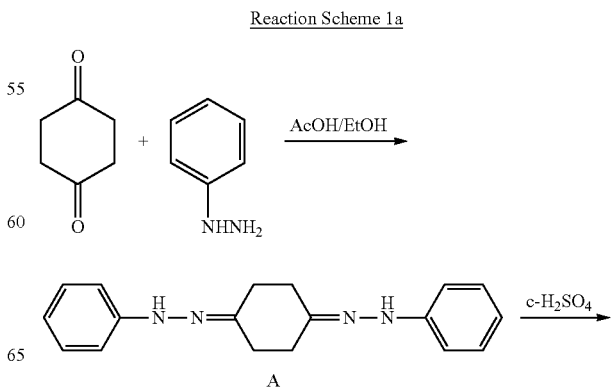

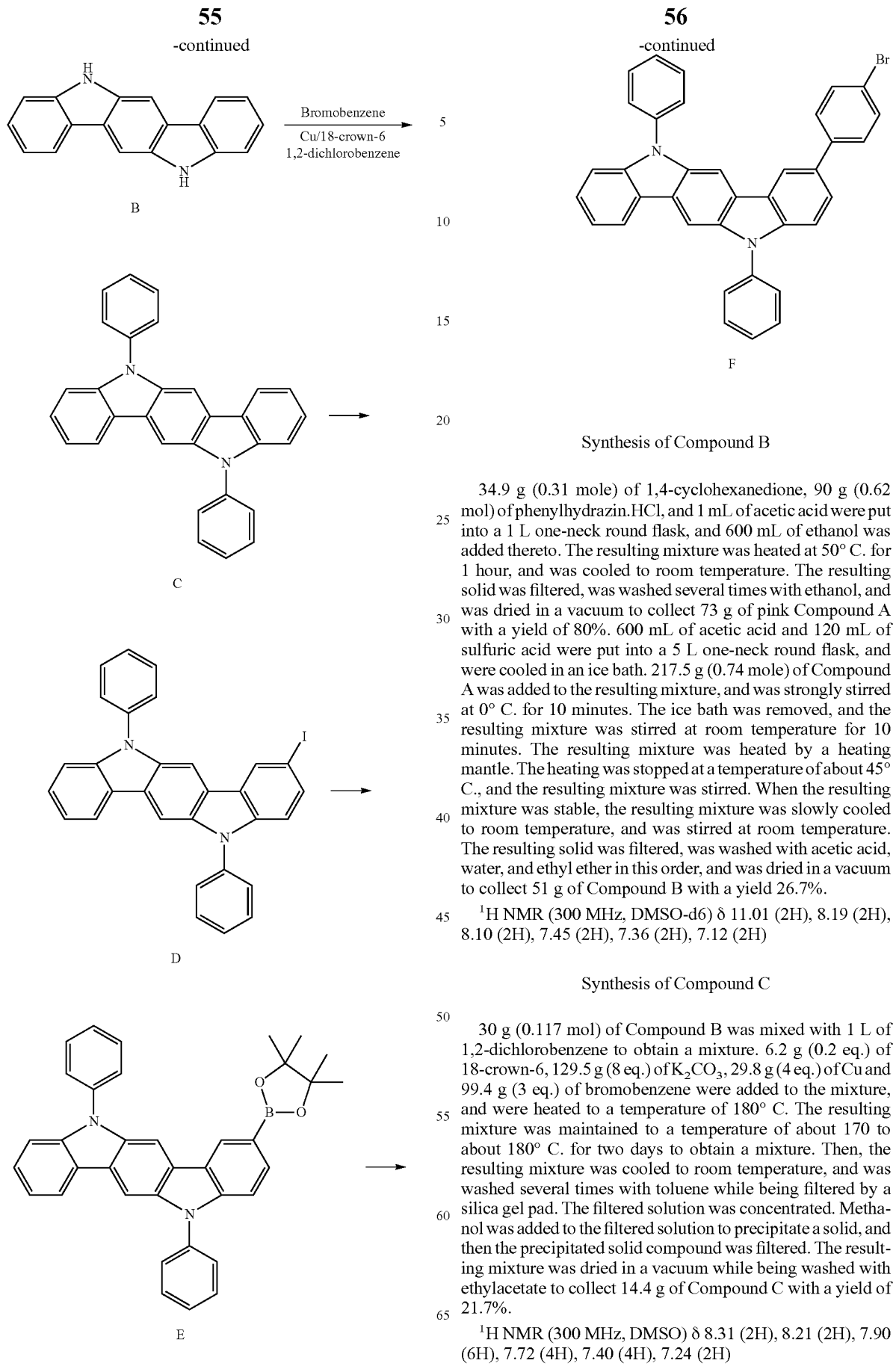

Synthesis of Compound B 34.9 g (0.31 mole) of 1,4-cyclohexanedione, 90 g (0.62 mol) of phenylhydrazin.HCl, and 1 mL of acetic acid were put into a 1 L one-neck round flask, and 600 mL of ethanol was added thereto. The resulting mixture was heated at 50° C. for 1 hour, and was cooled to room temperature. The resulting solid was filtered, was washed several times with ethanol, and was dried in a vacuum to collect 73 g of pink Compound A with a yield of 80%. 600 mL of acetic acid and 120 mL of sulfuric acid were put into a 5 L one-neck round flask, and were cooled in an ice bath. 217.5 g (0.74 mole) of Compound A was added to the resulting mixture, and was strongly stirred at 0° C. for 10 minutes. The ice bath was removed, and the resulting mixture was stirred at room temperature for 10 minutes. The resulting mixture was heated by a heating mantle. The heating was stopped at a temperature of about 45° C., and the resulting mixture was stirred. When the resulting mixture was stable, the resulting mixture was slowly cooled to room temperature, and was stirred at room temperature. The resulting solid was filtered, was washed with acetic acid, water, and ethyl ether in this order, and was dried in a vacuum to collect 51 g of Compound B with a yield 26.7%.

$^1$H NMR (300 MHz, DMSO-d6) δ 11.01 (2H), 8.19 (2H), 8.10 (2H), 7.45 (2H), 7.36 (2H), 7.12 (2H)

Synthesis of Compound C 30 g (0.117 mol) of Compound B was mixed with 1 L of 1,2-dichlorobenzene to obtain a mixture. 6.2 g (0.2 eq.) of 18-crown-6, 129.5 g (8 eq.) of K$_2$CO$_3$, 29.8 g (4 eq.) of Cu and 99.4 g (3 eq.) of bromobenzene were added to the mixture, and were heated to a temperature of 180° C. The resulting mixture was maintained to a temperature of about 170 to about 180° C. for two days to obtain a mixture. Then, the resulting mixture was cooled to room temperature, and was washed several times with toluene while being filtered by a silica gel pad. The filtered solution was concentrated. Methanol was added to the filtered solution to precipitate a solid, and then the precipitated solid compound was filtered. The resulting mixture was dried in a vacuum while being washed with ethylacetate to collect 14.4 g of Compound C with a yield of 21.7%.

$^1$H NMR (300 MHz, DMSO) δ 8.31 (2H), 8.21 (2H), 7.90 (6H), 7.72 (4H), 7.40 (4H), 7.24 (2H)

Synthesis of Compound D 4.08 g (10 mmol) of Compound C was added to 100 mL of 80% acetic acid, and then 1.357 g (5.35 mmol) of Iodine (I$_2$) and 0.333 g (1.46 mmol) of periodic acid (H$_5$IO$_6$) in a solid state were added to the mixture. Then the mixture was stirred at 80° C. for 2 hours in a nitrogen atmosphere. After completion of the reaction, the reaction product was extracted three times with 50 mL of dichloromethane to collect organic layers. The organic layers were dried over magnesium sulfate, and the remaining solvent was evaporated. The residue was isolated and purified using silica gel column chromatography to obtain 6.14 g of Compound D with a yield of 87%.

$^1$H NMR (300 MHz, DMSO) δ 8.28 (1H), 8.25 (1H), 8.06 (1H), 7.90-7.86 (6H), 7.71 (4H), 7.38-7.32 (4H), 7.21 (2H)

Synthesis of Compound F 5.34 g (10 mmol) of Compound D, 0.5 mmol of [1,1'-bis(diphenylphosphino)ferrocene]dichloropalladium(II): PdCl$_2$(dppf)], 2.66 g (10.5 mmol) of bis(pinacolate)diboron, and 3.92 g (20 mmol) of potassium acetate were added to 200 mL of dimethyl sulfoxide (DMSO), and were stirred at 90° C. for 6 hours under a nitrogen atmosphere. The resulting mixture was cooled to room temperature and then was put into 300 mL of water to form white precipitates. The white precipitates were filtered while being washed several times with water to collect a solid compound, and then was dried at a reduced pressure to collect 4.65 g of Compound E with a yield of 87%. Compound E was dissolved in 150 mL of toluene, 2.46 g (8.7 mmol) of 1-bromo-4-iodobenzene, 200 mg (2 mol %) of tetrakis(triphenylphosphane)palladium(0): Pd(PPh$_3$)$_4$, and 2.4 g (17.4 mmol) of K$_2$CO$_3$ aqueous solution were added to the resulting mixture. The resulting mixture was maintained at 80° C. for 6 hours. After completion of the reaction, the reaction product was extracted three times with 50 mL of dichloromethane to collect organic layers. The organic layers were dried over magnesium sulfate, and the remaining solvent was evaporated. The residue was isolated and purified using silica gel column chromatography to obtain 6.2 g of Compound F with a yield of 79%.

$^1$H NMR (300 MHz, DMSO) δ 8.25 (1H), 8.17 (1H), 8.10 (1H), 7.99 (2H), 7.95-7.87 (5H), 7.83-7.80 (6H), 7.76-7.72 (4H), 7.70-7.58 (3H)

Synthesis of Compound 1

Compound 1 was synthesized through Reaction Scheme 1b below:

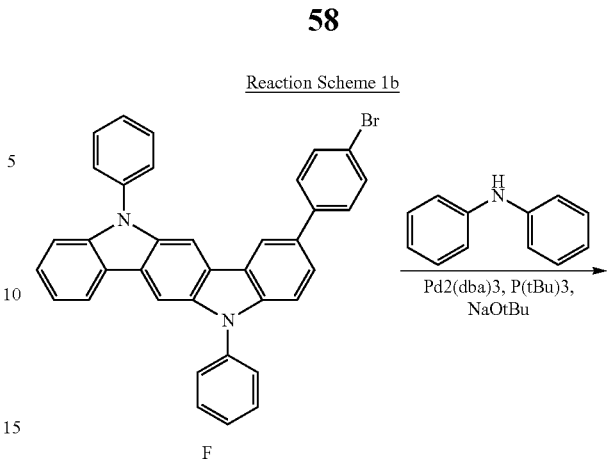

Reaction Scheme 1b

F

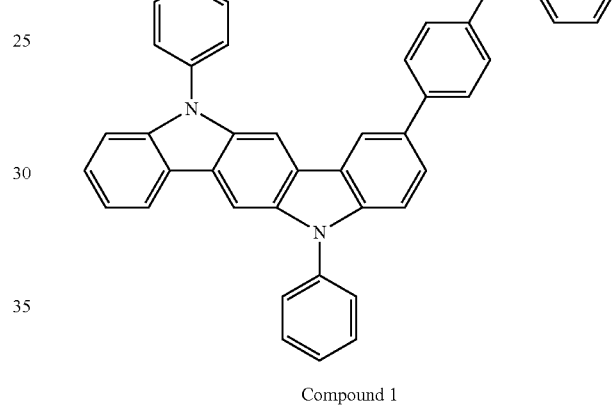

Compound 1

3 g (5.32 mmol) of Compound F and 1.08 g (6.38 mmol) of diphenylamine were dissolved in toluene, and 97.4 mg (0.11 mmol) of tris(dibenzylideneacetone)dipalladium: Pd$_2$(dba)3) and then 22 mg (0.11 mmol) tri(t-butyl)phosphine were added to the resulting mixture under a nitrogen atmosphere. Then, 1.62 g (15.96 mmol) of NaOtBu was added to the resulting mixture, and then was stirred at 80° C. for 4 hours. The resulting mixture was cooled to room temperature and then extracted three times with dichloromethane to collect organic layers. The organic layers were dried over magnesium sulfate, and the remaining solvent was evaporated. The residue was isolated and purified using silica gel column chromatography to obtain 2.64 g of Compound 1 with a yield of 76%.

$^1$H NMR (300 MHz, DMSO) δ 8.25 (1H), 8.14 (2H), 8.06 (1H), 7.97 (2H), 7.88-7.79 (11H), 7.73 (2H), 7.58-7.41 (6H), 7.37 (2H), 7.24 (2H), 7.08-6.96 (4H)

Synthesis Example 2

Synthesis of Compound 3

Compound 3 was synthesized through Reaction Scheme 2 below:

Reaction Scheme 2

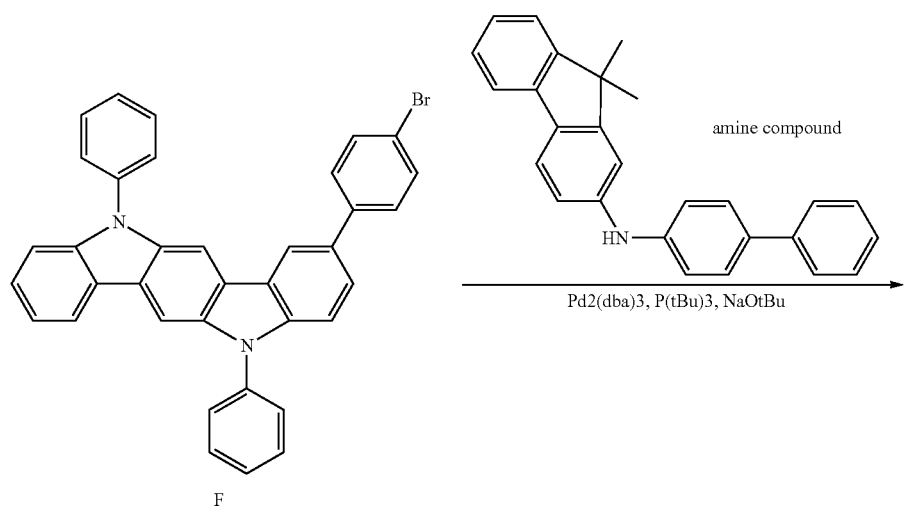

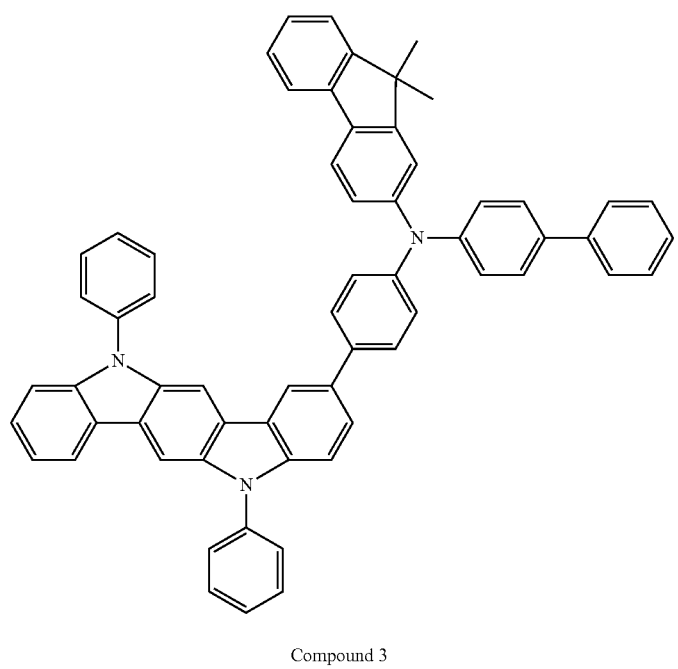

Compound 3

3 g (5.32 mmol) of Compound F and 2.31 g (6.38 mmol) of the amine compound were added to toluene, and then 97.4 mg (0.11 mmol) of tris(dibenzylideneacetone)dipalladium(0): $Pd_2(dba)_3$ and 22 mg (0.11 mmol) of tri(t-butyl)phosphine were added to the resulting mixture in a nitrogen atmosphere. Then, 1.62 g (15.96 mmol) of NaOtBu was added to the resulting mixture, and then was stirred at 80° C. for 4 hours. The resulting mixture was cooled to room temperature and then extracted three times with dichloromethane to collect organic layers. The organic layers were dried over magnesium sulfate, and the remaining solvent was evaporated. The residue was isolated and purified using silica gel column chromatography to obtain 3.11 g of Compound 3 with a yield of 69%.

$^1$H NMR (300 MHz, DMSO) δ 8.34 (1H), 8.27 (1H), 8.09-8.03 (4H), 7.98-7.94 (3H), 7.90-7.88 (3H), 7.82-7.78 (14H), 7.73-7.70 (5H), 7.58-7.50 (2H), 7.23-7.08 (6H), 1.78 (6H)

Synthesis Example 3

Synthesis of Compound 9

Compound 9 was synthesized through Reaction Scheme 3 below:

Reaction Scheme 3

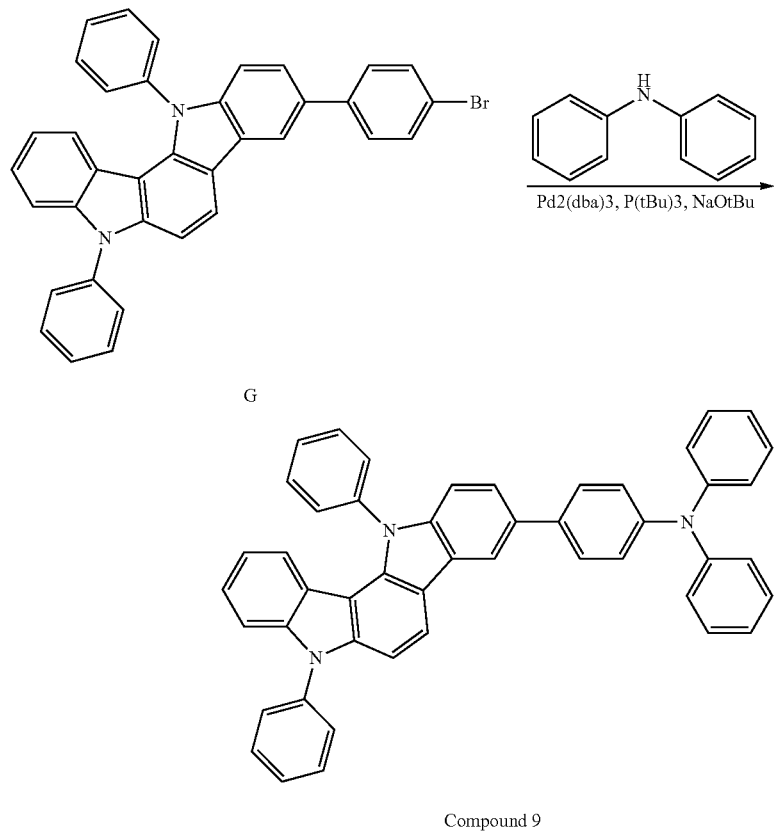

Compound 9 was synthesized in the same manner in Synthesis Example 1, except that 1,3-cyclohexanedione was used instead of 1,4-cyclohexanedione during the synthesis of Compound B of Synthesis Example 1 to synthesize Compound G instead of Compound F, and Compound G was used instead of Compound F.

$^1$H NMR (300 MHz, DMSO) δ 8.37 (1H), 8.03 (1H), 7.96-7.89 (3H), 7.53-7.34 (11H), 7.28 (2H), 7.21-7.09 (7H), 7.05-6.91 (4H), 6.87 (4H),

Synthesis Example 4

Synthesis of Compound 11

Compound 11 was synthesized through Reaction Scheme 4 below:

Reaction Scheme 4

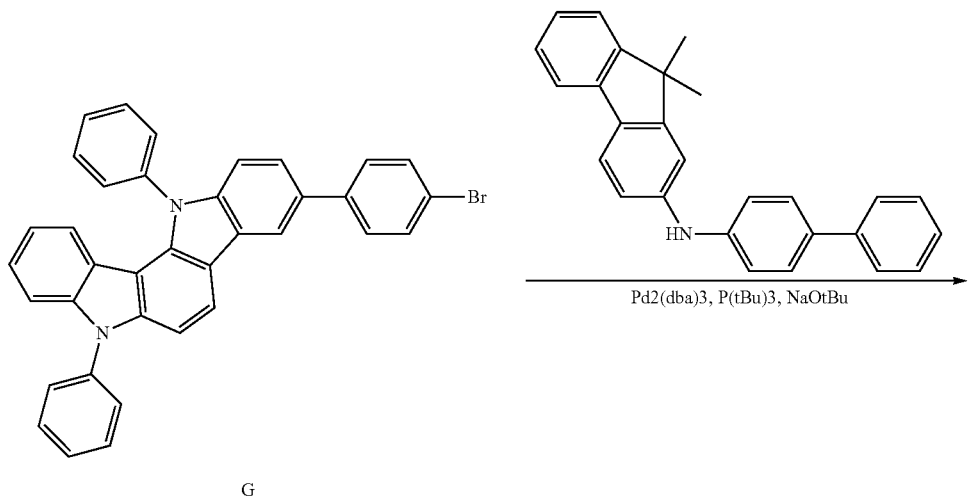

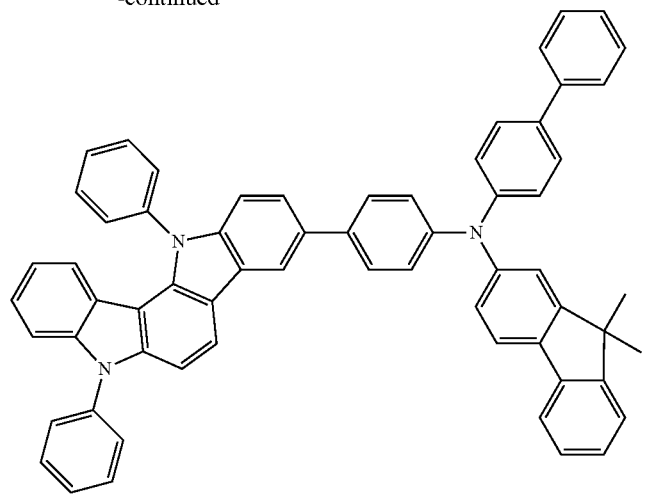

Compound 11

Compound 11 was synthesized in the same manner in Synthesis Example 2, except that 1,3-cyclohexanedione was used instead of 1,4-cyclohexanedione during the synthesis of Compound B of Synthesis Example 2 to synthesis Compound G instead of Compound F, and Compound G was used instead of Compound F.

$^1$H NMR (300 MHz, DMSO) δ 8.36 (1H), 8.28 (1H), 8.11-7.96 (6H), 7.90 (3H), 7.93-7.80 (13H), 7.78-7.66 (6H), 7.58-7.50 (3H), 7 (2H), 1.78 (6H)

Synthesis Example 5

Synthesis of Compound 26

Compound 26 was synthesized through Reaction Scheme 5 below:

Reaction Scheme 5

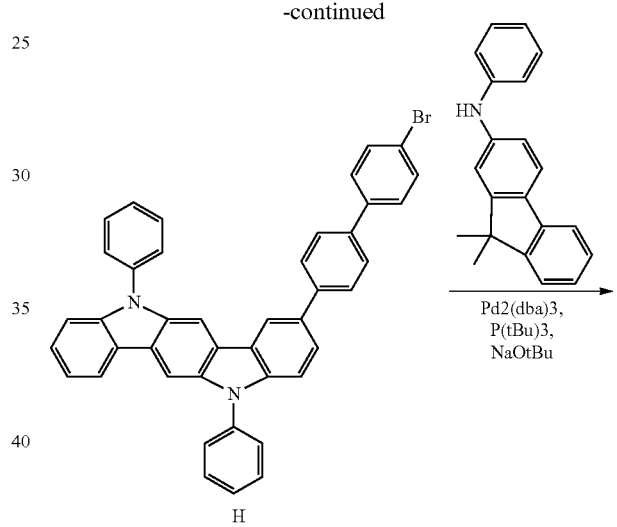

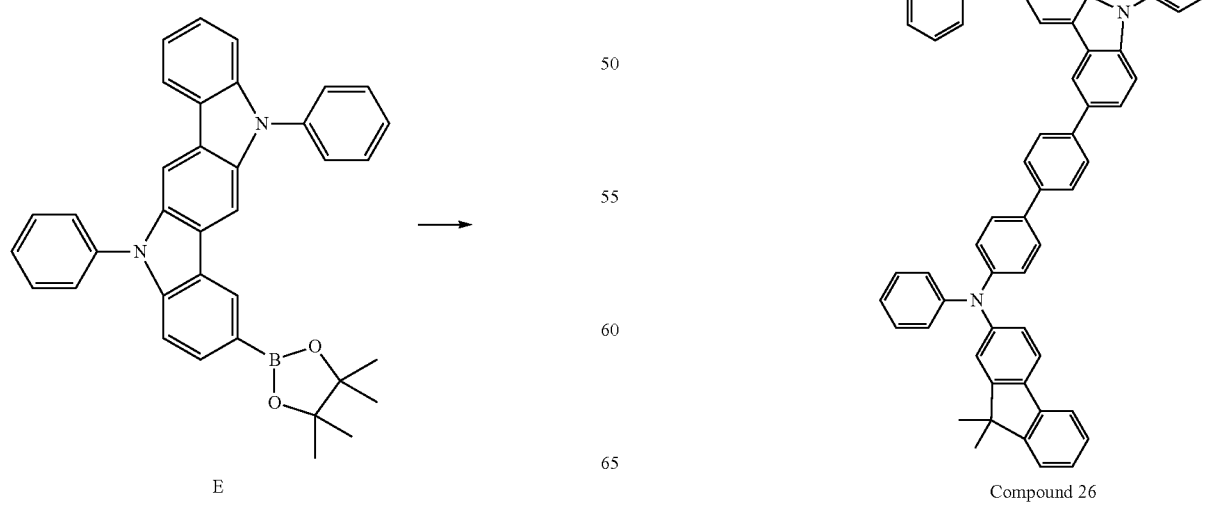

Compound 26

Compound 26 was synthesized in the same manner in Synthesis Example 2, except that Compound H was synthesized by using 4,4'-dibromobiphenyl instead of 1-bromo-4-iodobenzene while synthesizing Compound F in Synthesis Example 1, Compound H was used instead of Compound F in Synthesis Example 2, and the amine compound of Reaction Scheme 5 was used instead of the amine compound of Reaction Scheme 2.

1H NMR (300 MHz, DMSO) δ 8.36 (1H), 8.27 (1H), 7.96-7.82 (4H), 7.73-7.56 (9H), 7.52-7.47 (6H), 7.37-7.25 (8H), 7.19 (2H), 7.07-6.91 (4H), 6.86-6.63 (4H), 1.78 (6H).

Synthesis Example 6

Synthesis of Compound 27

Compound 27 was synthesized through Reaction Scheme 6 below:

Reaction Scheme 6

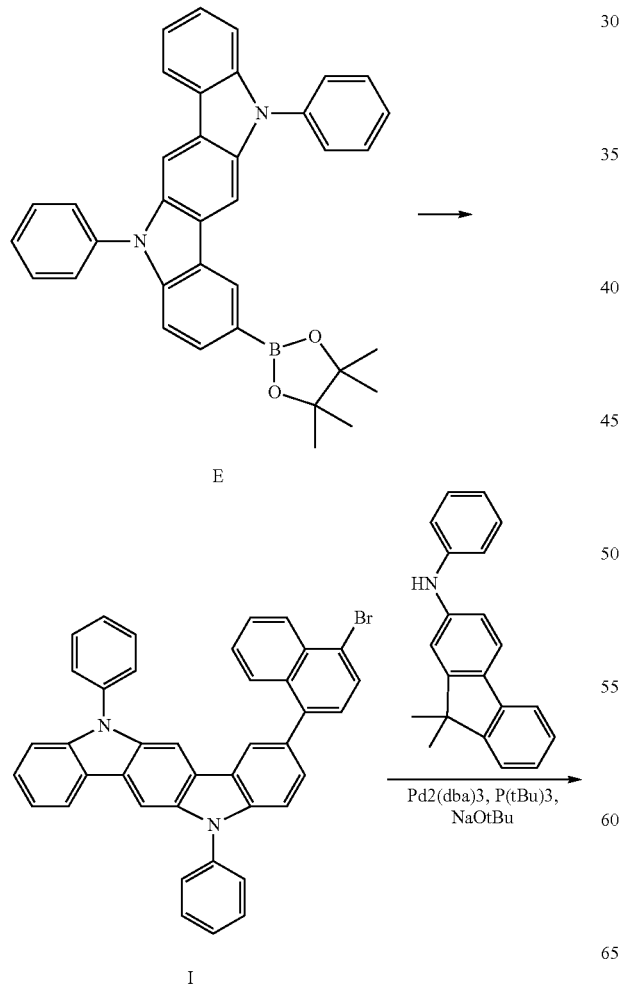

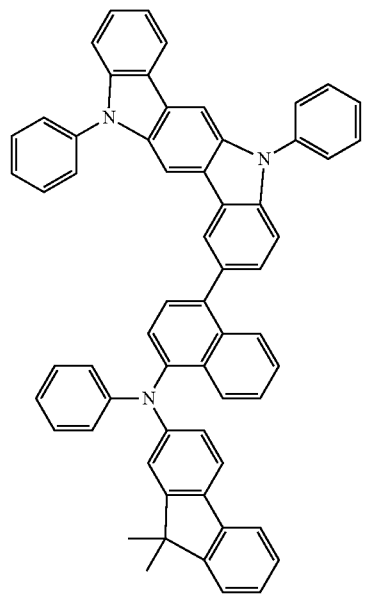

Compound 27

Compound 27 was synthesized in the same manner in Synthesis Example 2, except that Compound I was synthesized by using 1,4-dibronaphthalene instead of 1-bromo-4-iodobenzene while synthesizing Compound F in Synthesis Example 1, Compound I was used instead of Compound F in Synthesis Example 2, and the amine compound of Reaction Scheme 6 was used instead of the amine compound of Reaction Scheme 2.

1H NMR (300 MHz, DMSO) δ 8.53 (1H), 8.42 (1H), 8.12-7.99 (4H), 7.82-7.74 (3H), 7.68-7.59 (5H), 7.52-7.50 (8H), 7.53-7.42 (3H), 7.37-7.23 (6H), 7.11-6.73 (5H), 6.62 (1H), 1.78 (6H)

Comparative Synthesis Example A

Synthesis of Compound A

Compound A was synthesized through Reaction Scheme 7 below:

Reaction Scheme 7
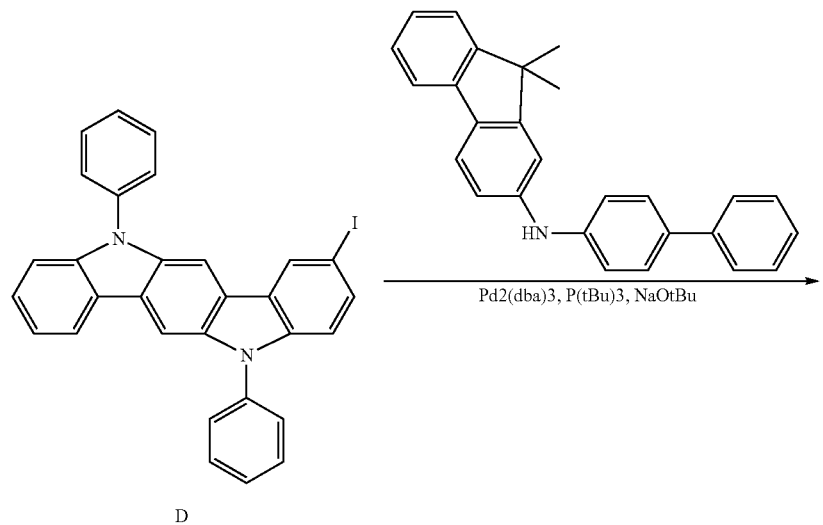
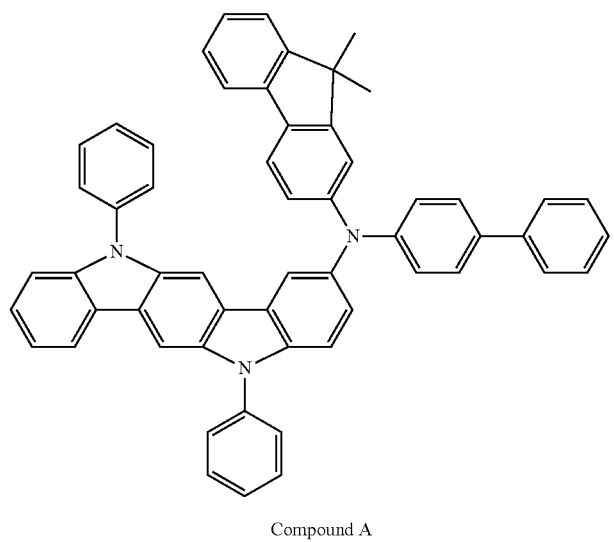
Compound A
Compound A (2.85 g and 70% yield) was synthesized in the same manner in Synthesis Example 2, except that Compound D was used instead of Compound F.
1H MNM (300 MHz, DMSO) δ 8.34 (1H), 8.05 (1H), 7.89 (1H), 7.90-7.64 (3H), 7.61-7.55 (8H), 7.73-7.55 (8H), 7.48-7.35 (6H), 7.31-7.28 (2H), 6.81-6.73 (3H), 6.71 (1H), 6.13 (1H), 1.78 (6H)
Comparative Synthesis Example B
Synthesis of Compound B
Compound B was synthesized through Reaction Scheme 8 below:
Reaction Scheme 8
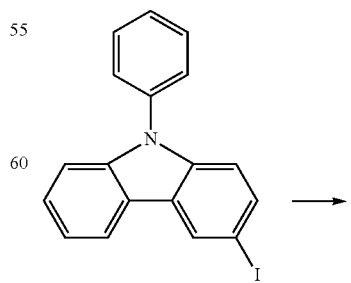

-continued

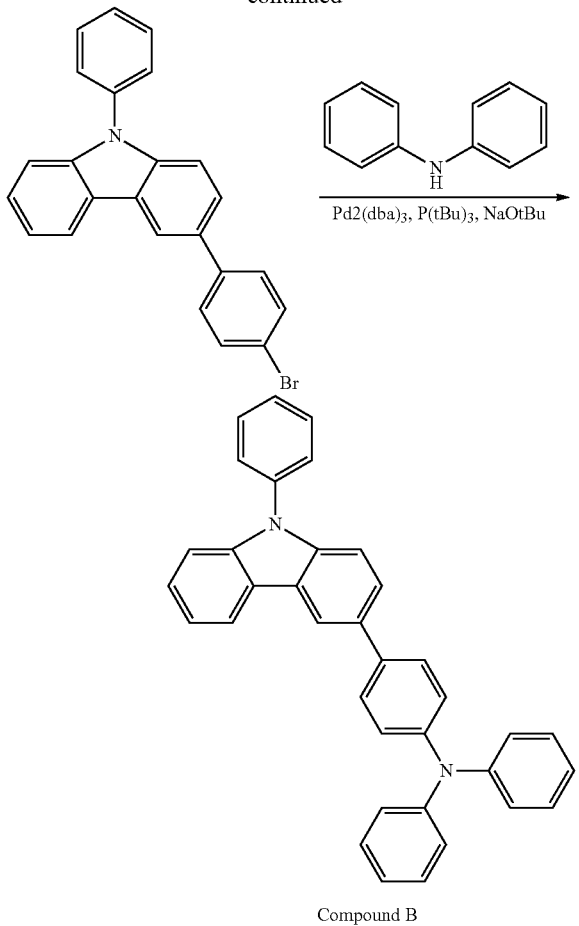

Compound B 5 g (13.5 mmol) of 3-iodin-9-phenylcarbazole and 2.2 g (10.8 mmol) of 4-bromophenyl boronic acid were dissolved in THF, Pd(PPh$_3$)$_4$ (2 mol %) and then an aqueous solution of K$_2$CO$_3$ were added thereto, and the mixture was reacted for 4 hours at 80° C. After the reaction, the mixture was extracted 3 times with 150 mL of dichloromethane, and then residues obtained by drying an acquired organic layer with magnesium sulfate and evaporating a solvent was separated and purified via a silicagel tube chromatography. 4.2 g (10.6 mmol) of the compound obtained as such and 2.2 g (12.7 mmol) of diphenylamine were dissolved in toluene, and 195 mg (0.22 mmol) of tris(dibenzylideneacetone)dipalladium: Pd$_2$(dba)$_3$ and 44 mg (0.22 mmol) of tri(t-butyl)phosphine were added thereto under a nitrogen atmosphere. Then, 3.24 g (31.92 mmol) of NaOtBu was added to the mixture, and stirred for 4 hours at 80° C. The mixture obtained as such was cooled down at room temperature, extracted 3 times with dichloromethane, and then residues obtained by drying an acquired organic layer with magnesium sulfate and evaporating a solvent was separated and purified via a silicagel tube chromatography, thereby obtaining Compound B (4.5 g, 85% yield).

1H NMR (300 MHz, DMSO) δ 8.54 (1H), 7.95 (2H), 7.84-7.78 (2H), 7.66 (2H), 7.62-7.58 (4H), 7.46-7.31 (4H), 7.28-7.21 (5H), 7.06 (2H), 6.89-6.71 (2H), 6.67 (2H)

Example 1

A 15 Ω/cm$^2$ (1200 Å) ITO glass substrate (available from Corning Co.) was cut to a size of 50 mm×50 mm×0.7 mm, ultrasonically washed with isopropyl alcohol for 5 minutes and then with pure water for 5 minutes, and washed again with UV ozone for 30 minutes. Then, m-MTDATA was vacuum-deposited on the ITO to form a HIL having a thickness of 750 Å, and then Compound 1 above was vacuum-deposited on the HIL to form a HTL having a thickness of 150 Å. 97 wt % of DSA as a host and 3 wt % of TBPe as a dopant were deposited on the HTL to form an EML with a thickness of 300 Å. Alq3 was vacuum-deposited on the EML to form an ETL having a thickness of 200 Å. LiF was vacuum-deposited on the ETL to form an EIL having a thickness of 80 Å and Al was vacuum-deposited on the EIL to form a cathode having a thickness of 3,000 Å.

Example 2

An OLED was manufactured in the same manner as in Example 1, except that Compound 3 was used instead of Compound 1 as a material of a HTL.

Example 3

An OLED was manufactured in the same manner as in Example 1, except that Compound 9 was used instead of Compound 1 as a material of a HTL.

Example 4

An OLED was manufactured in the same manner as in Example 1, except that Compound 11 was used instead of Compound 1 as a material of a HTL.

Example 5

An OLED was manufactured in the same manner as in Example 1, except that Compound 26 was used instead of Compound 1 as a material of a HTL.

Example 6

An OLED was manufactured in the same manner as in Example 1, except that Compound 27 was used instead of Compound 1 as a material of a HTL.

Comparative Example 1

An OLED was manufactured in the same manner as in Example 1, except that α-NPD was used instead of Compound 1 as a material of a HTL.

Comparative Example 2

An OLED was manufactured in the same manner as in Example 1, except that Compound A was used instead of Compound 1 as a material of a HTL.

Comparative Example 3

An OLED was manufactured in the same manner as in Example 1, except that Compound B was used instead of Compound 1 as a material of a HTL.

Evaluation Example

Luminescent efficiency and half lifetime (at initial brightness of 1000 nit) of the OLEDs manufactured in Examples 1 through 6 and Comparative Examples 1 through 3 were evaluated by using a PR650 Spectroscan Source Measurement Unit (available from PhotoResearch company). The results are shown in Table 1 below:

TABLE 1

|  | HTL Compound | Luminescent Efficiency (cd/A) | Half Lifetime (Time) @1000 nit |
|---|---|---|---|
| Example 1 | Compound 1 | 4.39 | 10000 |
| Example 2 | Compound 3 | 4.76 | 8900 |
| Example 3 | Compound 9 | 4.63 | 7900 |
| Example 4 | Compound 11 | 4.75 | 9500 |
| Example 5 | Compound 26 | 4.25 | 9600 |
| Example 6 | Compound 27 | 4.59 | 8200 |
| Comparative Example 1 | α-NPD | 3.86 | 4600 |
| Comparative Example 2 | Compound A | 4.03 | 2000 |
| Comparative Example 3 | Compound B | 3.12 | 5300 |

Referring to Table 1, the OLEDs of Examples 1 through 6 were found to have improved efficiencies and lifetime characteristics, as compared to the OLED of Comparative Examples 1 through 3.

The OLED including the condensed-cyclic compound represented by Formula 1 may have excellent performance, for example, high efficiencies and long lifetime.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A condensed-cyclic compound represented by Formula 1 below:

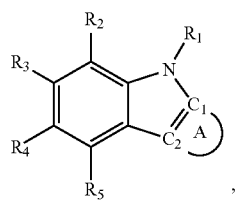

Formula 1 wherein, in Formula 1:
ring A is represented by Formula 2 below or Formula 3 below:

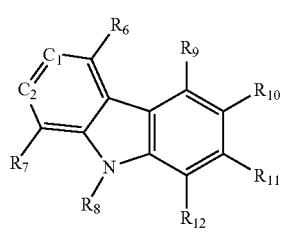

Formula 2

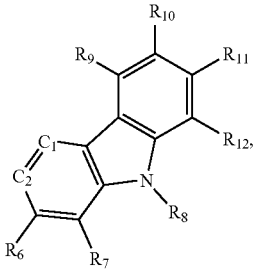

Formula 3

$R_1$ through $R_{12}$ are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a first substituent represented by —$(Ar_1)_a$—$Ar_{11}$, a second substituent represented by —N[—$(Ar_2)_b$—$Ar_{12}$][—$(Ar_3)_c$—$Ar_{13}$], or a third substituent represented by —$(Ar_4)_d$—N[—$(Ar_5)_e$—$Ar_{15}$][—$(Ar_6)_f$—$Ar_{16}$], at least one of $R_1$ through $R_{12}$ is the third substituent;

$Ar_1$ through $Ar_6$, among the first through third substituents, are each independently a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, or a substituted or unsubstituted $C_3$-$C_{30}$ heteroarylene group;

$Ar_{11}$, $Ar_{12}$, $Ar_{13}$, $Ar_{15}$, and $Ar_{16}$, among the first to third substituents, are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group or a substituted or unsubstituted $C_3$-$C_{30}$ heteroaryl group;

a, b, c, e, and f are each independently an integer of 0 to 10;
d is an integer of 1 to 10; and "a" groups of $Ar_1$ in the group of —$(Ar_1)_a$—$Ar_{11}$ of the first substituent are identical to or different from each other; "b" groups of $Ar_2$ in the group of —$(Ar_2)_b$—$Ar_{12}$ of the second substituent are identical to or different from each other; "c" groups of $Ar_3$ in the group of —$(Ar_3)_c$—$Ar_{13}$ of the second substituent are identical to or different from each other; "e" groups of $Ar_5$ in the group of —$(Ar_5)_e$—$Ar_{15}$ of the third substituent are identical to or different from each other; and "f" groups of $Ar_6$ in the group of —$(Ar_6)_f$—$Ar_{16}$ of the third substituent are identical to or different from each other.

2. The condensed-cyclic compound as claimed in claim 1, wherein $Ar_1$ through $Ar_6$ are each independently a substituted or unsubstituted $C_5$-$C_{14}$ arylene group or a substituted or unsubstituted $C_3$-$C_{14}$ heteroarylene group.

3. The condensed-cyclic compound as claimed in claim 1, wherein $Ar_1$ through $Ar_6$ are each independently a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di(C₁-C₁₀ alkyl)fluorenylene group, a (C₆-C₁₄ aryl)fluorenylene group, a di(C₆-C₁₄ aryl)fluorenylene group, a naphthylene group, a C₁-C₁₀ alkylnaphthylene group, a di(C₁-C₁₀ alkyl)naphthylene group, a (C₆-C₁₄ aryl)naphthylene group, a di(C₆-C₁₄ aryl)naphthylene group, an anthrylene group, a C₁-C₁₀ alkylanthrylene group, a di(C₁-C₁₀ alkyl)anthrylene group, a (C₆-C₁₄ aryl)anthrylene group, a di(C₆-C₁₄ aryl)anthrylene group, a pyridinylene group, a C₁-C₁₀ alkylpyridinylene group, a di(C₁-C₁₀ alkyl)pyridinylene group, a (C₆-C₁₄ aryl)pyridinylene group, a di(C₆-C₁₄ aryl)pyridinylene group, a quinolinylene group, a C₁-C₁₀ alkylquinolinylene group, a di(C₁-C₁₀ alkyl)quinolinylene group, a (C₆-C₁₄ aryl)quinolinylene group, a di(C₆-C₁₄ aryl)quinolinylene group, a benzoimidazolylene group, a C₁-C₁₀ alkylbenzoimidazolylene group, a di(C₁-C₁₀ alkyl)benzoimidazolylene group, a (C₆-C₁₄ aryl)benzoimidazolylene group, a di(C₆-C₁₄ aryl)benzoimidazolylene group, an imidazopyridinylene group, a C₁-C₁₀ alkylimidazopyridinylene group, a di(C₁-C₁₀ alkyl)imidazopyridinylene group, a (C₆-C₁₄ aryl)imidazopyridinylene group, a di(C₆-C₁₄aryl)imidazopyridinylene group, an imidazopyrimidinylene group, a C₁-C₁₀ alkylimidazopyrimidinylene group, a di(C₁-C₁₀ alkyl)imidazopyrimidinylene group, a (C₆-C₁₄ aryl)imidazopyrimidinylene group, or a di(C₆-C₁₄ aryl)imidazopyrimidinylene group.

4. The condensed-cyclic compound as claimed in claim 1, wherein $Ar_{11}$, $Ar_{12}$, $Ar_{13}$, $Ar_{15}$, and $Ar_{16}$ are each independently a hydrogen atom, a heavy hydrogen atom, a halogen atom, a hydroxyl group, a cyano group, a substituted or unsubstituted C₁-C₁₀ alkyl group, a substituted or unsubstituted C₂-C₁₀ alkenyl group, a substituted or unsubstituted C₂-C₁₀ alkynyl group, a substituted or unsubstituted C₁-C₁₀ alkoxy group, a substituted or unsubstituted C₅-C₁₄ aryl group, or a substituted or unsubstituted C₃-C₁₄ heteroaryl group.

5. The condensed-cyclic compound as claimed in claim 1, wherein $Ar_{11}$, $Ar_{12}$, $Ar_{13}$, $Ar_{15}$, and $Ar_{16}$ are each independently a hydrogen atom, a heavy hydrogen atom, a halogen atom, a hydroxyl group, a cyano group, a methyl group, an ethyl group, a propyl group, a buthyl group, penthyl group, an ethenyl group, a prophenyl group, a butenyl group, a pentenyl group, an acethly group, a methoxy group, an ethoxy group, a propoxy group, a butoxy group, a pentoxy group, a phenyl group, a C₁-C₁₀alkyl phenyl group, a di(C₁-C₁₀alkyl)phenyl group, a (C₆-C₁₄aryl)phenyl group, a di(C₆-C₁₄aryl)phenyl group, a carbazolyl group, a C₁-C₁₀alkyl carbazolyl group, a di(C₁-C₁₀alkyl)carbazolyl group, a C₆-C₁₄aryl carbazolyl group, a di(C₆-C₁₄aryl)carbazolyl group, a fluorenyl group, a C₁-C₁₀alkylfluorenyl group, a di(C₁-C₁₀alkyl)fluorenyl group, a (C₆-C₁₄aryl)fluorenyl group, a di(C₆-C₁₄aryl)fluorenyl group, a naphthyl group, a C₁-C₁₀alkylnaphthyl group, a di(C₁-C₁₀alkyl)naphthyl group, a (C₆-C₁₄aryl)naphthyl group, a di(C₆-C₁₄aryl)naphthyl group, an anthryl group, a C₁-C₁₀alkylanthryl group, a di(C₁-C₁₀alkyl)anthryl group, a (C₆-C₁₄aryl)anthryl group, a di(C₆-C₁₄aryl)anthryl group, a pyridinyl group, a pyridinylene group, a C₁-C₁₀alkylpyridinyl group, a di(C₁-C₁₀alkyl)pyridinyl group, a (C₆-C₁₄aryl)pyridinyl group, a di(C₆-C₁₄aryl)pyridinyl group, a quinolinyl group, a C₁-C₁₀alkylquinolinyl group, a di(C₁-C₁₀alkyl)quinolinyl group, a (C₆-C₁₄aryl)quinolinyl group, a di(C₆-C₁₄aryl)quinolinyl group, a benzoimidazolyl group, a C₁-C₁₀alkylbenzoimidazolyl group, a di(C₁-C₁₀alkyl)benzoimidazolyl group, a (C₆-C₁₄aryl)benzoimidazolyl group, a di(C₆-C₁₄aryl)benzoimidazolyl group, an imidazopyridinyl group, a C₁-C₁₀alkylimidazopyridinyl group, a di(C₁-C₁₀alkyl)imidazopyridinyl group, a (C₆-C₁₄aryl)imidazopyridinyl group, a di(C₆-C₁₄aryl)imidazopyridinyl group, a (C₆-C₁₄aryl)imida-zopyridinyl group, an imidazopyrimidinyl group, a C₁-C₁₀alkylimidazopyrimidinyl group, a di(C₁-C₁₀alkyl)imidazopyrimidinyl group, a (C₆-C₁₄aryl)imidazopyrimidinyl group, or a di(C₆-C₁₄aryl)imidazopyrimidinyl group.

6. The condensed-cyclic compound as claimed in claim 1, wherein $Ar_{11}$, $Ar_{12}$, $Ar_{13}$, $Ar_{15}$, and $Ar_{16}$ are each independently represented by any one of Formulae 4A through 4G below:

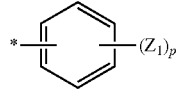

Formula 4A

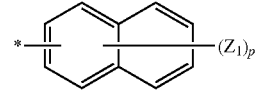

Formula 4B

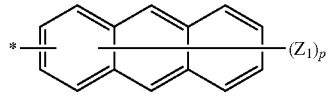

Formula 4C

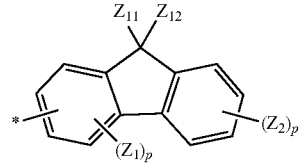

Formula 4D

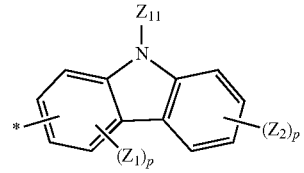

Formula 4E

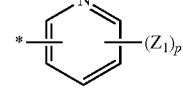

Formula 4F

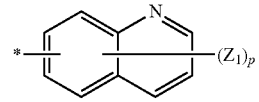

Formula 4G and
wherein, in Formulae 4A to 4G:
$Z_1$, $Z_2$, $Z_{11}$, and $Z_{12}$ are each independently a hydrogen atom, a heavy hydrogen atom, a C₁-C₁₀alkyl group, a C₁-C₁₀ alkoxy group, or a C₆-C₁₄ aryl group,
p and q are each independently an integer of 1 to 8, and
* is a bonding site with $Ar_1$, $Ar_2$, $Ar_3$, $Ar_5$, or $Ar_6$.

7. The condensed-cyclic compound as claimed in claim 1, wherein $Ar_{11}$, $Ar_{12}$, $Ar_{13}$, $Ar_{15}$, and $Ar_{16}$ are each independently represented by any one of Formula 5A through 5E below:

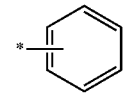

Formula 5A

-continued

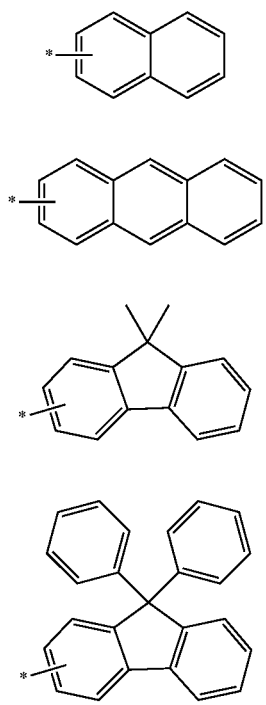

Formula 5B

Formula 5C

Formula 5D

Formula 5E and wherein, in Formulae 5A to 5E, * is a bonding site with $Ar_1$, $Ar_2$, $Ar_3$, $Ar_5$, or $Ar_6$.

8. The condensed-cyclic compound as claimed in claim 1, wherein:

a, b, c, e, and f are each independently 0, 1, 2, or 3, and d is 1, 2, or 3.

9. The condensed-cyclic compound as claimed in claim 1, wherein the second substituent and —N[—$(Ar_5)_e$—$Ar_{15}$][—$(Ar_6)_f$—$Ar_{16}$] of the third substituent are each independently represented by any one of Formulae 6A through 6K below:

Formula 6A

Formula 6B

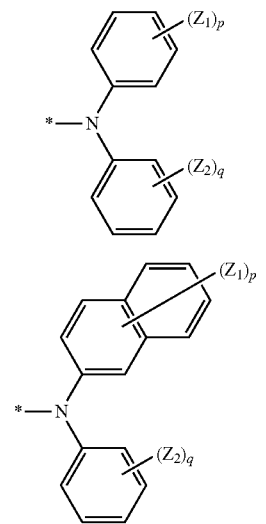

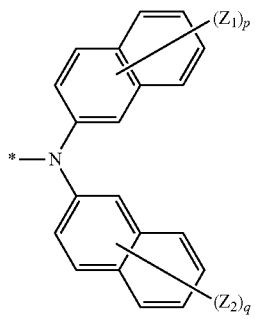

Formula 6C

Formula 6D

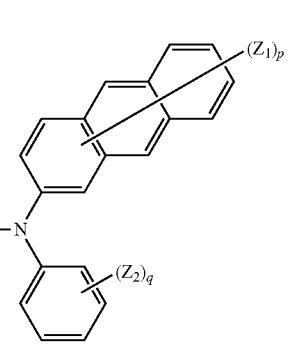

Formula 6E

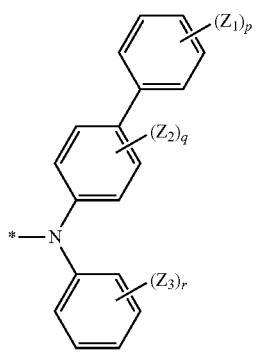

Formula 6F

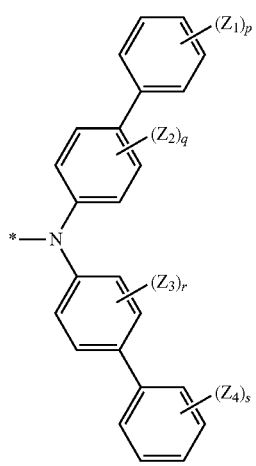

-continued

Formula 6G

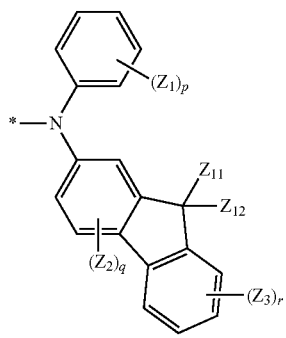

Formula 6H

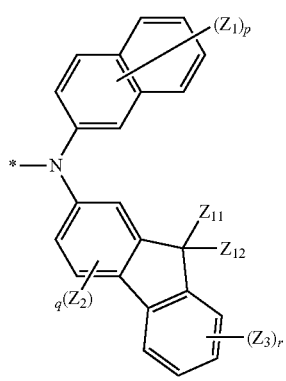

Formula 6I

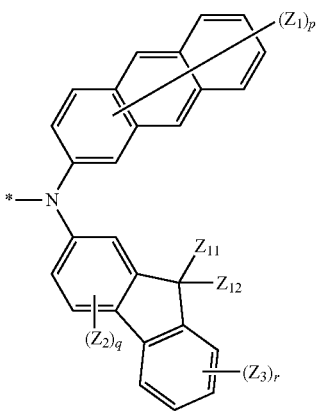

Formula 6J

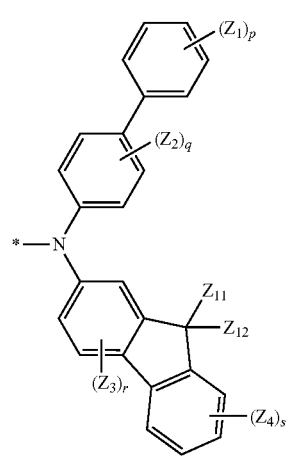

-continued

Formula 6K

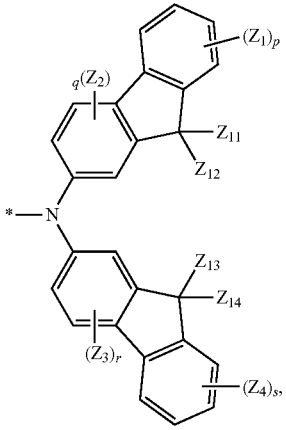

and
wherein, in Formulae 6A to 6K:
Z$_1$ through Z$_4$ and Z$_{11}$ through Z$_{14}$ are each independently a hydrogen atom, a heavy hydrogen atom, a C$_1$-C$_{10}$ alkyl group, a C$_1$-C$_{10}$ alkoxy group, or a C$_6$-C$_{14}$ aryl group,
p, q, r, and s are each independently an integer of 1 to 8, and
is a bonding site with Ar$_4$ or with a ring atom constituting a backbone of Formula 1.

10. The condensed-cyclic compound as claimed in claim 1, wherein R$_1$ through R$_{12}$ are each independently a hydrogen atom, a heavy hydrogen atom, a halogen atom, a hydroxyl group, a cyano group, the first substituent, the second substituent, or the third substituent; "a" in the first substituent is 0; "b" and "c" in the second substituent are each 0 or 1; d in the third substituent is 1 or 2, and e and f in the third substituent are each independently 0 or 1; Ar$_2$ through Ar$_6$, among the first substituent through the third substituent, are each independently a substituted or unsubstituted C$_5$-C$_{14}$ arylene group or a substituted or unsubstituted C$_3$-C$_{14}$ heteroarylene group; and Ar$_{11}$, Ar$_{12}$, Ar$_{13}$, Ar$_{15}$, and Ar$_{16}$, among the first substituent through the third substituent, are each independently a hydrogen atom, a heavy hydrogen atom, a halogen atom, a hydroxyl group, a cyano group, a substituted or unsubstituted C$_1$-C$_{10}$ alkyl group, a substituted or unsubstituted C$_2$-C$_{10}$ alkenyl group, a substituted or unsubstituted C$_2$-C$_{10}$ alkynyl group, a substituted or unsubstituted C$_1$-C$_{10}$ alkoxy group, a substituted or unsubstituted C$_5$-C$_{14}$ aryl group, or a substituted or unsubstituted C$_3$-C$_{14}$ heteroaryl group.

11. The condensed-cyclic compound as claimed in claim 1, wherein R$_1$ through R$_{12}$ are each independently a hydrogen atom, a heavy hydrogen atom, a halogen atom, a hydroxyl group, a cyano group, the first substituent, the second substituent, or the third substituent; "a" in the first substituent is 0; "b" and "c" in the second substituent are each independently 0 or 1; "d" of the third substituent is 1 or 2, and "e" and "f" in the third substituent are each independently 0 or 1; Ar$_2$ through Ar$_6$, among the first substituent through the third substituent, are each independently a phenylene group, a C$_1$-C$_{10}$ alkylphenylene group, a di(C$_1$-C$_{10}$ alkyl)phenylene group, a (C$_6$-C$_{14}$ aryl)phenylene group, a di(C$_6$-C$_{14}$ aryl)phenylene group, a carbazolylene group, a C$_1$-C$_{10}$ alkylcarbazolylene group, a di(C$_1$-C$_{10}$ alkyl)carbazolylene group, a C$_6$-C$_{14}$ arylcarbazolylene group, a di(C$_6$-C$_{14}$ aryl)carbazolylene group, a fluorenylene group, a C$_1$-C$_{10}$ alkylfluorenylene group, a di(C₁-C₁₀ alkyl)fluorenylene group, a (C₆-C₁₄ aryl)fluorenylene group, a di(C₆-C₁₄ aryl)fluorenylene group, a naphthylene group, a C₁-C₁₀ alkylnaphthylene group, a di(C₁-C₁₀ alkyl)naphthylene group, a (C₆-C₁₄ aryl)naphthylene group, a di(C₆-C₁₄ aryl)naphthylene group, an anthrylene group, a C₁-C₁₀ alkylanthrylene group, a di(C₁-C₁₀ alkyl)anthrylene group, a (C₆-C₁₄ aryl)anthrylene group, a di(C₆-C₁₄ aryl)anthrylene group, a pyridinylene group, a C₁-C₁₀ alkylpyridinylene group, a di(C₁-C₁₀ alkyl)pyridinylene group, a (C₆-C₁₄ aryl)pyridinylene group, a di(C₆-C₁₄ aryl)pyridinylene group, a quinolinylene group, a C₁-C₁₀ alkyl quinolinylene group, a di(C₁-C₁₀ alkyl)quinolinylene group, a (C₆-C₁₄ aryl)quinolinylene group, a di(C₆-C₁₄ aryl)quinolinylene group, a benzoimidazolylene group, a C₁-C₁₀ alkylbenzoimidazolylene group, a di(C₁-C₁₀ alkyl)benzoimidazolylene group, a (C₆-C₁₄ aryl)benzoimidazolylene group, a di(C₆-C₁₄ aryl)benzoimidazolylene group, an imidazopyridinylene group, a C₁-C₁₀ alkylimidazopyridinylene group, a di(C₁-C₁₀ alkyl)imidazopyridinylene group, a (C₆-C₁₄ aryl) imidazopyridinylene group, a di(C₆-C₁₄ aryl) imidazopyridinylene group, an imidazopyrimidinylene group, a C₁-C₁₀ alkylimidazopyrimidinylene group, a di(C₁-C₁₀ alkyl) imidazopyrimidinylene group, a (C₆-C₁₄ aryl)imidazopyrimidinylene group, or a di(C₆-C₁₄ aryl)imidazopyrimidinylene group; $Ar_{11}$, $Ar_{12}$, $Ar_{13}$, $Ar_{15}$, and $Ar_{16}$, among the first substituent through the third substituent, are each independently a hydrogen atom, a heavy hydrogen atom, a halogen atom, a hydroxyl group, a cyano group, a methyl group, an ethyl group, a propyl group, a butyl group, pentyl group, an ethenyl group, a propenyl group, a butenyl group, a pentenyl group, an acetly group, a methoxy group, an ethoxy group, a propoxy group, a butoxy group, a pentoxy group, a phenyl group, a C₁-C₁₀ alkylphenyl group, a di(C₁-C₁₀ alkyl)phenyl group, a (C₆-C₁₄ aryl)phenyl group, a di(C₆-C₁₄ aryl)phenyl group, a carbazolyl group, a C₁-C₁₀ alkyl carbazolyl group, a di(C₁-C₁₀ alkyl)carbazolyl group, a C₆-C₁₄ arylcarbazolyl group, a di(C₆-C₁₄ aryl) carbazolyl group, a fluorenyl group, a C₁-C₁₀ alkylfluorenyl group, a di(C₁-C₁₀ alkyl)fluorenyl group, a (C₆-C₁₄ aryl)fluorenyl group, a di(C₆-C₁₄ aryl)fluorenyl group, a naphthyl group, a C₁-C₁₀ alkylnaphthyl group, a di(C₁-C₁₀ alkyl)naphthyl group, a (C₆-C₁₄ aryl)naphthyl group, a di(C₆-C₁₄ aryl)naphthyl group, an anthryl group, a C₁-C₁₀ alkylanthryl group, a di(C₁-C₁₀ alkyl)anthryl group, a (C₆-C₁₄ aryl)anthryl group, a di(C₆-C₁₄ aryl)anthryl group, a pyridinyl group, a C₁-C₁₀ alkylpyridinyl group, a di(C₁-C₁₀ alkyl)pyridinyl group, a (C₆-C₁₄ aryl)pyridinyl group, a di(C₆-C₁₄ aryl)pyridinyl group, a quinolinyl group, a C₁-C₁₀ alkylquinolinyl group, a di(C₁-C₁₀ alkyl)quinolinyl group, a (C₆-C₁₄ aryl)quinolinyl group, a di(C₆-C₁₄ aryl)quinolinyl group, a benzoimidazolyl group, a C₁-C₁₀ alkylbenzoimidazolyl group, a di(C₁-C₁₀ alkyl)benzoimidazolyl group, a (C₆-C₁₄ aryl)benzoimidazolyl group, a di(C₆-C₁₄ aryl)benzoimidazolyl group, an imidazopyridinyl group, a C₁-C₁₀ alkylimidazopyridinyl group, a di(C₁-C₁₀ alkyl) imidazopyridinyl group, a (C₆-C₁₄ aryl) imidazopyridinyl group, a di(C₆-C₁₄ aryl) imidazopyridinyl group, an imidazopyrimidinyl group, a C₁-C₁₀ alkylimidazopyrimidinyl group, a di(C₁-C₁₀ alkyl)imidazopyrimidinyl group, a (C₆-C₁₄ aryl)imidazopyrimidinyl group, or a di(C₆-C₁₄ aryl) imidazopyrimidinyl group.

12. The condensed-cyclic compound as claimed in claim 1, wherein the condensed-cyclic compound represented by Formula 1 is represented by any one of Formulae 2a through 2d below:

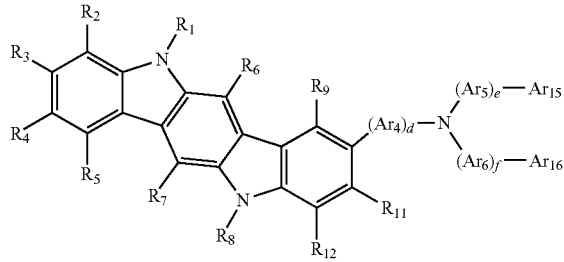

Formula 2a

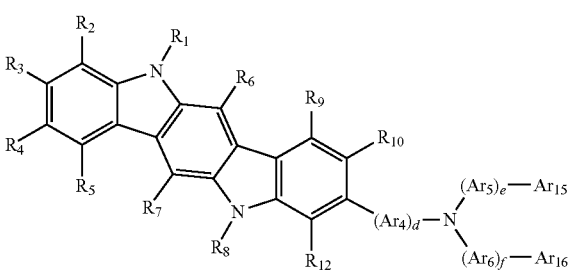

Formula 2b

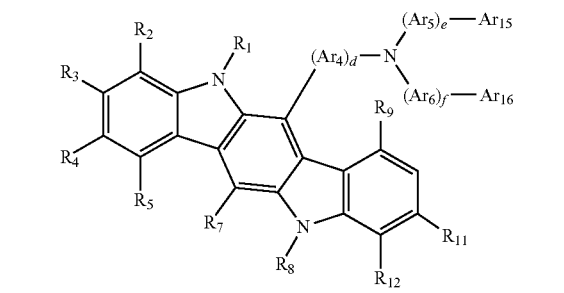

Formula 2c

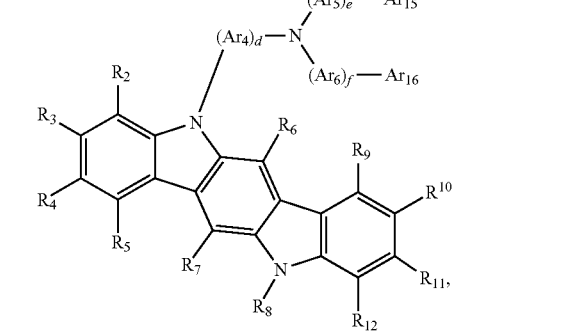

Formula 2d wherein, in Formulae 2a to 2d:

$R_1$ through $R_{12}$ are each independently a hydrogen atom, a heavy hydrogen atom, a halogen atom, a hydroxyl group, a cyano group, a substituted or unsubstituted C₁-C₃₀ alkyl group, a substituted or unsubstituted C₂-C₃₀ alkenyl group, a substituted or unsubstituted C₂-C₃₀ alkynyl group, a substituted or unsubstituted C₁-C₃₀ alkoxy group, the first substituent, the second substituent, or the third substituent;

$Ar_1$ through $Ar_6$, among the first to third substituents, are each independently a substituted or unsubstituted C₁-C₃₀ alkylene group, a substituted or unsubstituted C₂-C₃₀ alkenylene group, a substituted or unsubstituted C₅-C₃₀ arylene group, or a substituted or unsubstituted C₃-C₃₀ heteroarylene group;

$Ar_{11}$, $Ar_{12}$, $Ar_{13}$, $Ar_{15}$, and $Ar_{16}$, among the first to third substituents, are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, or a substituted or unsubstituted $C_3$-$C_{30}$ heteroaryl group;

a, b, c, e, and f are each independently an integer of 0 to 10;

d is an integer of 1 to 10; and

"a" groups of $Ar_1$ in the group of —$(Ar_1)_a$—$Ar_{11}$ of the first substituent are identical to or different from each other; "b" groups of $Ar_2$ in the group of —$(Ar_2)_b$—$Ar_{12}$ of the second substituent are identical to or different from each other; "c" groups of $Ar_3$ in the group of —$(Ar_3)_c$—$Ar_{13}$ of the second substituent are identical to or different from each other; "e" groups of $Ar_5$ in the group of —$(Ar_5)_e$—$Ar_{15}$ of the third substituent are identical to or different from each other; and "f" groups of $Ar_6$ in the group of —$(Ar_6)_f$—$Ar_{16}$ of the third substituent are identical to or different from each other.

13. The condensed-cyclic compound as claimed in claim 12, wherein:

$Ar_4$ includes at least one of a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$ alkyl)fluorenylene group, a ($C_6$-$C_{14}$ aryl)fluorenylene group, a di($C_6$-$C_{14}$ aryl)fluorenylene group, a naphthylene group, a $C_1$-$C_{10}$ alkylnaphthylene group, a di($C_1$-$C_{10}$ alkyl)naphthylene group, a ($C_6$-$C_{14}$ aryl)naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$ aryl)anthrylene group, and a di($C_6$-$C_{14}$ aryl)anthrylene group; and d is 1, 2, or 3.

14. The condensed-cyclic compound as claimed in claim 12, wherein the second substituent and —N[—$(Ar_5)_e$—$Ar_{15}$][—$(Ar_6)_f$—$Ar_{16}$] of the third substituent are each independently represented by any one of Formulae 6A through 6K below:

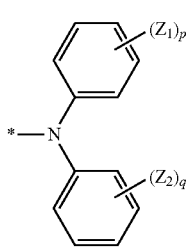

Formula 6A

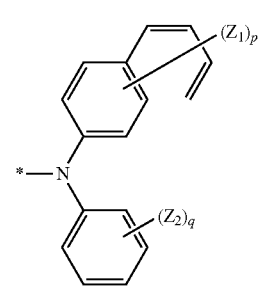

Formula 6B

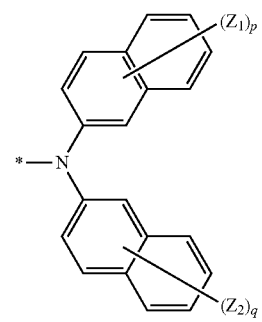

Formula 6C

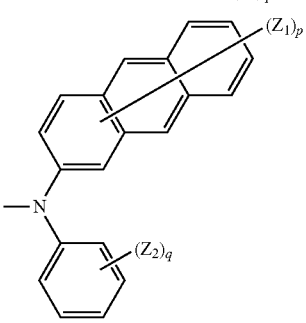

Formula 6D

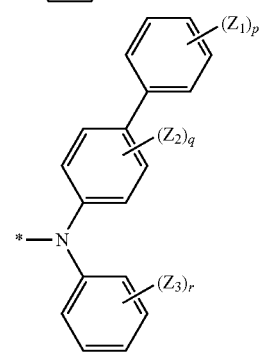

Formula 6E

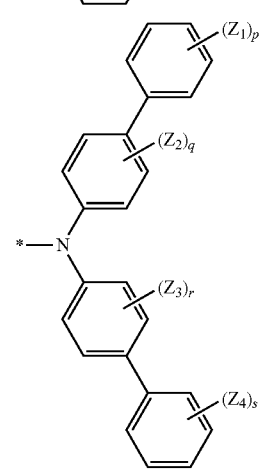

Formula 6F

-continued

Formula 6G
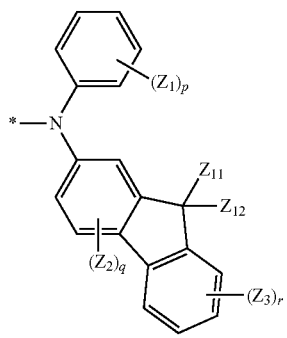

Formula 6H
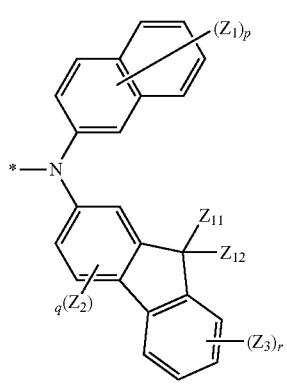

Formula 6I
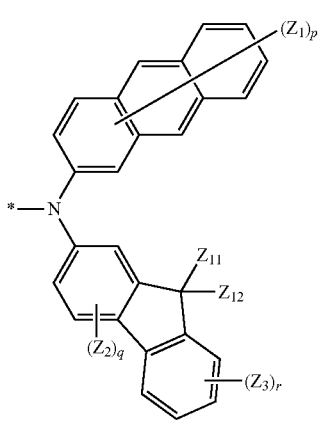

Formula 6J
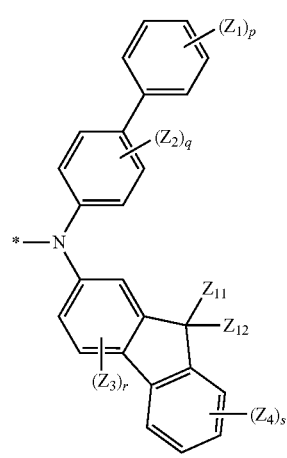

-continued

Formula 6K
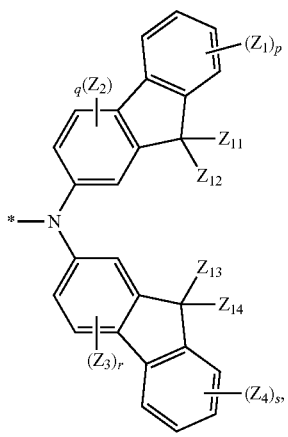

and in Formulae 6A to 6K:

$Z_1$ through $Z_4$ and $Z_{11}$ through $Z_{14}$ are each independently a hydrogen atom, a heavy hydrogen atom, a $C_1$-$C_{10}$ alkyl group, a $C_1$-$C_{10}$ alkoxy group, or a $C_6$-$C_{14}$ aryl group, p, q, r, and s are each independently an integer of 1 to 8, and

* is a bonding site with $Ar_4$ or with a ring atom constituting a backbone of Formula 1.

15. The condensed-cyclic compound as claimed in claim 1, wherein the condensed-cyclic compound represented by Formula 1 is represented by any one of Formulae 3a through 3e below:

Formula 3a
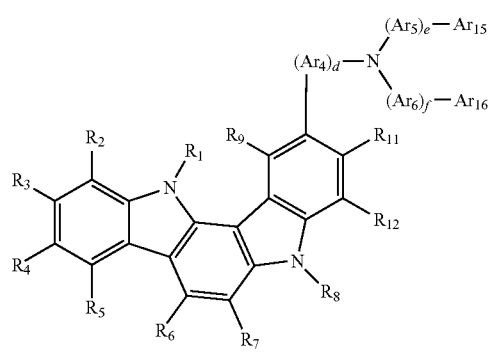

Formula 3b
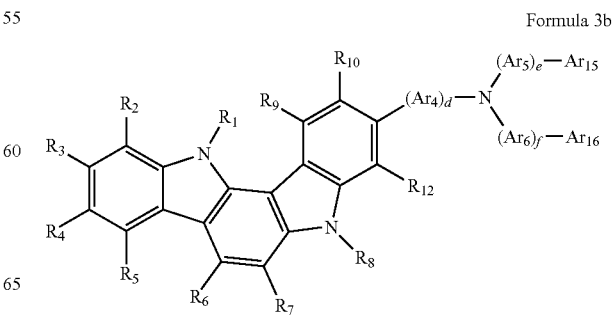

-continued

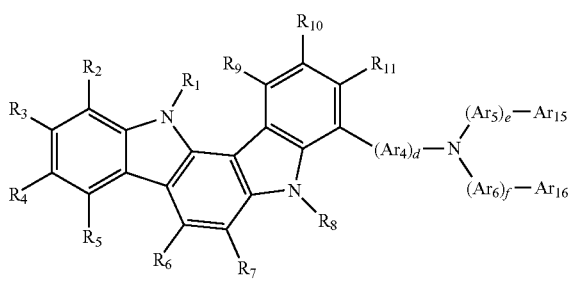

Formula 3c

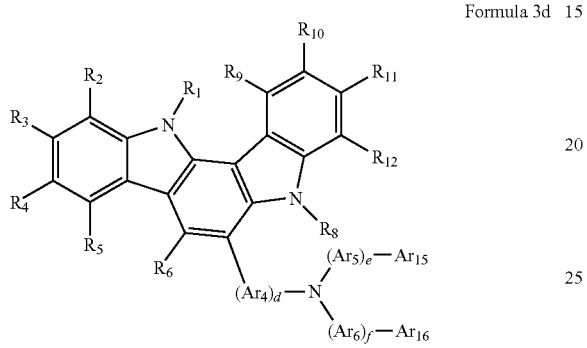

Formula 3d

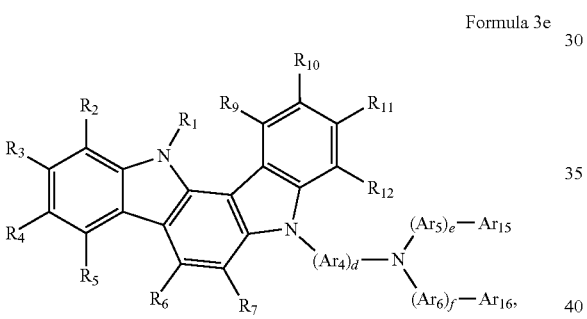

Formula 3e wherein, in Formulae 3a to 3e:

$R_1$ through $R_{12}$ are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, the first substituent, the second substituent, or the third substituent;

$Ar_1$ through $Ar_6$, among the first to third substituents, are each independently a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, or a substituted or unsubstituted $C_3$-$C_{30}$ heteroarylene group;

$Ar_{11}$, $Ar_{12}$, $Ar_{13}$, $Ar_{15}$, and $Ar_{16}$ are each independently a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, or a substituted or unsubstituted $C_3$-$C_{30}$ heteroaryl group;

a, b, c, e, and f are each independently an integer of 0 to 10;

d is an integer of 1 to 10;

"a" groups of $Ar_1$ in the group of —$(Ar_1)_a$—$Ar_{11}$ of the first substituent are identical to or different from each other; "b" groups of $Ar_2$ in the group of —$(Ar_2)_b$—$Ar_{12}$ of the second substituent are identical to or different from each other; "c" groups of $Ar_3$ in the group of —$(Ar_3)_c$—$Ar_{13}$ of the second substituent are identical to or different from each other; "e" groups of $Ar_5$ in the group of —$(Ar_5)_e$—$Ar_{15}$ of the third substituent are identical to or different from each other; and "f" groups of $Ar_6$ in the group of —$(Ar_6)_f$—$Ar_{16}$ of the third substituent are identical to or different from each other.

16. The condensed-cyclic compound as claimed in claim 15, wherein:

$Ar_4$ includes at least one of a phenylene group, a $C_1$-$C_{10}$ alkylphenylene group, a di($C_1$-$C_{10}$ alkyl)phenylene group, a ($C_6$-$C_{14}$ aryl)phenylene group, a di($C_6$-$C_{14}$ aryl)phenylene group, a carbazolylene group, a $C_1$-$C_{10}$ alkylcarbazolylene group, a di($C_1$-$C_{10}$ alkyl)carbazolylene group, a $C_6$-$C_{14}$ arylcarbazolylene group, a di($C_6$-$C_{14}$ aryl)carbazolylene group, a fluorenylene group, a $C_1$-$C_{10}$ alkylfluorenylene group, a di($C_1$-$C_{10}$ alkyl)fluorenylene group, a ($C_6$-$C_{14}$ aryl)fluorenylene group, a di($C_6$-$C_{14}$ aryl)fluorenylene group, a naphthylene group, a $C_1$-$C_{10}$ alkylnaphthylene group, a di($C_1$-$C_{10}$ alkyl)naphthylene group, a ($C_6$-$C_{14}$ aryl)naphthylene group, a di($C_6$-$C_{14}$ aryl)naphthylene group, an anthrylene group, a $C_1$-$C_{10}$ alkylanthrylene group, a di($C_1$-$C_{10}$ alkyl)anthrylene group, a ($C_6$-$C_{14}$ aryl)anthrylene group, and a di($C_6$-$C_{14}$ aryl)anthrylene group; and d is 1, 2, or 3.

17. The condensed-cyclic compound as claimed in claim 15, wherein the second substitutent and —N[—$(Ar_5)_e$—$Ar_{15}$][—$(Ar_6)_f$—$Ar_{16}$] of the third substitutent are each independently represented by any one of Formulae 6A through 6K below:

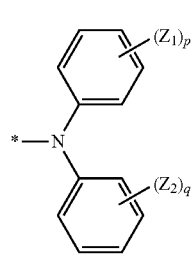

Formula 6A

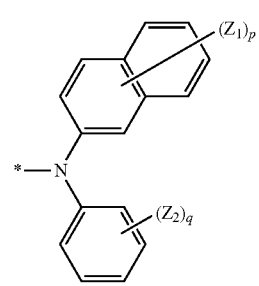

Formula 6B

-continued
Formula 6C
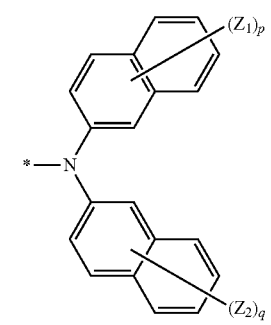
Formula 6D
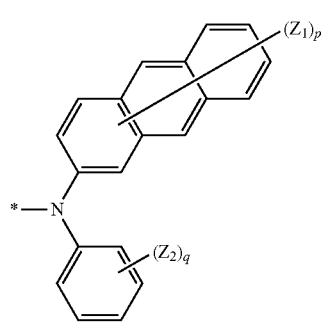
Formula 6E
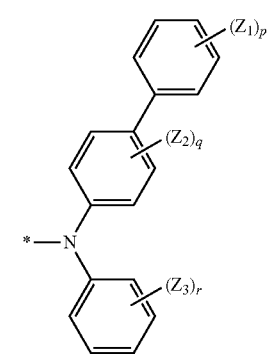
Formula 6F
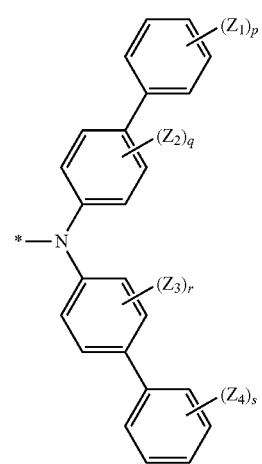
Formula 6G
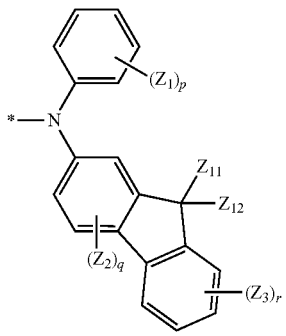
Formula 6H
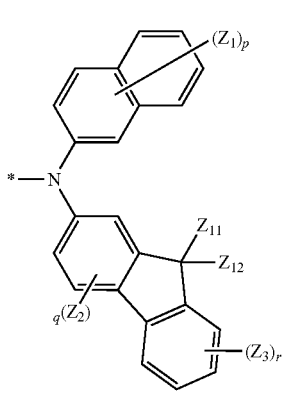
Formula 6I
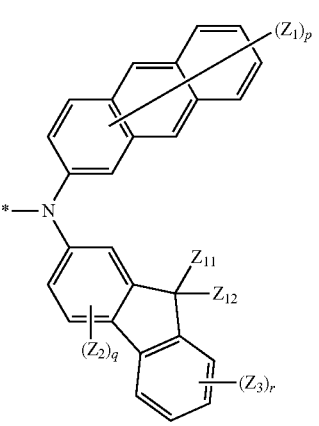
Formula 6J
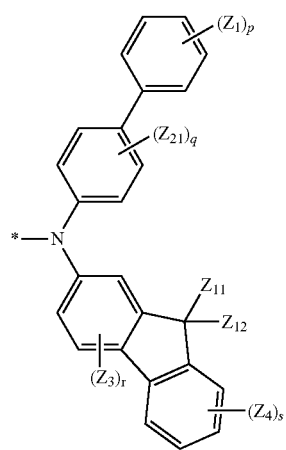

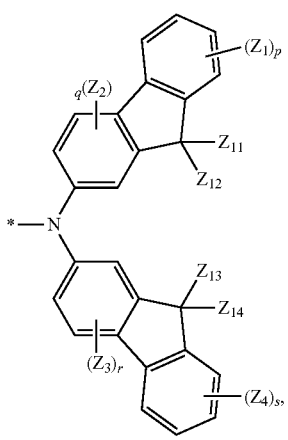

and in Formulae 6A to 6K:

$Z_1$ through $Z_4$ and $Z_{11}$ through $Z_{14}$ are each independently a hydrogen group, a heavy hydrogen atom, a $C_1$-$C_{10}$ alkyl group, a $C_1$-$C_{10}$ alkoxy group, or a $C_6$-$C_{14}$ aryl group, p, q, r, and s are each independently an integer of 1 to 8, and

* is a bonding site with $Ar_4$ or with a ring atom constituting a backbone of Formula 1.

18. An organic light-emitting device, comprising:
a first electrode,
a second electrode opposite to the first electrode, and
a first layer between the first electrode and the second electrode, the first layer including the condensed-cyclic compound of claim 1.

19. The organic light-emitting device as claimed in claim 18, wherein the first layer includes at least one of a hole injection layer, a hole transport layer, a functional layer having both hole injection function and hole transport function, an emission layer, an electron transport layer, and an electron injection layer.

20. The organic light-emitting device as claimed in claim 18, further comprising, between the first electrode and the second electrode, at least one of a hole injection layer, a hole transport layer, a functional layer having both hole injection function and hole transport function, an emission layer, a hole blocking layer, an electron transport layer, and an electron injection layer.

21. The organic light-emitting device as claimed in claim 20, wherein at least one of the hole injection layer, the hole transport layer, or the functional layer further comprises a charge-generating material.

22. The organic light-emitting device as claims in claim 20, wherein the emission layer comprises a host and a dopant, wherein the dopant is a fluorescent dopant or a phosphorescent dopant.

23. The organic light-emitting device as claimed in claim 22, wherein the phosphorescent dopant is an organic metal complex comprising at least one of iridium, platinum, osmium, rhenium, titanium, zirconium, and hafnium.

24. The organic light-emitting device as claimed in claim 20, wherein the electron transport layer comprises an electron transporting organic material and a metal-containing material.

25. The organic light-emitting device as claimed in claim 24, wherein the metal-containing material comprises a lithium complex.

26. The organic light-emitting device as claimed in claim 18, wherein the first layer is a hole injection layer, a hole transport layer, or a functional layer having both hole injection function and hole transport function, and further comprises a charge-generating material.

27. The organic light-emitting device as claimed in claim 18, wherein the first layer is an emission layer, and further comprises a phosphorescent dopant.

* * * * *